(12) United States Patent
Fischer et al.

(10) Patent No.: US 8,012,474 B2
(45) Date of Patent: Sep. 6, 2011

(54) ANTI-RANTES ANTIBODIES

(75) Inventors: Nicolas Fischer, Geneva (CH); Marie Kosco-Vilbois, Minzier (FR); Francois Mach, Vesenaz (CH)

(73) Assignee: Nov Immune S.A., Geneva (CH)

( * ) Notice: Subject to any disclaimer, the term of this patent is extended or adjusted under 35 U.S.C. 154(b) by 337 days.

(21) Appl. No.: 12/221,485

(22) Filed: Aug. 4, 2008

(65) Prior Publication Data
US 2009/0148455 A1 Jun. 11, 2009

Related U.S. Application Data

(60) Provisional application No. 60/963,271, filed on Aug. 2, 2007.

(51) Int. Cl.
*A61K 39/395* (2006.01)
*C07K 16/18* (2006.01)
*C07K 16/24* (2006.01)

(52) U.S. Cl. ............... 424/130.1; 424/141.1; 424/142.1; 424/145.1; 530/387.1; 530/388.1; 530/388.15; 530/388.23

(58) Field of Classification Search .................. None
See application file for complete search history.

(56) References Cited

U.S. PATENT DOCUMENTS

| | | | | |
|---|---|---|---|---|
| 5,834,419 | A | 11/1998 | McFadden et al. | 514/2 |
| 5,840,544 | A | 11/1998 | Hawkins et al. | 435/69.5 |
| 5,965,697 | A | 10/1999 | Czaplewski et al. | 530/324 |
| 6,015,883 | A | 1/2000 | Hawkins et al. | 530/351 |
| 6,159,711 | A | 12/2000 | Proudfoot et al. | 435/69.5 |
| 6,214,540 | B1 | 4/2001 | DeVico et al. | 435/5 |
| 6,238,666 | B1 | 5/2001 | Hawkins et al. | 424/145.1 |
| 6,420,346 | B1 | 7/2002 | Karin | 514/44 |
| 6,534,626 | B1 | 3/2003 | Oravecz et al. | 530/300 |
| 6,589,933 | B1 | 7/2003 | McFadden et al. | 514/2 |
| 6,608,177 | B1 | 8/2003 | Lusso et al. | 530/351 |
| 2003/0059937 | A1 | 3/2003 | Ruben et al. | 435/435 |
| 2003/0099647 | A1 | 5/2003 | Deshpande et al. | 424/145.1 |
| 2004/0191255 | A1 | 9/2004 | Lillard et al. | 424/145.1 |
| 2006/0110394 | A1 | 5/2006 | Bendig et al. | 424/155.1 |
| 2006/0246069 | A1 | 11/2006 | Sugimura | 424/145.1 |

FOREIGN PATENT DOCUMENTS

| | | |
|---|---|---|
| EP | 0 905 240 A1 | 3/1999 |
| EP | 0 905 241 A1 | 3/1999 |
| WO | WO 96/17935 | 6/1996 |
| WO | WO 98/06751 | 2/1998 |
| WO | WO 98/13495 | 4/1998 |
| WO | WO 98/51705 | 11/1998 |
| WO | WO 99/20759 | 4/1999 |
| WO | WO 99/28474 | 6/1999 |
| WO | WO 99/32619 | 7/1999 |
| WO | WO 00/16796 | 3/2000 |
| WO | WO 00/27880 | 5/2000 |
| WO | WO 00/44895 | 8/2000 |
| WO | WO 01/29058 | 4/2001 |
| WO | WO 01/75164 | 10/2001 |
| WO | WO 01/80882 | 11/2001 |
| WO | WO 01/89304 | 11/2001 |
| WO | WO 01/92513 | 12/2001 |
| WO | WO 02/16620 | 2/2002 |
| WO | WO 02/28419 | 4/2002 |
| WO | WO 02/29858 | 4/2002 |
| WO | WO 02/43758 | 6/2002 |
| WO | WO 02/090381 | 11/2002 |
| WO | WO 03/002597 | 1/2003 |
| WO | WO 03/035106 | 5/2003 |
| WO | WO 03/051921 | 6/2003 |
| WO | WO 03/084562 | 10/2003 |
| WO | WO 2004/024921 | 3/2004 |
| WO | WO 2004/029094 | 4/2004 |
| WO | WO 2004/045525 | 6/2004 |
| WO | WO 2004/062688 | 7/2004 |
| WO | WO 2005/054285 | * 6/2005 |
| WO | WO 2007/048186 | 5/2007 |

OTHER PUBLICATIONS

Pirollo et al. Targeted delivery of small interfering RNA: approaching effective cancer therapes. Cancer Res 68(5): 1247-1250, 2008.*
Vidal et al. Making sense of antisense. Eur J Cancer 41(18): 2812-2818, 2005.*
Phillips, A.J. The challenge of gene therapy and DNA delivery. J Pharm Pharmacol 53: 1169-1174, 2001.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Brummell et al. (Biochemistry 32:1180-1187 (1993)).*

(Continued)

*Primary Examiner* — Bridget E Bunner
(74) *Attorney, Agent, or Firm* — Mintz Levin Cohn Ferris Glovsky and Popeo, P.C.; Ivor R. Elrifi

(57) ABSTRACT

The invention relates to fully human monoclonal antibodies, and fragments thereof, that bind to the chemokine Regulated upon Activation, Normal T-cell Expressed, and Secreted (RANTES, CCL5), thereby modulating the interaction between RANTES and one of more of its receptors, such as, e.g., CCR1, CCR3, CCR4 and CCR5, and/or modulating the biological activities of RANTES. The invention also relates to the use of these or any anti-RANTES antibodies in the prevention or treatment of immune-related disorders and in the amelioration of one or more symptoms associated with an immune-related disorder.

13 Claims, 17 Drawing Sheets

OTHER PUBLICATIONS

Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Lehner et al. J Immunol 166: 7446-7455, 2001.*
Nardese et al. Nature Struct Biol 8(7): 611-615, 2001.*
Glass et al. J Immunol 172: 4018-4025, 2004.*
Pakianathan et al. Biochemistry 36: 9642-9648, 1997.*
Mix et al. J Neurol 253 (Suppl 5): V/9-V/17, 2006.*
Chothia et al., "Conformations of immunoglobulin hypervariable regions," Nature, vol. 342:877-883 (1989).
Vaughan, et al., "Human Antibodies with Sub-nanomolar Affinities Isolated from a Large Non-immunized Phage Display Library," Nature Biotechnology, vol. 14:309-314 (1996).
Burns et al., "A new monoclonal antibody, mAb 4A12, identifies a role for the glycosaminoglycan (GAG) binding domain of RANTES in the antiviral effect against HIV-1 and intracellular Ca2+ signaling," J. Exp. Med., vol. 188: 1917-27 (1998).
Gong et al., "RANTES and MCP-3 antagonists bind multiple chemokine receptors," JBC, vol. 271: 10521-27 (1996).
von Luettichau et al., "RANTES chemokine expression in diseased and normal human tissues," Cytokine, vol. 8: 89-98 (1996).

* cited by examiner

ANTI-RANTES ANTIBODIES

RELATED APPLICATION

This application claims the benefit of U.S. Provisional Application No. 60/963,271, filed Aug. 2, 2007, the contents of which are hereby incorporated by reference in their entirety.

FIELD OF THE INVENTION

This invention relates generally to fully human monoclonal antibodies that bind to RANTES (Regulated upon Activation, Normal T-cell Expressed, and Secreted) as well as to methods for use thereof.

BACKGROUND OF THE INVENTION

RANTES (Regulated upon Activation, Normal T-cell Expressed, and Secreted, CCL5) is a chemokine that is a chemoattractant for eosinophils, monocytes, and lymphocytes.

Elevated levels of RANTES expression has been implicated in a variety of diseases and disorders. Accordingly, there exists a need for therapies that target RANTES activity.

SUMMARY OF THE INVENTION

The present invention provides monoclonal antibodies, such as fully human monoclonal antibodies, that specifically bind Regulated upon Activation, Normal T-cell Expressed, and Secreted (RANTES, also referred to herein as CCL5). Exemplary monoclonal antibodies include the antibodies referred to herein as 1D9, 1E4, C8, 3E7, 4D8, 5E1, 6A8, 7B5, CG11, BG11, A9, E6, H6, G2, E10, C10, 2D1, A5, H11, D1 and/or E7. Alternatively, the monoclonal antibody is an antibody that binds to the same epitope as 1D9, 1E4, C8, 3E7, 4D8, 5E1, 6A8, 7B5, CG11, BG11, A9, E6, H6, G2, E10, C10, 2D1, A5, H11, D1 and/or E7. The antibodies are respectively referred to herein as huRANTES antibodies. huRANTES antibodies include fully human monoclonal antibodies, as well as humanized monoclonal antibodies and chimeric antibodies.

huRANTES antibodies of the invention also include antibodies that include a heavy chain variable amino acid sequence that is at least 90%, 92%, 95%, 97%, 98%, 99% or more identical the amino acid sequence of SEQ ID NO: 2, 18, 22, 38, 48, 52, 56, 60, 68, 84, 100, 116, 132, 148, 164, 180, 200, 216, 232, or 248 and/or a light chain variable amino acid that is at least 90%, 92%, 95%, 97%, 98%, 99% or more identical the amino acid sequence of SEQ ID NO: 4, 24, 40, 62, 70, 86, 102, 118, 134, 150, 166, 182, 196, 202, 218, 234, or 250.

Preferably, the three heavy chain complementarity determining regions (CDRs) include an amino acid sequence at least 90%, 92%, 95%, 97%, 98%, 99% or more identical to each of: (i) a VH CDR1 sequence selected from SEQ ID NO: 8, 28, 44, 74, 90, 106, 122, 138, 154, and 222; (ii) a VH CDR2 sequence selected from SEQ ID NO: 9, 29, 45, 75, 91, 107, 123, 139, 155, 207, 223, 239, and 255; (iii) a VH CDR3 sequence selected from SEQ ID NOs: 10, 20, 30, 46, 50, 54, 58, 64, 76, 92, 108, 124, 140, 156, 169 188, 208, 224, and 240 and a light chain with three CDR that include an amino acid sequence at least 90%, 92%, 95%, 97%, 98%, 99% or more identical to each of (iv) a VL CDR1 sequence selected from SEQ ID NO: 14, 34, 77, 96, 112, 128, 144, 160, 176, 190, 192, 212, 228, and 244; (v) a VL CDR2 sequence selected from SEQ ID NO: 15, 35, 81, 97, 113, 129, 145, 161, 177, 191, 193, 213, 229, and 245; and (vi) a VL CDR3 sequence selected from SEQ ID NO: 16, 36, 66, 82, 98, 114, 130, 146, 162, 178, 194, 214, 230, 235 and 246.

Preferably, the huRANTES antibodies are formatted in an IgG isotype. More preferably, the huRANTES antibodies are formatted in an IgG1 isotype.

Exemplary IgG1-formatted antibody are the IgG1-formatted 1D9, 1E4 and C8 antibodies comprising the heavy chain sequence and light chain sequence shown below, and the CDR sequences are shown in boxes:

```
> 1D9 Heavy chain amino acid sequence (SEQ ID NO: 167)

QVQLVQSGAEVKKPGASVKVSCKVSGYTLT EFAMH WVRQAPGKGLEWMGG FVPEDGETIYAQK
FQG RVTMTEDTSTDTAYMELSSLRSEDTAVYYCAT DPLYTPGLEP WGQGTTVTVSSASTKGPS
VFPLAPSSKSTSGGTAALGCLVKDYFPEPVTVSWNSGALTSGVHTFPAVLQSSGLYSLSSVVT
VPSSSLGTQTYICNVNHKPSNTKVDKRVEPKSCDKTHTCPAPELLGGPSVFLFPPKPKDT
LMISRTPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQK
SLSLSPGK

> 1D9 Light chain amino acid sequence (SED ID NO: 168)

SYVLTQPPSVSVAPGQTARITC GGNNIESKSVH WYQQKPGQAPVLVVY DDSDRPS GIPERFSG
SNSGNTATLTISRVEAGDEADYYC QVWDSNTDHWV FGGGTKLTVLGQPKAAPSVTLFPPSSEE
LQANKATLVCLISDFYPGAVTVAWKADSSPVKAGVETTTPSKQSNNKYAASSYLSLTPEQWKS
HRSYSCQVTHEGSTVEKTVAPTECS

> 1E4 Heavy chain amino acid sequence (SEQ ID NO: 238)

QVQLVQSGAEVKKPGASVKVSCKVSGYTLT EFAMH WVRQAPGKGLEWMGG FVPEDGETIYAQK
FQG RVTMTEDTSTDTAYMELSSLRSEDTAVYYCAT DPLYEGSFSV WGQGTTVTVSSASTKGPS
VFPLAPSSKSTSGGTAALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYNSTYRVVSVLTVLHQDW
LNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQK
SLSLSPGK

> 1E4 Light chain amino acid sequence (SEQ ID NO: 254)

SYVLTQPPSVSVAPGQTARITC GGNNIESKSVH WYQQKPGQAPVLVVY DDSDRPS GIPERFSG
SNSGNTATLTISRVEAGDEADYYC QVWDSNTDHWV FGGGTKLTVLGQPKAAPSVTLFPPSSEE
LQANKATLVCLISDFYPGAVTVAWKADSSPVKAGVETTTPSKQSNNKYAASSYLSLTPEQWKS
HRSYSCQVTHEGSTVEKTVAPTECS
```

-continued

> C8 Heavy chain amino acid sequence (SEQ ID NO: 186)

QVQLVESGGGVVQPGRSLRLSCAASGFTFS`SYAMH`WVRQAPGKGLEWVA`VISYDGSNKYYADS`
`VKG`RFTISRDNSKNTLYLQMNSLRAESTAVYYCAR`ETEPHYYYYMDV`WGRGTLVTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKRVEPKSCDKTHTCPPCPAPELLGGPSVFLFPPKP
KDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHY
TQKSLSLSPGK

> C8 Light chain amino acid sequence (SEQ ID NO: 187)

SYVLTQPPSVSVAPGQTARITC`EGDDTDIGTVN`WYQQKPGQAPVLVVIS`EDGYRPS`GIPERFSG
SNSGNTATLTISRVEAGDEADYYC`QFWDVDSDHPV`FGGGTQLTVLGQPKAAPSVTLFPPSSEE
LQANKATLVCLISDFYPGAVTVAWKADSSPVKAGVETTTPSKQSNNKYAASSYLSLTPEQWKS
HRSYSCQVTHEGSTVEKTVAPTECS

The closest germline for the huRANTES antibodies described herein are shown below in Table 1:

TABLE 1

Closest germlines for the huRANTES antibodies. Antibodies marked in italic were derived by an affinity maturation process from antibody 2D1 (Lower part of the table).

| Clone ID | VH dp number | VL dp number |
|---|---|---|
| CG11 | Vh1_DP-3_(1-f) | Vlambda1_DPL8_(1e) |
| BG11 | Vh1_DP-5_(1-24) | Vlambda3_DPL16_(3l) |
| A9 | Vh3_DP-47_(3-23) | Vlambda6_6a |
| E6 | Vh1_DP-5_(1-24) | Vlambda6_6a |
| H6 | Vh1_DP-5_(1-24) | Vlambda1_DPL8_(1e) |
| G2 | Vh1_DP-5_(1-24) | Vlambda2_DPL11_(2a2) |
| E10 | Vh3_DP-46_(3-30.3) | Vlambda3_3h |
| C10 | Vh3_DP-47_(3-23) | Vlambda3_3h |
| 2D1 | Vh1_DP-5_(1-24) | Vlambda3_3h |
| A5 | Vh1_DP-5_(1-24) | Vlambda3_3h |
| H11 | Vh1_DP-10_(1-69) | Vlambda1_DPL8_(1e) |
| D1 | Vh1_DP-3_(1-f) | Vlambda1_DPL8_(1e) |
| E7 | Vh1_DP-10_(1-69) | Vlambda1_DPL9_(1f) |
| C8 | Vh3_DP-46_(3-30.3) | Vlambda3_3h |
| 1D9 | Vh1_DP-5_(1-24) | Vlambda3_3h |
| 1E4 | Vh1_DP-5_(1-24) | Vlambda3_3h |
| 3E7 | Vh1_DP-5_(1-24) | Vlambda3_3h |
| 4D8 | Vh1_DP-5_(1-24) | Vlambda3_3h |
| 5E1 | Vh1_DP-5_(1-24) | Vlambda3_3h |
| 6A8 | Vh1_DP-5_(1-24) | Vlambda3_3h |
| 7B5 | Vh1_DP-5_(1-24) | Vlambda3_3h |

The invention also provides antibodies that bind human RANTES when human RANTES is bound to glycosaminoglycan (GAG), i.e., bind human RANTES in the context of GAG. In a preferred embodiment, these antibodies include (a) a $V_H$ CDR1 region comprising the amino acid sequence of SEQ ID NO: 8, 28, 44, 90, 106, 122 or 154; (b) a $V_H$ CDR2 region comprising the amino acid sequence of SEQ ID NO: 9, 29, 45, 91, 107, 123, 155, or 207; (c) a $V_H$ CDR3 region comprising the amino acid sequence of SEQ ID NO: 10, 20, 30, 64, 92, 124, 156, 188, or 208, (d) a $V_L$ CDR1 region comprising the amino acid sequence of SEQ ID NO: 14, 34, 96, 128, 160, 176, 192, or 212; (e) a $V_L$ CDR2 region comprising the amino acid sequence of SEQ ID NO: 15, 35, 97, 129, 161, 177, 193, or 213; and (f) a $V_L$ CDR3 region comprising the amino acid sequence of SEQ ID NO: 16, 36, 98, 130, 162, 178, 194, or 214.

In some embodiments, the antibody is a monoclonal antibody or an antigen-binding fragment thereof. In some embodiments, the antibody is a fully human monoclonal antibody or an antigen-binding fragment thereof. In some embodiments, the antibody is an IgG isotype, such as, for example, an IgG1 isotype.

The invention also provides antagonist molecules of human RANTES, and in particular, antagonists of human RANTES proteins, polypeptides and/or peptides that include at least amino acid residues 16-18 of the mature amino acid sequence of human RANTES, e.g., SEQ ID NO: 170 shown in FIG. 6. The anti-human RANTES antagonists bind to, or otherwise interact with, a human RANTES protein, polypeptide, and/or peptide to modulate, e.g., reduce, inhibit or otherwise interfere, partially or completely with a biological function of a human RANTES protein, such as for example, the binding of RANTES to a receptor such as CCR1, CCR3, CCR4 and/or CCR5, or the binding of RANTES to glycosaminoglycans (GAG).

In a preferred embodiment, the ability of the anti-human RANTES antagonists to bind to, or otherwise interact with, human RANTES protein to modulate one or more biological functions of human RANTES is dependent upon the presence of amino acid residues 16-18 of the mature human RANTES sequence such as SEQ ID NO: 170. In this embodiment, the antagonist molecules do not bind a human RANTES polypeptide that lacks amino acid residues 16-18 of SEQ ID NO: 170.

The anti-RANTES antagonist molecules provided herein completely or partially reduce or otherwise modulate RANTES expression or activity upon binding to, or otherwise interacting with, human RANTES. The reduction or modulation of a biological function of RANTES is complete or partial upon interaction between the antagonist and the human RANTES protein, polypeptide and/or peptide. The anti-huRANTES antagonists are considered to completely inhibit RANTES expression or activity when the level of RANTES expression or activity in the presence of the anti-huRANTES antagonist is decreased by at least 95%, e.g., by 96%, 97%, 98%, 99% or 100% as compared to the level of RANTES expression or activity in the absence of interaction, e.g., binding with an anti-huRANTES antagonist described herein. The anti-huRANTES antagonists are considered to partially inhibit RANTES expression or activity when the level of RANTES expression or activity in the presence of the anti-huRANTES antagonist is decreased by less than 95%, e.g., 10%, 20%, 25%, 30%, 40%, 50%, 60%, 75%, 80%, 85% or 90% as compared to the level of RANTES expression or activity in the absence of interaction, e.g., binding with an anti-huRANTES antagonist described herein.

In some embodiments, the anti-RANTES antagonist molecule is selected from a small molecule inhibitor; a polypeptide, a peptide, a RANTES-derived mutant polypeptide, a RANTES-derived polypeptide variant, a RANTES receptor-derived mutant polypeptide, e.g., a mutated CCR1, CCR3, CCR4 or CCR5 protein, polypeptide or peptide, a RANTES receptor-derived polypeptide variant, e.g., a CCR1, CCR3, CCR4 or CCR5 variant peptide, polypeptide or protein, and a nucleic acid-based antagonist.

In some embodiments, the anti-RANTES antagonist molecule is an isolated monoclonal anti-human RANTES antibody or antigen-binding fragment thereof. Preferably, the antibody (or antigen-binding fragment thereof) binds to amino acid residues 16-18 of the mature amino acid sequence of human RANTES, e.g., SEQ ID NO: 170 shown in FIG. 6. In some embodiments, the anti-RANTES antibody is a fully human monoclonal anti-human RANTES antibody or antigen-binding fragment thereof. In some embodiments, the antibody is an IgG isotype, such as an IgG1 isotype.

In some embodiments, the anti-RANTES antagonist molecule is a mutated RANTES polypeptide or RANTES-derived variant polypeptide or a mutated RANTES receptor, for example, selected from CCR1, CCR3, CCR4, and CCR5, or a variant of a RANTES receptor polypeptide, such as CCR1, CCR3, CCR4, or CCR5, that modulates an activity of RANTES selected from the ability of RANTES to bind to a receptor selected from CCR1, CCR3, CCR4, and CCR5, the ability of RANTES to bind a glycosaminoglycan and the ability of RANTES to form oligomers.

In some embodiments, the anti-RANTES antagonist molecule is a nucleic acid-based antagonist such as, for example, an aptamer or other oligonucleotide capable of interacting with targets, such as proteins, polypeptides, small molecules, carbohydrates, peptides or any other biological molecules, through interactions other than Watson-Crick base pairing.

The invention also provides methods of treating, preventing, alleviating a symptom of, or otherwise mitigating ischemia, a clinical indication associated with ischemia and/or reperfusion injury in a subject. The invention is based on the discovery that modulation, particularly, inhibition or other reduction of RANTES expression or activity inhibits ischemia and/or reperfusion injury in an animal model for ischemia and reperfusion. Accordingly, the invention provides methods of preventing or inhibiting ischemia, a clinical indication associated with ischemia, reperfusion injury, in a subject, in a bodily tissue and/or in a tissue or organ to be transplanted. In the methods provided herein, the subject to be treated is administered an antagonist of RANTES. Likewise, in the treatment of organs to be transplanted, the organ, or a portion thereof, is contacted with an antagonist of RANTES. The methods provided herein are useful in vivo and ex vivo.

Suitable antagonists of RANTES include any antibody or fragment thereof that inhibits, neutralizes or otherwise interferes with the expression and/or activity of RANTES, such as, e.g., the huRANTES antibodies provided herein; small molecule inhibitors; proteins, polypeptides, peptides; protein-, polypeptide- and/or peptide-based antagonists such as RANTES mutants and/or other RANTES variants and or RANTES receptor-based mutants and/or variants, such as, for example, mutated or variant versions of CCR1, CCR3, CCR4 or CCR5 polypeptides; nucleic acid based antagonists such as siRNA and/or anti-sense RNA, and/or aptamers; and/or fragments thereof that inhibit, neutralize or otherwise interfere with the expression and/or activity of RANTES.

Examples of polypeptide-based antagonists of RANTES include modified variants of RANTES that inhibit, neutralize or otherwise interfere with the expression and/or activity of RANTES. Variants of RANTES that are known to antagonize RANTES, for example, by decreasing the ability of RANTES to bind to glycosaminoglycans (GAG), include the RANTES mutants and variants described in PCT Publication Nos. WO 2004/062688; WO 2003/0844562; WO 2003/051921; WO 2002/028419; WO 2000/016796 and WO 1996/017935, each of which is hereby incorporated by reference in its entirety.

Examples of nucleic acid-based antagonists of RANTES include short interfering RNA (siRNA) mediated gene silencing where expression products of a RANTES gene are targeted by specific double stranded RANTES derived siRNA nucleotide sequences that are complementary to a segment of the RANTES gene transcript, e.g., at least 19-25 nucleotides long, including the 5' untranslated (UT) region, the ORF, or the 3' UT region. See, e.g., PCT applications WO00/44895, WO99/32619, WO01/75164, WO01/92513, WO 01/29058, WO01/89304, WO02/16620, and WO02/29858, each incorporated by reference herein in their entirety. Nucleic-acid based antagonists of RANTES also include antisense nucleic acids. An antisense nucleic acid comprises a nucleotide sequence that is complementary to a "sense" nucleic acid encoding a RANTES protein or fragment thereof. For example, antisense RANTES antagonists comprise a sequence complementary to at least about 10, 25, 50, 100, 250 or 500 nucleotides or an entire RANTES coding strand, or to only a portion thereof.

Preferably, the RANTES antagonist inhibits, partially or completely, a function of RANTES selected from the ability of RANTES to bind to a corresponding receptor (e.g., CCR1, CCR3, CCR4, and/or CCR5), the ability of RANTES to bind glycosaminoglycans and/or the ability of RANTES to form oligomers. Suitable RANTES antagonists are identified, for example, using the assays and models provided in the Examples below.

The anti-huRANTES antagonists are considered to completely inhibit RANTES expression or activity when the level of RANTES expression or activity in the presence of the anti-huRANTES antagonist is decreased by at least 95%, e.g., by 96%, 97%, 98%, 99% or 100% as compared to the level of RANTES expression or activity in the absence of interaction, e.g., binding with an anti-huRANTES antagonist described herein. The anti-huRANTES antagonists are considered to partially inhibit RANTES expression or activity when the level of RANTES expression or activity in the presence of the anti-huRANTES antagonist is decreased by less than 95%, e.g., 10%, 20%, 25%, 30%, 40%, 50%, 60%, 75%, 80%, 85% or 90% as compared to the level of RANTES expression or activity in the absence of interaction, e.g., binding with an anti-huRANTES antagonist described herein.

In one aspect, the invention provides methods of treating, preventing or alleviating a symptom of ischemia or a clinical indication associated with ischemia by administering a RANTES antagonist, such as a huRANTES antibody, to a subject in need thereof or by contacting an organ in need thereof with a RANTES antagonist, such as a huRANTES antibody. The ischemia to be treated includes cardiac ischemia, cerebral ischemia, renal ischemia, and related ischemic diseases or events. Clinical indications associated with ischemia and reperfusion include, for example, coronary artery disease, cerebral vascular disease, cardiac ischemia, myocardial ischemia, renal ischemia and peripheral vascular disease. Ischemia is a feature of heart diseases including atherosclerosis, myocardial infarction, transient ischemic attacks, cerebrovascular accidents, ruptured arteriovenous malformations, and peripheral artery occlusive disease. The heart, the kidneys, and the brain are among the organs that are the most sensitive to inadequate blood supply. Ischemia in brain tissue is due, for example, to stroke or head injury. Use of a RANTES antagonist, such as a huRANTES antibody, is also envisioned as part of a protocol for optimizing tissue health during extra-corporeal perfusion of organs and/or tissue prior to transplantation, including, for example, heart, lung, and kidney. The organs to be treated using the methods provided herein are contacted in vivo or ex vivo.

The antibodies and compositions provided herein are useful in treating, preventing or otherwise delaying the progression of tissue injury or other damage caused by ischemia or a clinical indication associated with ischemia. For example, a huRANTES antibody or other RANTES antagonist of the invention is administered to a subject in need thereof before an ischemic event, during an ischemic event, after an ischemic event or any combination thereof.

The antibodies, RANTES antagonists and compositions provided herein are also useful in methods of treating, preventing or alleviating a symptom of a reperfusion injury or other tissue damage that occurs in a subject when blood supply returns to a tissue site after a period of ischemia. For example, a RANTES antagonist, such as a huRANTES antibody of the invention, is administered to a subject in need thereof, e.g., during an ischemic event, after an ischemic event or both during and after an ischemic event. In some cases, restoration of blood flow after a period of ischemia can be more damaging than the ischemia. Reintroduction of oxygen causes a greater production of damaging free radicals, resulting in reperfusion injury. With reperfusion injury, tissue damage and/or necrosis can be greatly accelerated. Reperfusion injuries to be treated or prevented include injuries caused by an inflammatory response in the damaged tissue or tissues.

The subject or organ to be transplanted is suffering from or is predisposed to developing ischemia, an ischemic-related disorder, and/or reperfusion related tissue damage. Preferably, the subject is a mammal, and more preferably, the subject is a human.

In another aspect, the invention provides methods of treating, preventing or alleviating a symptom of an immune-related disorder by administering a huRANTES antibody to a subject. For example, the huRANTES antibodies are used to treat, prevent or alleviate a symptom associated with an autoimmune disease or inflammatory disorder. Optionally, the subject is further administered with a second agent such as, but not limited to, an anti-cytokine reagent, anti-chemokine reagent, an anti-cytokine reagent or an anti-chemokine receptor that recognizes the ligand or receptor for proteins such as interleukin 1 (IL-1), IL-2, IL-4, IL-6, IL-12, IL-13, IL-15, IL-17, IL-18, IL-20, IL-21, IL-22, IL-23, IL-27, IL-31, MIP1 alpha, MIP1 beta, IP-10, MCP1, ITAC, MIG, SDF and fractalkine.

The subject is suffering from or is predisposed to developing an immune related disorder, such as, for example, an autoimmune disease or an inflammatory disorder. Preferably, the subject is a mammal, and more preferably, the subject is a human.

DETAILED DESCRIPTION

Figure 1A:
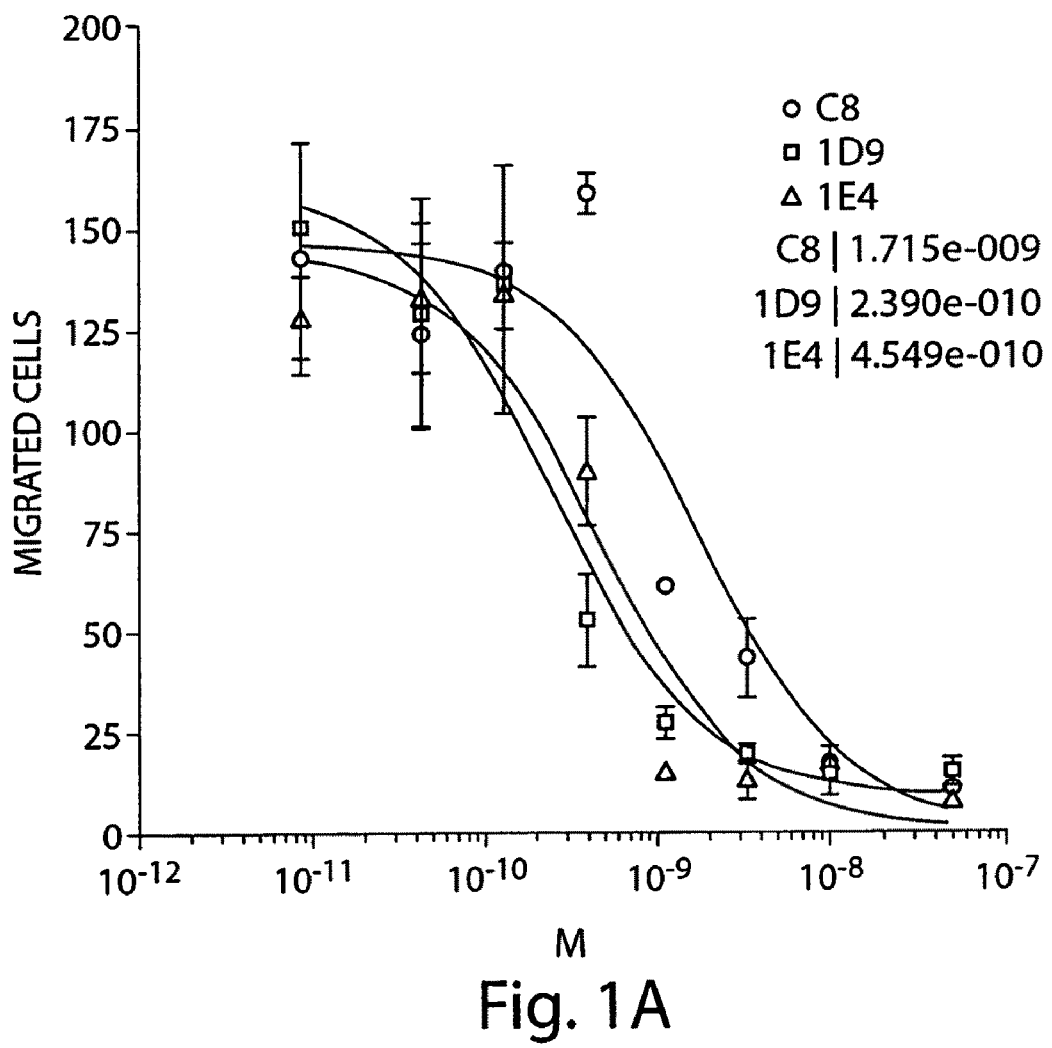
FIG. 1 is a series of graphs depicting the activity of anti-huRANTES antibodies in chemotaxis assays using L1.2 cells transfected with hCCR5 and 1 nM or 0.2 nM of recombinant human RANTES (FIGS. 1A and B respectively) as well as native human RANTES (FIG. 1C).

The present invention provides fully human monoclonal antibodies specific for the chemokine Regulated upon Activation, Normal T-cell Expressed, and Secreted (RANTES, CCL5). The terms "RANTES" and "CCL5" are used interchangeably herein. The antibodies are collectively referred to herein as huRANTES antibodies. The huRANTES antibodies specifically bind RANTES. As used herein, the terms "specific for", "specific binding", "directed against" (and all grammatical variations thereof) are used interchangeably in the context of antibodies that recognize and bind to a RANTES epitope when the equilibrium binding constant ($K_d$) is $\leq 1$ µM, e.g., $\leq 100$ nM, preferably $\leq 10$ nM, and more preferably $\leq 1$ nM. For example, the huRANTES antibodies provided herein exhibit a $K_d$ in the range approximately between $\leq 10$ nM to about 100 µM.

The huRANTES antibodies are, for example, RANTES antagonists or inhibitors that modulate at least one biological activity of RANTES. Biological activities of RANTES include, for example, binding a RANTES receptor such as, for example, CCR1, CCR3, CCR4, and/or CCR5; chemoattraction of eosinophils, monocytes, and lymphocytes; binding of RANTES to glycosaminoglycans as well as RANTES oligomerization. For example, the huRANTES antibodies completely or partially inhibit RANTES activity by partially or completely blocking the binding of RANTES to a RANTES receptor (e.g., CCR1, CCR3, CCR4, and/or CCR5). The RANTES antibodies are considered to completely inhibit RANTES activity when the level of RANTES activity in the presence of the huRANTES antibody is decreased by at least 95%, e.g., by 96%, 97%, 98%, 99% or 100% as compared to the level of RANTES activity in the absence of binding with a huRANTES antibody described herein. The RANTES antibodies are considered to partially inhibit RANTES activity when the level of RANTES activity in the presence of the huRANTES antibody is decreased by less than 95%, e.g., 10%, 20%, 25%, 30%, 40%, 50%, 60%, 75%, 80%, 85% or 90% as compared to the level of RANTES activity in the absence of binding with a huRANTES antibody described herein.

The huRANTES antibodies of the invention are produced by immunizing an animal with RANTES, such as, for example, murine or human RANTES or an immunogenic fragment, derivative or variant thereof. Alternatively, the animal is immunized with cells transfected with a vector containing a nucleic acid molecule encoding RANTES, such that RANTES is expressed and associated with the surface of the transfected cells. Alternatively, the antibodies are obtained by screening a library that contains antibody or antigen binding domain sequences for binding to RANTES. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

huRANTES antibodies of the invention include, for example, the heavy chain complementarity determining regions (CDRs) shown below in Table 2, the light chain CDRs shown in Table 3, and combinations thereof.

| Clone ID | Heavy CDR1 | Heavy CDR2 | Heavy CDR3 |
|---|---|---|---|
| CG11 | DYYIH (SEQ NO: 74) | LIDPKDGEIQYAEKFQA (SEQ NO: 75) | EVLSGIRVFPFDP (SEQ NO: 76) |
| BG11 | ELSMH (SEQ NO: 90) | GFDPEDGETIYAQKFQG (SEQ NO: 91) | YSGSSGWWAFDI (SEQ NO: 92) |
| A9 | SYAMS (SEQ NO: 106) | AISGSGGSTYYADSVKG (SEQ NO: 107) | DLGYCTNGVCWGIDY (SEQ NO: 108) |
| E6 | EIAIH (SEQ NO: 122) | SFEPEDAEAIYAQRFQG (SEQ NO: 123) | DPYYASSGSNYMEV (SEQ NO: 124) |
| H6 | KQSMH (SEQ NO: 138) | SSNPEDDETLYAKKFQG (SEQ NO: 139) | DSQGFYYYYGMDV (SEQ NO: 140) |
| G2 | ELSIH (SEQ NO: 154) | GFDPEDGETIYAQNFQG (SEQ NO: 155) | DLTGSRDS (SEQ NO: 156) |
| E10 | SYAMH (SEQ NO: 28) | VISYDGSNKYYADSVKG (SEQ NO: 29) | ETFPHYYYYMDV (SEQ NO: 30) |
| C10 | SYAMS (SEQ NO: 106) | AISGSGGSTYYADSVKG (SEQ NO: 107) | VRGSSQYDFWSGSEFDY (SEQ NO: 188) |
| 2D1 | DFAMH (SEQ NO: 44) | GYVPEDGDTIYAQKFQG (SEQ NO: 45) | DPLYSGSLSY (SEQ NO: 64) |
| A5 | ELSIH (SEQ NO: 154) | YIDPEDGEPIYAQKFQG (SEQ NO: 207) | VTGSTSDAFDL (SEQ NO: 208) |
| H11 | NYALS (SEQ NO: 222) | GFIPLVDTTNYAQRFQG (SEQ NO: 223) | EQVAVGPGPTSDRGPDGLDV (SEQ NO: 224) |
| D1 | DYYIH (SEQ NO: 74) | LVDSEEDGETLFAETFRG (SEQ NO: 239) | EYGEYGFFQS (SEQ NO: 240) |
| E7 | NYALS (SEQ NO: 222) | AVIPLVETTSYAQRFQG (SEQ NO: 255) | EQVAVGPGPTSNRGPDGLDV (SEQ NO: 169) |
| C8 | SYAMH (SEQ NO: 28) | VISYDGSNKYYADSVKG (SEQ NO: 29) | ETFPHYYYYMDV (SEQ NO: 30) |
| 1D9 | EFAMH (SEQ NO: 8) | GFVPEDGETIYAQKFQG (SEQ NO: 9) | DPLYTPGLEP (SEQ NO: 10) |
| 1E4 | EFAMH (SEQ NO: 8) | GFVPEDGETIYAQKFQG (SEQ NO: 9) | DPLYEGSFSV (SEQ NO: 20) |
| 3E7 | DFAMH (SEQ NO: 44) | GYVPEDGDTIYAQKFQG (SEQ NO: 45) | DPLYPPGLSP (SEQ NO: 46) |
| 4D8 | DFAMH (SEQ NO: 44) | GYVPEDGDTIYAQKFQG (SEQ NO: 45) | DPLYTPGLYV (SEQ NO: 50) |
| 5E1 | DFAMH (SEQ NO: 44) | GYVPEDGDTIYAQKFQG (SEQ NO: 45) | DYLYTPSLSY (SEQ NO: 54) |

-continued

| Clone ID | Heavy CDR1 | Heavy CDR2 | Heavy CDR3 |
|---|---|---|---|
| 6A8 | DFAMH (SEQ NO: 44) | GYVPEDGDTIYAQKFQG (SEQ NO: 45) | DPLYPPGLQP (SEQ NO: 58) |
| 7B5 | DFAMH (SEQ NO: 44) | GYVPEDGDTIYAQKFQG (SEQ NO: 45) | DPLYSGSLSY (SEQ NO: 64) |

-continued

| Clone ID | Light CDR1 | Light CDR2 | Light CDR3 |
|---|---|---|---|
| CG11 | TGSSSNIGAGYDVY (SEQ NO: 77) | DTNNRPP (SEQ NO: 81) | QSYDIALSNSNVV (SEQ NO: 82) |
| BG11 | QGDSLRSYYAS (SEQ NO: 96) | GKNNRPS (SEQ NO: 97) | QTWGTGIWV (SEQ NO: 98) |
| A9 | TRSSGSIADNYVQ (SEQ NO: 112) | DDDQRLS (SEQ NO: 113) | QSYDDSNDV (SEQ NO: 114) |
| E6 | TGSGGSISSNYVQ (SEQ NO: 128) | EDDQRPS (SEQ NO: 129) | HSYDGNNRWV (SEQ NO: 130) |
| H6 | TGSSSNIGADYDVH (SEQ NO: 144) | DNINRPS (SEQ NO: 145) | QSYDSSLSGVL (SEQ NO: 146) |
| G2 | TGSRSDIGYYNYVS (SEQ NO: 160) | DVTERPS (SEQ NO: 161) | SSFSSGDTFVV (SEQ NO: 162) |
| E10 | GGGNFDDEGVH (SEQ NO: 176) | DDTGRPS (SEQ NO: 177) | QAWDSSNDHPV (SEQ NO: 178) |
| C10 | GGDNIGGQNVH (SEQ NO: 192) | YDTDRPS (SEQ NO: 193) | QVWDVDSDHPWV (SEQ NO: 194) |
| 2D1 | GGNNIESKSVH (SEQ NO: 14) | DDSDRPS (SEQ NO: 15) | QVWDSNTDHWV (SEQ NO: 16) |
| A5 | GGANLWGLGVH (SEQ NO: 212) | DNSDPAS (SEQ NO: 213) | QVWDSSSDHWV (SEQ NO: 214) |
| H11 | TGSNSNLGADYDVH (SEQ NO: 228) | DNNIRPS (SEQ NO: 229) | QSYDTGLTSSDVI (SEQ NO: 230) |
| D1 | TGSSSNIGADYDVN (SEQ NO: 244) | GDINRPS (SEQ NO: 245) | QSFDNSLSGSVI (SEQ NO: 246) |
| E7 | TGSSSNIGDGYDVH (SEQ NO: 190) | GNSNRPS (SEQ NO: 191) | GTWDDILNGWV (SEQ NO: 235) |
| C8 | EGDDTDIGTVN (SEQ NO: 34) | EDGYRPS (SEQ NO: 35) | QFWDVDSDHPV (SEQ NO: 36) |
| 1D9 | GGNNIESKSVH (SEQ NO: 14) | DDSDRPS (SEQ NO: 15) | QVWDSNTDHWV (SEQ NO: 16) |
| 1E4 | GGNNIESKSVH (SEQ NO: 14) | DDSDRPS (SEQ NO: 15) | QVWDSNTDHWV (SEQ NO: 16) |
| 3E7 | GGNNIESKSVH (SEQ NO: 14) | DDSDRPS (SEQ NO: 15) | QVWDSNTDHWV (SEQ NO: 16) |
| 4D8 | GGNNIESKSVH (SEQ NO: 14) | DDSDRPS (SEQ NO: 15) | QVWDSNTDHWV (SEQ NO: 16) |
| 5E1 | GGNNIESKSVH (SEQ NO: 14) | DDSDRPS (SEQ NO: 15) | QVWDSNTDHWV (SEQ NO: 16) |
| 6A8 | GGNNIESKSVH (SEQ NO: 14) | DDSDRPS (SEQ NO: 15) | QVWDSNTDHWV (SEQ NO: 16) |
| 7B5 | GGNNIESKSVH (SEQ NO: 14) | DDSDRPS (SEQ NO: 15) | QVWDSGPVWWI (SEQ NO: 66) |

An exemplary huRANTES monoclonal antibody is the 1D9 antibody described herein. As shown below, the 1D9 antibody includes a heavy chain variable region (SEQ ID NO:2) encoded by the nucleic acid sequence shown in SEQ ID NO:1, and a light chain variable region (SEQ ID NO:4) encoded by the nucleic acid sequence shown in SEQ ID NO:3. The CDR sequences are shown in boxes.

> 1D9 Heavy chain variable domain nucleic acid sequence (SEQ ID NO: 1):

```
CAGGTGCAGCTGGTGCAGTCTGGGGCTGAGGTGAAGAAGCCTGGGGCCTCAGTGAAGGTTTCC
TGCAAGGTTTCCGGATACACCCTCACTGAGTTCGCCATGCACTGGGTGCGACAGGCTCCTGGA
AAAGGGCTTGAGTGGATGGGAGGTTTTGTTCCTGAAGATGGTGAGACAATCTACGCGCAGAAG
TTCCAGGGCAGAGTCACCATGACCGAGGACACATCTACAGACACAGCCTACATGGAGCTGAGC
AGCCTGAGATCTGAGGCACGGCCGTGTATTACTGTGCAACAGATCCCCTGTATACTCCGGGT
CTTGAGCCTTGGGGGCAGGGGACCACGGTCACCGTCTCGAGT
```

> 1D9 Heavy chain variable domain amino acid sequence (SEQ ID NO: 2)

```
QVQLVQSGAEVKKPGASVKVSCKVSGYTLTEFAMHWVRQAPGKGLEWMGGFVPEDGETIYAQK
FQGRVTMTEDTSTDTAYMELSSLRSEDTAVYYCATDPLYTPGLEPWGQGTTVTVSS
```

>D9 Light chain variable domain nucleic acid sequence (SEQ ID NO: 3):

```
TCCTATGTCGCTGACTCAGCCACCCTCGGTGTCAGTGGCCCCAGGACAGACGGCCAGGATTAACC
TGTGGGGAAACAACATTGAAAGTAAAAGTGTGCACTGGTACCAGCAGAAGCCAGGCCAGGCC
CCTGTGCTGGTGGTCTATGATGATAGCGACCGGCCCTCAGGGATCCCTGAGCGATTCTCTGGC
TCCAACTCTGGGAACACGGCCACCCTGACCATCAGCAGGGTCGAAGCCGGGGATGAGGCCGAC
TATTACTGTCAGGTGTGGGATAGTAATACTGATCATTGGGTGTTCGGCGGAGGGACCAAGCTC
ACCGTCCTA
```

>1 D9 Light chain variable domain amino acid sequence (SEQ ID NO: 4)

```
SYVLTQPPSVSVAPGQTARITCGGNNIESKSVHWYQQKPGQAPVLVVYDDSDRPSGIPERFSG
SNSGNTATLTISRVEAGDEADYYCQVWDSNTDHWVFGGGTKLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 1D9 antibody have the following sequences: EFAMH (SEQ ID NO:8), encoded by the nucleic acid sequence GAGTTCGCCATGCAC (SEQ ID NO: 5); GFVPEDGETIYAQKFQG (SEQ ID NO:9), encoded by the nucleic acid sequence GGTTTTGTTCCTGAAGATGGTGAGACAATCTACGCGCAGAAGTTCCAGGGC (SEQ ID NO: 6); and DPLYTPGLEP (SEQ ID NO:10), encoded by the nucleic acid sequence GATCCCCTGTATACTCCGGGTCTTGAGCCT (SEQ ID NO: 7). The light chain CDRs of the 1D9 antibody have the following sequences: GGNNIESKSVH (SEQ ID NO:14), encoded by the nucleic acid sequence GGGGGAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSNTDHWV (SEQ ID NO: 16), encoded by the nucleic acid sequence CAGGTGTGGGATAGTAATACTGATCATTGGGTG (SEQ ID NO: 13).

An exemplary huRANTES monoclonal antibody is the 1E4 antibody described herein. As shown below, the 1E4 antibody includes a heavy chain variable region (SEQ ID NO: 18) encoded by the nucleic acid sequence shown in SEQ ID NO:17, and a light chain variable region (SEQ ID NO: 4) encoded by the nucleic acid sequence shown in SEQ ID NO:3. The CDR sequences are shown in boxes.

A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 1E4 antibody have the following sequences: EFAMH (SEQ ID NO:8), encoded by the nucleic acid sequence GAGTTCGCCATGCAC (SEQ ID NO: 5); GFVPEDGETIYAQKFQG (SEQ ID NO:9), encoded by the nucleic acid sequence GGTTTTGTTCCTGAAGATGGTGAGACAATCTACGCGCAGAAGTTCCAGGGC (SEQ ID NO: 6); and DPLYEGSFSV (SEQ ID NO:20), encoded by the nucleic acid sequence GATCCCCTGTATGAGGGTCCGTTTTCTGTT (SEQ ID NO: 19). The light chain CDRs of the 1E4 antibody have the following sequences: GGNNIESKSVH (SEQ ID NO:14), encoded by the nucleic acid sequence GGGGGAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSNTDHWV (SEQ ID NO:16), encoded by the nucleic acid sequence CAGGTGTGGGATAGTAATACTGATCATTGGGTG (SEQ ID NO: 13).

An exemplary huRANTES monoclonal antibody is the C8 antibody described herein. As shown below, the C8 antibody includes a heavy chain variable region (SEQ ID NO:22) encoded by the nucleic acid sequence shown in SEQ ID NO: 21, and a light chain variable region (SEQ ID NO:24)

>1E4 Heavy Chain variable domain nucleic acid sequence (SEQ ID NO: 17):

```
CAGGTGCAGCTGGTGCAGTCTGGGGCTGAGGTGAAGAAGCCTGGGGCCTCAGTGAAGGTTTCC
TGCAAGGTTTCCGGATACACCCTCACTGAGTTCGCCATGCACTGGGTGCGACAGGCTCCTGGA
AAAGGGCTTGAGTGGATGGGAGGTTTTGTTCCTGAAGATGGTGAGACAATCTACGCGCAGAAG
TTCCAGGGCAGAGTCACCTGACCGAGGACACATCTACAGACACAGCCTACATGGAGCTGAGC
AGCCTGAGATCTGAGGACACGGCCGTGTATTACTGTGCAACAGATCCCCTGTATGAGGGTTCG
TTTTCTGTTGGGGGCAGGGGACCACGGTCACCGTCTCGAGT
```

>1E4 Heavy chain variable domain amino acid sequence (SEQ ID NO: 18)

```
QVQLVQSGAEVKKPGASVKVSCKVSGYTLTEFAMHWVRQAPGKGLEWMGGFVPEDGETIYAQK
FQGRVTMTEDTSTDTAYMELSSLRSEDTABYYCATDPLYEGSFSVWGQGTTVTVSS
```

>1E4 Light chain nucleic acid sequence (SEQ ID NO: 3):

```
TCCTATGTGCTGACTCAGCCACCCTCGGTGTCAGTGGCCCCAGGACAGACGGCCAGGATTACC
TGTGGGGGAAACAACATTGAAAGTAAAAGTGTGCACTGGTACCAGCAGAAGCCAGGCCAGGCC
CCTGTGCTGGTGGTCTATGATGATAGCGACCGGCCCTCAGGGGATCCCTGAGCGATTCTTGGC
TCCAACTCTGGGAACACGGCCACCCTGACCATCAGCAGGGTCGAAGCCGGGGATGAGGCCGAC
TATTACTGTCAGGTGTGGGATAGTAATACTGATCATTGGGTGTTCGGCGGAGGGACCAAGCTC
ACCGTCCTA
```

>1E4 Light chain variable domain amino acid sequence (SEQ ID NO: 4)

```
SYVLTQPPSVSVAPGQTARITCGGNNIESKSVHWYQQKPGQAPVLVVYDDSDRPSGIPERFSG
SNSGNTATLTISRVEAGDEADYYCQVWDSNTDHWVFGGGTKLTVL
```

The amino acids encompassing the complementarity determining regions (CDR) are as defined by Chothia et al. and E.

encoded by the nucleic acid sequence shown in SEQ ID NO: 23. The CDR sequences are shown in boxes.

> C8 Heavy chain variable domain nucleic acid sequence (SEQ ID NO: 21)

```
CAGGTGCAGCTGGTGGAGTCTGGGGGAGGCGTGGTCCAGCCTGGGAGGTCCCTGAGACTCTCC
TGTGCAGCCTCTGGATTCACCTTCAGTAGCTATGCTATGCACTGGGTCCGCCAGGCTCCAGGC
AAGGGGCTAGAGTGGGTGGCAGTTATATCATATGATGGAAGTAATAAATACTACGCAGACTCC
GTGAAGGGCCGATTCACCATCTCCAGAGACAATTCCAAGAACACGCTGTATCTGCAAATGAAC
AGCCTGAGAGCTGAGGACACGGCTGTGTATTACTGTGCGAGAGAAACTTTCCCCCACTACTAC
TACTACTACATGGACGTCTGGGGCCGGGGCACCCTGGTCACCGTCTCGAGT
```

> C8 Heavy chain variable domain amino acid sequence (SEQ ID NO: 22)

```
QVQLVESGGGVVQPGRSLRLSCAASGFTFSSYAMHWVRQAPGKGLEWVAVISYDGSNKYYADS
VKGRFTISRDNSKNTLYLQMNSLRAEDTAVYYCARETFPHYYYYMDVWGRGTLVTVSS
```

> C8 Light chain variable domain nucleic acid sequence (SEQ ID NO: 23):

```
TCCTATGTGCTGACTCAGCCCCCCTCGGTGTCAGTGGCCCCAGGGCAGACGGCCCGCATTACC
TGTGAGGGAGACGACACTGACATTGGTACTGTCAACTGGTACCAGCAGAAACCAGGCCAGGCC
CCTGTGTTGGTCATTAGTGAGGATGGCTACCGGCCCTCAGGGATCCCTGAACGATTCTCTGGC
TCCAACTCTGGGAACACGGCCACCCTTACCATCTCCAGGGTCGAGGCCGGGGATGAGGCCGAC
TATTACTGTCAGTTCTGGGATGTTGACAGTGATCATCCGGTTTTCGGCGGAGGGACCCAGCTC
ACCGTCCTA
```

> C8 Light chain variable domain amino acid sequence (SEQ ID NO: 24)

```
SYVLTQPPSVSVAPGQTARITCEGDDTDIGTVNWYQQKPGQAPVLVISEDGYRPSGIPERFSG
SNSGNTATLTISRVEAGDEADYYCQFWDVDSDHPVFGGGTQLTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the C8 antibody have the following sequences: SYAMH (SEQ ID NO:28), encoded by the nucleic acid sequence AGCTATGCTATGCAC (SEQ ID NO: 25); VISYDGSNKYYADSVKG (SEQ ID NO:29), encoded by the nucleic acid sequence GTTATATCATATGATGGAAGTAATAAATACTACGCAGACTCCGTGAAGGGC (SEQ ID NO: 26); and ETFPHYYYYMDV (SEQ ID NO:30), encoded by the nucleic acid sequence GAAACTTTCCCCCACTACTACTACTACTACATGGACGTC (SEQ ID NO: 27). The light chain CDRs of the C8 antibody have the following sequences: EGDDTDIGTVN (SEQ ID NO:34), encoded by the nucleic acid sequence GAGGGAGACGACACTGACATTGGTACTGTCAAC (SEQ ID NO:31); EDGYRPS (SEQ ID NO:35), encoded by the nucleic acid sequence GAGGATGGCTACCGGCCCTCA (SEQ ID NO: 32); and QFWDVDSDHPV (SEQ ID NO:36), encoded by the nucleic acid sequence CAGTTCTGGGATGTTGACAGTGATCATCCGGTT (SEQ ID NO: 33).

An exemplary huRANTES monoclonal antibody is the 3E7 antibody described herein. As shown below, the 3E7 antibody includes a heavy chain variable region (SEQ ID NO:38) encoded by the nucleic acid sequence shown in SEQ ID NO: 37, and a light chain variable region (SEQ ID NO:40) encoded by the nucleic acid sequence shown in SEQ ID NO: 39. The CDR sequences are shown in boxes.

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 3E7 antibody have the following sequences: DFAMH (SEQ ID NO:44), encoded by the nucleic acid sequence GACTTCGCCATGCAC (SEQ ID NO: 41); GYVPEDGDTIYAQKFQG (SEQ ID NO:45), encoded by the nucleic acid sequence GGTTATGTTCCTGAAGATGGTGACACAATCTACGCGCAGAAGTTCCAGGGC (SEQ ID NO: 42); and DPLYPPGLSP (SEQ ID NO:46), encoded by the nucleic acid sequence GATCCCCTGTATCCGCCTGGGCTGTCTCCT (SEQ ID NO: 43). The light chain CDRs of the 3E7 antibody have the following sequences: GGNNIESKSVH (SEQ ID NO:14), encoded by the nucleic acid sequence GGGGGAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSNTDHWV (SEQ ID NO:16), encoded by the nucleic acid sequence CAGGTGTGGGATAGTAATACTGATCATTGGGTG (SEQ ID NO: 13).

An exemplary huRANTES monoclonal antibody is the 4D8 antibody described herein. As shown below, the 4D8 antibody includes a heavy chain variable region (SEQ ID NO:48) encoded by the nucleic acid sequence shown in SEQ ID NO: 47, and a light chain variable region (SEQ ID NO:40) encoded by the nucleic acid sequence shown in SEQ ID NO: 39. The CDR sequences are shown in boxes.

> 3E7 Heavy chain variable domain nucleic acid sequence (SEQ ID NO: 37)

```
CAGGTGCAGCTGGTGCAGTCTGGGGCTGAGGTGAAGAAGCCTGGGGCCTCAGTGAAGGTT
TCCTGCAAGGTTTCCGGATACACCCTCAATGACTTCGCCATGCACTGGGTGCGACAGGCT
CCTGGAAAAGGGCTTGAGTGGATGGGAGGTTATGTTCCTGAAGATGGTGACACAATCTAC
GCGCAGAAGTTCCAGGGCAGAGTCACCATGACCGAGGACACATCTACAGACACAGCCTAC
ATTGGAGCTGAGCAGCCTGAGATCTGAGGACACGCCGGTGTATTACTGTGCAACAGATCCC
CTGTATCCGCCTGGGCTGTCTCCTTGGGGGCAGGGGACCACGGTCACCGTCTCGAGT
```

> 3E7 Heavy chain variable domain amino acid sequence (SEQ ID NO: 38)

```
QVQLVQSGAEVKKPGASVKVSCKVSGYTLNDFAMHWVRQAPGKGLEWMGGYVPEDGDTIY
AQKFQGRVTMTEDTSTDTAYMELSSLRSEDTAVYYCATDPLYPPGLSPWGQGTTVTVSS
```

> 3E7 Light chain variable domain nucleic acid sequence (SEQ ID NO: 39):

```
TCCTATGTGCTGACTCAGCCACCCTCGGTGTCAGTGGCCCCAGGACAGACGGCCAGGATT
ACCTGTGGGGGAAACAACATTGAAAGTAAAAGTGTGCACTGGTACCAGCAGAAGCCAGGC
CAGGCCCCTGTGCTGGTGGTCTATGATGATAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGATAGTAATACTGATCATTGGGTGTTCGGC
GGAGGGACCAAGGTCACCGTCCTA
```

> 3E7 Light chain variable domain amino acid sequence (SEQ ID NO: 40)

```
SYVLTQPPSVSVAPGQTARITCGGNNIESKSVHWYQQKPGQAPVLVVYDDSDRPSGIPER
FSGSNSGNTATLTISRVEAGDEADYYCQVWDSNTDHWVFGGGTKVTVL
```

> 4D8 Heavy chain variable domain nucleic acid sequence (SEQ ID NO: 47)

```
CAGGTGCAGCTGGTGCAGTCTGGGGCTGAGGTGAAGAAGCCTGGGCCTCAGTGAAGGTT
TCCTGCAAGGTTTCCGGATACACCCTCAATGACTTCGCCATGCACTGGGTGCGACAGGCT
CCTGGAAAAGGGCTTGAGTGGATGGGAGGTTATGTTCCTGAAGATGGTGACACAATCTAC
GCGCAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAACAGATCCC
CTGTATACGCCTGGTCTGTATGTGTGGGGGCAGGGGACCACGGTCACCGTCTCGAGT
```

> 4D8 Heavy chain variable domain amino acid sequence (SEQ ID NO: 48)

```
QVQLVQSGAEVKKPGASVKVSCKVSGYTLNDFAMHWVRQAPGKGLEWMGGYVPEDGDTIY
AQKFQGRVTMTEDTSTDTAYMELSSLRSEDTAVYYCATDPLYTPGLYVWGQGTTVTVSS
```

> 4D8 Light chain variable domain nucleic acid sequence (SEQ ID NO: 39):

```
TCCTATGTGCTGACTCAGCCACCCTCGGTGTCAGTGGCCCCAGGACAGACGGCAGGATT
ACCTGTGGGGGAAACAACATTGAAAGTAAAAGTGTGCACTGGTACCAGCAGAAGCCAGGC
CAGGCCCCTGTGCTGGTGGTCTATGATGATAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGGATAGTAATACTGATCATTGGGTGTTCGGC
GGAGGGACCAAGGTCACCGTCCTA
```

> 4D8 Light chain variable domain amino acid sequence (SEQ ID NO: 40)

```
SYVLTQPPSVSVAPGQTARITCGGNNIESKSVHWYQQKPGQAPVLVVYDDSDRPSGIPER
FSGSNSGNTATLTISRVEAGDEADYYCQVWDSNTDHWVFGGGTKVTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 4D8 antibody have the following sequences: DFAMH (SEQ ID NO:44), encoded by the nucleic acid sequence GACTTCGCCATGCAC (SEQ ID NO: 41); GYVPEDGDTIYAQKFQG (SEQ ID NO:45), encoded by the nucleic acid sequence GGTTATGTTCCTGAAGATGGTGACACAATCTACGCGCAGAAGTTCCAGGGC (SEQ ID NO: 42); and DPLYTPGLYV (SEQ ID NO:50), encoded by the nucleic acid sequence GATCCCCTGTATACGCCTGGTCTGTATGTG (SEQ ID NO: 49). The light chain CDRs of the 4D8 antibody have the following sequences: GGNNIESKSVH (SEQ ID NO:14), encoded by the nucleic acid sequence GGGGGAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSNTDHWV (SEQ ID NO:16), encoded by the nucleic acid sequence CAGGTGTGGGATAGTAATACTGATCATTGGGTG (SEQ ID NO: 13).

An exemplary huRANTES monoclonal antibody is the 5E1 antibody described herein. As shown below, the 5E1 antibody includes a heavy chain variable region (SEQ ID NO:52) encoded by the nucleic acid sequence shown in SEQ ID NO: 51, and a light chain variable region (SEQ ID NO:40) encoded by the nucleic acid sequence shown in SEQ ID NO: 39. The CDR sequences are shown in boxes.

> 5E1 Heavy chain variable domain nucleic acid sequence (SEQ ID NO: 51)

```
CAGGTGCAGCTGGTGCAGTCTGGGGCTGAGGTGAAGAAGCCTGGGGCCTCAGTGAAGTT
TCCTGCAAGGTTTCCGGATACACCCTCAATGACTTCGCCATGCACTGGGTGCGACAGGCT
CCTGGAAAAGGGCTTGAGTGGATGGGAGGTTATGTTCCTGAAGATGGTGACACAATCTAC
GCGCAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAGATTAT
TTGTATATTCCTAGCTTATCCTACTGGGGCCAGGGGACCACGGTCACCGTCTCGAGT
```

> 5E1 Heavy chain variable domain amino acid sequence (SEQ ID NO: 52)

```
QVQLVQSGAEVKKPGASVKVSCKVSGYTLNDFAMHWVRQAPGKGLEWMGGYVPEDGDTIY
AQKFQGRVTMTEDTSTDTAYMELSSLRSEDTAVYYCATDYLYIPSLSYWGQGTTVTVSS
```

> 5E1 Light chain variable domain nucleic acid sequence (SEQ ID NO: 39):

```
TCCTATGTGCTGACTCAGCCACCCTCGGTGTCAGTGGCCCCAGGACAGACGGCCAGGATT
ACCTGTGGGGGAAACAACATTGAAAGTAAAAGTGTGCACTGGTACCAGCAGAAGCCAGGC
CAGGCCCCTGTGCTGGTGGTCTATGATGATAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGGATAGTAATACTGATCATTGGGTGTTCGGC
GGAGGGACCAAGGTCACCGTCCTA
```

> 5E1 Light chain variable domain amino acid sequence (SEQ ID NO: 40)

```
SYVLTQPPSVSVAPGQTARITCGGNNIESKSVHWYQQKPGQAPVLVVYDDSDRPSGIPER
FSGSNSGNTATLTISRVEAGDEADYYCQVWDSNTDHWVFGGGTKVTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 5E1 antibody have the following sequences: DFAMH (SEQ ID NO:44), encoded by the nucleic acid sequence GACTTCGCCATGCAC (SEQ ID NO: 41); GYVPEDGDTIYAQKFQG (SEQ ID NO:45), encoded by the nucleic acid sequence GGTTATGTTCCTGAAGATGGTGACACAATCTACGCGCAGAAGTTCCAGGGC (SEQ ID NO: 42); and DYLYIPSLSY (SEQ ID NO:54), encoded by the nucleic acid sequence GATTATTTGTATATTCCTAGCTTATCCTAC (SEQ ID NO: 53). The light chain CDRs of the 5E1 antibody have the following sequences: GGNNIESKSVH (SEQ ID NO:14), encoded by the nucleic acid sequence GGGGGAAACAACAT-TGAAAGTAAAAGTGTGCAC (SEQ ID NO:11); DDS-DRPS (SEQ ID NO:15), encoded by the nucleic acid sequence GATGATAGCGACCGGCCCTCA (SEQ ID NO: 12); and QVWDSNTDHWV (SEQ ID NO:16), encoded by the nucleic acid sequence CAGGTGTGGGATAG-TAATACTGATCATTGGGTG (SEQ ID NO: 13).

An exemplary huRANTES monoclonal antibody is the 6A8 antibody described herein. As shown below, the 6A8 antibody includes a heavy chain variable region (SEQ ID NO:56) encoded by the nucleic acid sequence shown in SEQ ID NO: 55, and a light chain variable region (SEQ ID NO:40) encoded by the nucleic acid sequence shown in SEQ ID NO: 39. The CDR sequences are shown in boxes.

nucleic acid sequence GACTTCGCCATGCAC (SEQ ID NO: 41); GYVPEDGDTIYAQKFQG (SEQ ID NO:45), encoded by the nucleic acid sequence GGTTATGTTCCT-GAAGATGGTGACACAATCTACGCGCA-GAAGTTCCAGGGC (SEQ ID NO: 42); and DPLYP-PGLQP (SEQ ID NO:58), encoded by the nucleic acid sequence GATCCCCTGTATCCTCCGGGGCTGCAGCCT (SEQ ID NO: 57). The light chain CDRs of the 6A8 antibody have the following sequences: GGNNIESKSVH (SEQ ID NO:14), encoded by the nucleic acid sequence GGGG-GAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSNTDHWV (SEQ ID NO:16), > 6A8 Heavy chain variable domain nucleic acid sequence (SEQ ID NO: 55)

```
CAGGTGCAGCTGGTGCAGTCTGGGGCTGAGGTGAAGAAGCCTGGGGCCTCAGTGAAGGTT
TCCTGCAAGGTTTCCGGATACACCCTCAATGACTTCGCCATGCACTGGGTGCGACAGGCT
CCTGGAAAAGGGCTTGAGTGGATGGGAGGTTATGTTCCTGAAGATGGTGACACAATCTAC
GCGCAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAACAGATCCC
CTGTATCCTCCGGGGCTGCAGCCTTGGGGGCAGGGGACCACGGTCACCGTCTCGAGT
```

> 6A8 Heavy chain variable domain amino acid sequence (SEQ ID NO: 56)

```
QVQLVQSGAEVKKPGASVKVSCKVSGYTLNDFAMHWVRQAPGKGLEWMGGYVPEDGDTIY
AQKFQGRVTMTEDTSTDTAYMELSSLRSEDTAVYYCATDPLYPPGLQPWGQGTTVTVSS
```

> 6A8 Light chain variable domain nucleic acid sequence (SEQ ID NO: 39)

```
TCCTATGTGCTGACTCAGCCACCCTCGGTGTCAGTGGCCCCAGGACAGACGGCCAGGATT
ACCTGTGGGGGAAACAACATTGAAAGTAAAAGTGTGCACTGGTACCAGCAGAAGCCAGGC
CAGGCCCCTGTGCTGGTGGTCTATGATGATAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGGATAGTAATACTGATCATTGGGTGTTCGGC
GGAGGGACCAAGGTCACCGTCCTA
```

> 6A8 Light chain variable domain amino acid sequence (SEQ ID NO: 40)

```
SYVLTQPPSVSVAPGQTARITCGGNNIESKSVHWYQQKPGQAPVLVVYDDSDRPSGIPER
FSGSNSGNTATLTISRVEAGDEADYYCQVWDSNTDHWVFGGGTKVTVL
```

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the 6A8 antibody have the following sequences: DFAMH (SEQ ID NO:44), encoded by the encoded by the nucleic acid sequence CAGGTGTGGGAT-AGTAATACTGATCATTGGGTG (SEQ ID NO: 13).

An exemplary huRANTES monoclonal antibody is the 7B5 antibody described herein. As shown below, the 7B5 antibody includes a heavy chain variable region (SEQ ID NO:60) encoded by the nucleic acid sequence shown in SEQ ID NO: 59, and a light chain variable region (SEQ ID NO:62) encoded by the nucleic acid sequence shown in SEQ ID NO: 61. The CDR sequences are shown in boxes.

> 7B5 Heavy chain variable domain nucleic acid sequence (SEQ ID NO: 59)

```
CAGGTGCAGCTGGTGCAGTCTGGGGCTGAGGTGAAGAAGCCTGGGGCCTCAGTGAAGGTT
TCCTGCAAGGTTTCCGGATACACCCTCAATGACTTCGCCATGCACTGGGTGCGACAGGCT
CCTGGAAAAGGGCTTGAGTGGATGGGAGGTTATGTTCCTGAAGATGGTGACACAATCTAC
GCGCAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAACAGATCCC
CTGTATAGTGGGAGCTTATCCTACTGGGGCAGGGGACCACGGTCACCGTCTCGAGT
```

> 7B5 Heavy chain variable domain amino acid sequence (SEQ ID NO: 60)

```
QVQLVQSGAEVKKPGASVKVSCKVSGYTLNDFAMHWVRQAPGKGLEWMGGYVPEDGDTIY
AQKFQGRVTMTEDTSTDTAYMELSSLRSEDTAVYYCATDPLYSGSLSYWGQGTTVTVSS
```

> 7B5 Light chain variable domain nucleic acid sequence (SEQ ID NO: 61):

```
TCCTATGTGCTGACTCAGCCACCCTCGGTGTCAGTGGCCCCAGGACAGACGGCCAGGATT
ACCTGTGGGGGAAACAACATTGAAAGTAAAAGTGTGCACTGGTACCAGCAGAAGCCAGGC
CAGGCCCCTGTGCTGGCCGTCTATGATGATAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGGATAGTGGTCCTGTGTGGTGGATTTTCGGC
GGAGGGACCAAGGTCACCGTCCTA
```

> 7B5 Light chain variable domain amino acid sequence (SEQ ID NO: 62)

```
SYVLTQPPSVSVAPGQTARITCGGNNIESKSVHWYQQKPGQAPVLVVYDDSDRPSGIPER
FSGSNSGNTATLTISRVEAGDEADYYCQVWDSGPVWWIFGGGTKLTVL
```

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the 7B5 antibody have the following sequences: DFAMH (SEQ ID NO:44), encoded by the nucleic acid sequence GACTTCGCCATGCAC (SEQ ID NO: 41); GYVPEDGDTIYAQKFQG (SEQ ID NO:45), encoded by the nucleic acid sequence GGTTATGTTCCTGAAGATGGTGACACAATCTACGCGCAGAAGTTCCAGGGC (SEQ ID NO: 42); and DPLYSGSLSY (SEQ ID NO:64), encoded by the nucleic acid sequence GATCCCCTGTATAGTGGGAGCTTATCCTAC (SEQ ID NO: 63). The light chain CDRs of the 7B5 antibody have the following sequences: GGNNIESKSVH (SEQ ID NO:14), encoded by the nucleic acid sequence GGGGGAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSGPVWWI (SEQ ID NO:66), encoded by the nucleic acid sequence TCAGGTGTGGGATAGTGGTCCTGTGTGGTGGATT (SEQ ID NO: 65).

An exemplary huRANTES monoclonal antibody is the CG11 antibody described herein. As shown below, the CG11 antibody includes a heavy chain variable region (SEQ ID NO:68) encoded by the nucleic acid sequence shown in SEQ ID NO: 67, and a light chain variable region (SEQ ID NO:70) encoded by the nucleic acid sequence shown in SEQ ID NO: 69. The CDR sequences are shown in boxes.

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the CG11_antibody have the following sequences: DYYIH (SEQ ID NO:74), encoded by the nucleic acid sequence GACTACTACATACAC (SEQ ID NO: 71); LIDPKDGEIQYAEKFQA (SEQ ID NO:75), encoded by the nucleic acid sequence GGTTATGTTCCTGAAGATGGTGACACAATCTACGCGCAGAAGTTCCAGGGC (SEQ ID NO: 72); and EVLSGIRVFPFDP (SEQ ID NO:76), encoded by the nucleic acid sequence GAGGTTTTAAGCGGTATTAGGGTTTTCCCATTCGACCCC (SEQ ID NO: 73). The light chain CDRs of the CG11_antibody have the following sequences: TGSSSNIGAGYDVY (SEQ ID NO:77), encoded by the nucleic acid sequence ACTGGGAGCAGCTCCAACATCGGGGCAGGTTATGATGTATAT (SEQ ID NO:80); DTNNRPP (SEQ ID NO:81), encoded by the nucleic acid sequence GATACCAACAATCGACCCCCA (SEQ ID NO: 78); and QSYDIALSNSNVV (SEQ ID NO:82), encoded by the nucleic acid sequence CAGTCTTATGACATCGCCCTGAGTAACTCGAATGTGGTT (SEQ ID NO: 79).

An exemplary huRANTES monoclonal antibody is the BG11 antibody described herein. As shown below, the BG11 antibody includes a heavy chain variable region (SEQ ID NO:84) encoded by the nucleic acid sequence shown in SEQ ID NO: 83, and a light chain variable region (SEQ ID NO:86) encoded by the nucleic acid sequence shown in SEQ ID NO: 85. The CDR sequences are shown in boxes.

```
> CG11 Heavy chain variable domain nucleic acid sequence (SEQ ID NO: 67)

CAGGTGCAGCTGGTGCAGTCTGGGACTGAGGTGAAGAAGCCTGGGGCTACAGTGAATGTT
TCCTGCAAGATTTCCGGACACCTCTTCACCGACTACTACATACACTGGGTGCAACAGGCC
CCTGGAAAAGGGCTTGAGTGGGTGGGACTTATTGATCCTAAAGATGGTGAAATCCAATAC
GCAGAGAAATTCCAGGCCAGAGTCACCATTACAGCGGACACGTCCACAGACACAGTTTAC
ATGGAATTGAACAGCCTGAGATCTGAAGACACGGCCGTGTATTACTGTGCAACAGAGGTT
TTAAGCGGTATTAGGGTTTTCCCATTCGACCCCTGGGGCCAGGGCACCCTGGTCACCGTC
TCGAGT

> CG11 Heavy chain variable domain amino acid sequence (SEQ ID NO: 68)

QVQLVQSGTEVKKPGATVNVSCKISGHLFTDYYIHWVQQAPGKGLEWVGLIDPKDGEIQY
AEKFQARVTITADTSTDTVYMELNSLRSEDTAVYYCATEVLSGIRVFPFDPWGQGTLVTV
SS

> CG11 Light chain variable domain nucleic acid sequence (SEQ ID NO: 69):

CAGTCTGTGCTGACTCAGCCACCCTCAGTGTCTGGGGCCCCAGGGCAGAGGGTCACCATC
TCTTGCACTGGGAGCAGCTCCAACATCGGGGCAGGTTATGATGTATATTGGTACCAACAG
TTTCCAGGGAAAGCCCCCAAACTCCTCATCTATGATACCAACAATCGACCCCCAGGGGTC
CCTGATCGATTCTCTGGCTCCAAGTCTGGCACCTCAGCCTCCCTGGCCATCAGTGGGCTC
CAGACTGAAGATGAGGCTGATTATTACTGCCAGTCTTATGACATCGCCCTGAGTAACTCG
AATGTGGTTTTCGGCGGAGGGACCAAGCTGACCGTCCTA

> CG11 Light chain variable domain amino acid sequence (SEQ ID NO: 70)

QSVLTQPPSVSGAPGQRVTISCTGSSSNIGAGYDVYWYQQFPGKAPKLLIYDTNNRPPGV
PDRFSGSKSGTSAASLAISGLQTEDEADYYCQSYDIALSNSNVVFGGGTKLTVL
```

> BG11 Heavy chain variable domain nucleic acid sequence (SEQ ID NO: 83)

CAGGTGCAGCTGGTGCAGTCTGGGGCTGAGGTGAAGAAGCCTGGGGCCTCAGTGAAGGTC
TCCTGCAAGGTTTCCGGATACACCCTCACTGAATTATCCATGCACTGGGTGCGACAGGCT
CCTGGAAAAGGGCTTGAGTGGATGGGAGGTTTTGATCCTGAAGATGGTGAAACAATCTAC
GCACAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAACTTATTCT
GGTAGTAGTGGTTGGTGGGCTTTTGATATCTGGGGCCAAGGGACAATGGTCACCGTCTCG
AGT

> BG11 Heavy chain variable domain amino acid sequence (SEQ ID NO: 84)

QVQLVQSGAEVKKPGASVKVSCKVSGYTLTELSMHWVRQAPGKGLEWMGGFDPEDGETIY
AQKFQGRVTMTEDTSTDTATMELSSLRSEDTAVYYCATYSGSSGWWAFDIWGQGTMVTVS
S

> BG11 Light chain variable domain nucleic acid sequence (SEQ ID NO: 85):

TCTTCTGAGCTGACTCAGGACCCTGCTGTGTCTGTGGCCTTGGGACAGACAGTCAGGATC
ACATGCCAAGGAGACAGCCTCAGAAGCTATTATGCAAGCTGGTACCAGCAGAAGCCAGGA
CAGGCCCCTGTACTTGTCATCTATGGTAAAAACAACCGGCCCTCAGGGATCCCAGACCGA
TTCTCTGGCTCCAGCTCAGGAAACACAGCTTCCTTGACCATCACTGGGGCTCAGGCGGAA
GATGAGGCTGACTATTACTGTCAGACCTGGGGCACTGGCATTTGGGTGTTCGGCGGAGGG
ACCAAGCTGACCGTCCTA

> BG11 Light chain variable domain amino acid sequence (SEQ ID NO: 86)

SSELTQDPAVSVALGQTVRITCQGDSLRSYYASWYQQKPGQAPVLVIYGKNNRPSGIPDR
FSGSSSGNTASLTITGAQAEDEADYYCQTWGTGIWVFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the BG11_antibody have the following sequences: ELSMH (SEQ ID NO:90), encoded by the nucleic acid sequence GAATTATCCATGCAC (SEQ ID NO: 87); GFDPEDGETIYAQKFQG (SEQ ID NO:91), encoded by the nucleic acid sequence GGTTTTGATCCTGAAGATGGTGAAACAATCTACGCACAGAAGTTCCAGGGC (SEQ ID NO: 88); and YSGSSGWWAFDI (SEQ ID NO:92), encoded by the nucleic acid sequence TATTCTGGTAGTAGTGGTTGGTGGGCTTTTGATATC (SEQ ID NO: 89). The light chain CDRs of the BG11_antibody have the following sequences: QGDSLRSYYAS (SEQ ID NO:96), encoded by the nucleic acid sequence CAAGGAGACAGCCTCAGAAGCTATTATGCAAGC (SEQ ID NO:93); GKNNRPS (SEQ ID NO:97), encoded by the nucleic acid sequence GGTAAAAACAACCGGCCCTCA (SEQ ID NO: 94); and QTWGTGIWV (SEQ ID NO:98), encoded by the nucleic acid sequence CAGACCTGGGGCACTGGCATTTGGGTG (SEQ ID NO: 95).

An exemplary huRANTES monoclonal antibody is the A9 antibody described herein. As shown below, the A9 antibody includes a heavy chain variable region (SEQ ID NO:100) encoded by the nucleic acid sequence shown in SEQ ID NO: 99, and a light chain variable region (SEQ ID NO:102) encoded by the nucleic acid sequence shown in SEQ ID NO:101. The CDR sequences are shown in boxes.

> A9 Heavy chain variable domain nucleic acid sequence (SEQ ID NO: 99)

GAGGTGCAGCTGGTGGAGTCCGGGGGAGGCTTGGTACAGCCTGGGGGGTCCCTGAGACTC
TCCTGTGCSGCCTCTGGATTCACCTTTAGCAGCTATGCCATGAGCTGGGTCCGCCAGGCT
CCAGGGAAGGGGCTGGAGTGGGTCTCAGCTATTAGTGGTAGTGGTGGTAGCACATACTAC
GCAGACTCCGTGAAGGGCCGGTTCACCATCTCCAGAGACAATTCCAAGAACACGCTGTAT
CTGCAAATGAACAGCCTGAGAGCCGAGGACACGGCCGTGTATTACTGTGCGAGAGATTTA
GGATATTGTACTAATGGTGTATGCTGGGGTATTGACTACTGGGGCCAGGGGACAATGGTC
ACCGTCTCGAGT

> A9 Heavy chain variable domain amino acid sequence (SEQ ID NO: 100)

EVQLVESGGGLVQPGGSLRLSCAASGFTFSSYAMSWVRQAPGKGLEWVSAISGSGGSTYY
ADSVKGRFTISRDNSKNTLYLQMNSLRAEDTAVYYCARDLGYCTNGVCWGIDYWGQGTMV
TVSS

> A9 Light chain variable domain nucleic acid sequence (SEQ ID NO: 101):

AATTTTATGCTGACTCAGCCCCACTCTGTGTCGGAGTCTCCGGGGAAGACGGTAACCATC
TCCTGCACCCGCAGCAGTGGCAGCATTGCCGACAACTATGTGCAGTGGTACCAGCAGCGC
CCGGGCAGTGCCCCACCACTATCATCTATGACGATGACCAAAGACTCTCTGGGGTCCCT
GATCGATTCTCTGGCTCCATTGACACTTCCTCCAACTCTGCCTCCCTCTCCATCTCTGGA
CTGAGGACTGAGGACGAGGCTGATTACTACTGTCAGTCTTATGATGACTCCAATGATGTG
TTCGGCGGAGGGACCAAGCTGACCGTCCTA

> A9 Light chain variable domain amino acid sequence (SEQ ID NO: 102)

NFMLTQPHSVSESPGKTVTISCTRSSGSIADNYVQWYQQRPGSAPTTIIYDDDQRLSGVP
DRFSGSIDTSSNSASLSISGLRTEDEADYYCQSYDDSNDVFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the A9 antibody have the following sequences: SYAMS (SEQ ID NO:106), encoded by the nucleic acid sequence AGCTATGCCATGAGC (SEQ ID NO: 103); AISGSGGSTYYADSVKG (SEQ ID NO:107), encoded by the nucleic acid sequence GCTATTAGTGG-TAGTGGTGGTAGCACATACTACGCA-GACTCCGTGAAGGGC (SEQ ID NO: 104); and DLGYCTNGVCWGIDY (SEQ ID NO: 108), encoded by the nucleic acid sequence GATTTAGGATATTGTACTAATG-GTGTATGCTGGGGTATTGACTAC (SEQ ID NO: 105). The light chain CDRs of the A9 antibody have the following sequences: TRSSGSIADNYVQ (SEQ ID NO:112), encoded by the nucleic acid sequence ACCCGCAGCAGTGGCAG-CATTGCCGACAACTATGTGCAG (SEQ ID NO:109); DDDQRLS (SEQ ID NO:113), encoded by the nucleic acid sequence GACGATGACCAAAGACTCTCT (SEQ ID NO: 110); and QSYDDSNDV (SEQ ID NO:114), encoded by the nucleic acid sequence CAGTCTTATGATGACTCCAAT-GATGTG (SEQ ID NO: 111).

An exemplary huRANTES monoclonal antibody is the E6 antibody described herein. As shown below, the E6 antibody includes a heavy chain variable region (SEQ ID NO:116) encoded by the nucleic acid sequence shown in SEQ ID NO: 115, and a light chain variable region (SEQ ID NO:118) encoded by the nucleic acid sequence shown in SEQ ID NO: 117. The CDR sequences are shown in boxes.

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the E6 antibody have the following sequences: EIAIH (SEQ ID NO:122), encoded by the nucleic acid sequence GAAATAGCCATACAC (SEQ ID NO: 119); SFEPEDAEAIYAQRFQG (SEQ ID NO:123), encoded by the nucleic acid sequence AGTTTTGAGCCTGAAGAT-GCTGAAGCAATCTACGCACAGAGGTTCCAGGGC (SEQ ID NO: 120); and DPYYASSGSNYMEV (SEQ ID NO:124), encoded by the nucleic acid sequence GATC-CCTACTATGCTAGCAGTGGTTCTAACTA-CATGGAGGTC (SEQ ID NO: 121). The light chain CDRs of the E6 antibody have the following sequences: TGSGG-SISSNYVQ (SEQ ID NO:128), encoded by the nucleic acid sequence ACCGGCAGCGGCGGCAGCATTTCCAG-CAACTATGTCCAG (SEQ ID NO:125); EDDQRPS (SEQ ID NO:129), encoded by the nucleic acid sequence GAG-GATGACCAAAGACCCTCT (SEQ ID NO: 126); and HSYDGNNRWV (SEQ ID NO:130), encoded by the nucleic acid sequence CACTCTTATGATGGCAACAATCG-GTGGGTC (SEQ ID NO: 127).

An exemplary huRANTES monoclonal antibody is the H6 antibody described herein. As shown below, the H6 antibody includes a heavy chain variable region (SEQ ID NO: 132) encoded by the nucleic acid sequence shown in SEQ ID NO: 131, and a light chain variable region (SEQ ID NO: 133) encoded by the nucleic acid sequence shown in SEQ ID NO: 132. The CDR sequences are shown in boxes.

> E6 Heavy chain variable domain nucleic acid sequence (SEQ ID NO: 115)

```
CAGGTGCAGCTGGTGCAGTCTGGGGCTGAGGTGGAGAAGCCTGGGGCCTCAGTGAAGGTC
TCCTGCAGGGTTTCGGGATACCCCCTCACTGAAATAGCCATACACTGGGTGCGACAGGCT
CCTGGAAAAGGGCTTGAGTGGATGGGAAGTTTTGAGCCTGAAGATGCTGAAGCAATCTAC
GCACAGAGGTTCCAGGGCAGAGTCACAATGACCGAGGAAACATCTGCAAACACTGCCTAC
ATGGAGCTGAGCAGCCTGAGATCTGAGGACACGGCCGTGTATTTCTGTGCAACAGATCCC
TACTATGCTAGCAGTGGTTCTAACTACATGGAGGTCTGGGGCCGAGGAACCCTGGTCACC
GTCTCGAGT
```

> E6 Heavy chain variable domain amino acid sequence (SEQ ID NO: 100)

```
QVQLVQSGAEVEKPGASVKVSCRVSGYPLTEIAIHWVRQAPGKGLEWMGSFEPEDAEAIY
AQRFQGRVTMTEETSANTAYMELSSLRSEDTAVYFCATDPYYASSGSNYMEVWGRGTLVT
VSS
```

> E6 Light chain variable domain nucleic acid sequence (SEQ ID NO: 117):

```
AATTTTATGCTGACTCAGCCCCACTCTGTGTCGGAGTCTCCGGGGAAGACGGTAACCATT
TCCTGCACCGGCAGCGGCGGCAGCATTTCCAGCAACTATGTCCAGTGGTACCGACAGCGC
CCGGGCAGCGCCCCCAGCACTGTGATCTATGAGGATGACCAAAGACCCTCTGGGGTCCCT
GATCGGATCTCTGGCTCCATCGACAGTTCCTCCAACTCTGCCTCCCTCACCATCTCTGGA
CTGACAACTGAGGACGAGGCTGACTACTATTGTCACTCTTATGATGGCAACAATCGGTGG
GTCTTCGGCGGAGGGACCAAGCTGACCGTCCTA
```

> E6 Light chain variable domain amino acid sequence (SEQ ID NO: 118)

```
NFMLTQPHSVSESPGKTVTISCTGSGGSISSNYVQWYRQRPGSAPSTVIYEDDQRPSGVP
DRISGSIDSSSNSASLTISGLTTEDEADYYCHSYDGNNRWVFGGGTKLTVL
```

> H6 Heavy chain variable domain nucleic acid sequence (SEQ ID NO: 131)

CAGGTGCAGCTGGTGCAGTCTGGGGCTGAGGTGAAGAGGCCTGGGGCCTCAGTGAAGGTC
TCCTGCAAAGTTTCCGGAAACACCCTCAGTAAACAATCCATGCACTGGGTGCGACAGGCT
CCTGGAAAAGGGTTTGAGTGGATGGGAAGTTCTAATCCTGAAGATGATGAAACACTCTAC
GCAAAGAAGTTCCAGGGCAGAGTCACCATGACCGAGGACACATCCACAGACACAGCCTAT
TTGGAGTTGAGCAGTCTGAGGTCTGAGGACACGGCCGTGTATTATTGTGCAACAGACTCC
CAGGGTTTTTACTATTACTACGGTATGGACGTCTGGGGCCAGGGCACCCTGGTCACCGTC
TCGAGT

> H6 Heavy chain variable domain amino acid sequence (SEQ ID NO: 132)

QVQLVQSGAEVKRPGASVKVSCKVSGNTLSKQSMHWVRQAPGKGFEWMGSSNPEDDETLY
AKKFQGRVTMTEDTSTDTAYLELSSLRSEDTAVYYCATDSQGFYYYGMDVWGQGTLVTV
SS

> H6 Light chain variable domain nucleic acid sequence (SEQ ID NO: 133):

CAGTCTGTGCTGACTCAGCCGCCCTCAGTGTCTGGGGCCCCAGGGCAGAGGGTCACCATC
TCCTGCACTGGGAGCAGCTCCAACATCGGGGCAGATTATGATGTACACTGGTACCAGCAA
CTTCCAGGAACAGTCCCCAAACTCCTCATCTATGATAACATCAATCGGCCCTCAGGGGTC
CCTGACCGATTCTCTGGCTCCAAGTCTGGCACCTCAGCCTCCCTGGCCATCACTGGGCTC
CAGGCTGAGGATGAGGCTGATTATTACTGCCAGTCCTATGACAGCAGCCTGAGTGGTGTG
CTATTCGGCGGAGGGACCAAGGTCACCGTCCTA

> H6 Light chain variable domain amino acid sequence (SEQ ID NO: 134)

QSVLTQPPSVSGAPGQRVTISCTGSSSNIGADYDVHWYQQLPGTVPKLLIYDNINRPSGV
PDRFSGSKSGTSASLAITGLQAEDEADYYCQSYDSSLSGVLFGGGTKVTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the H6_antibody have the following sequences: KQSMH (SEQ ID NO:138), encoded by the nucleic acid Sequence AAACAATCCATGCAC (SEQ ID NO: 135); SSNPEDDETLYAKKFQG (SEQ ID NO:139), encoded by the nucleic acid sequence AGTTCTAATCCTGAAGATGATGAAACACTCTACGCAAAGAAGTTCCAGGGC (SEQ ID NO: 136); and DSQGFYYYGMDV (SEQ ID NO:140), encoded by the nucleic acid sequence GACTCCCAGGGTTTTTACTATTACTACGGTATGGACGTC (SEQ ID NO: 137). The light chain CDRs of the H6 antibody have the following sequences: TGSSSNIGADYDVH (SEQ ID NO:144), encoded by the nucleic acid sequence ACTGGGAGCAGCTCCAACATCGGGGCAGATTATGATGTACAC (SEQ ID NO:141); DNINRPS (SEQ ID NO:145), encoded by the nucleic acid sequence GATAACATCAATCGGCCCTCA (SEQ ID NO: 142); and QSYDSSLSGVL (SEQ ID NO:146), encoded by the nucleic acid sequence CAGTCCTATGACAGCAGCCTGAGTGGTGTGCTA (SEQ ID NO: 143).

An exemplary huRANTES monoclonal antibody is the G2 antibody described herein. As shown below, the G2 antibody includes a heavy chain variable region (SEQ ID NO:148) encoded by the nucleic acid sequence shown in SEQ ID NO: 147, and a light chain variable region (SEQ ID NO:150) encoded by the nucleic acid sequence shown in SEQ ID NO: 149. The CDR sequences are shown in boxes.

> G2 Heavy chain variable domain nucleic acid sequence (SEQ ID NO: 147):

CAGGTGCAGCTGGTGCAGTCTGGGGCTGAGGTGAAGAAGCCTGGGGCCTCAGTGAAGGTC
TCCTGCAGGGCTTCGGGATACGCCCTCACTGAATTATCCATTCACTGGGTGCGACAGGCT
CCTGGAAAAGGGCTTGAGTGGATGGGAGGTTTTGATCCTGAAGATGGTGAAACAATCTAC
GCACAGAATTTCCAGGGCAGAGTCATCATGACCGAGGACACATCTACAGACACAGCCTAC
ATGGAGCTGAGCAGCCTGAAATCTGAGGACACGGCCGTGTATTATTGTGCGACAGATCTA
ACTGGAAGTAGGGACTCCTGGGGCCAAGGCACCCTGGTCACCGTCTCGAGT

> G2 Heavy chain variable domain amino acid sequence (SEQ ID NO: 148):

QVQLVQSGAEVKKPGASVKVSCRASGYALTELSIHWVRQAPGKGLEWMGGFDPEDGETIY
AQNFQGRVIMTEDTSTDTAYMELSSLKSEDTAVYYCATDLTGSRDSWGQGTLVTVSS

> G2 Light chain variable domain nucleic acid sequence (SEQ ID NO: 149):

CAGTCTGTGCTGACTCAGCCTGCCTCCGTGTCTGGGTCTCCTGGACAGTCGATCACCATC
TCCTGCACTGGAAGCAGGAGTGACATTGGTTACTATAACTATGTCTCCTGGTACCAACAA
CACCCAGGGAAAGTCCCCAAACTCATAATTTATGATGTCACTGAGCGACCCTCAGGGGTT
TCTGATCGCTTCTCTGGCTCCAAGTCTGCCAACACGGCCTCCCTGACCATCTCTGGGCTC
CAGGCTGAGGACGAGGCTGATTATTACTGCAGCTCATTTTCAAGTGGCGACACCTTCGTG
GTTTTCGGCGGAGGGACCAAGCTGACCGTCCTA

> G2 Light chain variable domain amino acid sequence (SEQ ID NO: 150)

QSVLTQPASVSGSPGQSITISCTGSRSDIGYYNYVSWYQQHPGKVPKLIIYDVTERPSGV
SDRFSGSKSANTASLTISGLQAEDEADYYCSSFSSGDTFVVFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the G2_antibody have the following sequences: ELSIH (SEQ ID NO:154), encoded by the nucleic acid sequence GAATTATCCATTCAC (SEQ ID NO: 151); GFDPEDGETIYAQNFQG (SEQ ID NO:155), encoded by the nucleic acid sequence GGTTTTGATCCTGAAGATGGTGAAACAATCTACGCACAGAATTTCCAGGGC (SEQ ID NO: 152); and DLTGSRDS (SEQ ID NO:156), encoded by the nucleic acid sequence GATCTAACTGGAAGTAGGGACTCC (SEQ ID NO: 153). The light chain CDRs of the G2 antibody have the following sequences: TGSRSDIGYYNYVS (SEQ ID NO:160), encoded by the nucleic acid sequence ACTGGAAGCAGGAGTGACATTGGTTACTATAACTATGTCTCC (SEQ ID NO:157); DVTERPS (SEQ ID NO:161), encoded by the nucleic acid sequence GATGTCACTGAGCGACCCTCA (SEQ ID NO: 158); and SSFSSGDTFVV (SEQ ID NO:162), encoded by the nucleic acid sequence AGCTCATTTTCAAGTGGCGACACCTTCGTGGTT (SEQ ID NO: 159).

An exemplary huRANTES monoclonal antibody is the E10 antibody described herein. As shown below, the E10 antibody includes a heavy chain variable region (SEQ ID NO:164) encoded by the nucleic acid sequence shown in SEQ ID NO: 163, and a light chain variable region (SEQ ID NO:166) encoded by the nucleic acid sequence shown in SEQ ID NO: 165. The CDR sequences are shown in boxes.

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the E10 antibody have the following sequences: SYAMH (SEQ ID NO:28), encoded by the nucleic acid sequence AGCTATGCTATGCAC (SEQ ID NO: 25)); VISYDGSNKYYADSVKG (SEQ ID NO:29), encoded by the nucleic acid sequence GTTATATCATATGATGGAAGTAATAAATACTACGCAGACTCCGTGAAGGGC ( SEQ ID NO: 26); and ETFPHYYYYYMDV (SEQ ID NO:30), encoded by the nucleic acid sequence GAAACTTTCCCCCACTACTACTACTACTACATGGACGTC (SEQ ID NO: 27). The light chain CDRs of the E10 antibody have the following sequences: GGGNFDDEGVH (SEQ ID NO:176), encoded by the nucleic acid sequence GGGGGAGGCAACTTTGACGATGAAGGTGTTCAC (SEQ ID NO:173); DDTGRPS (SEQ ID NO:177), encoded by the nucleic acid sequence GATGATACCGGCCGGCCCTCA (SEQ ID NO: 174); and QAWDSSNDHPV (SEQ ID NO:178), encoded by the nucleic acid sequence CAGGCGTGGGATAGTAGTAATGATCATCCCGTG (SEQ ID NO: 175).

An exemplary huRANTES monoclonal antibody is the C10 antibody described herein. As shown below, the C10 antibody includes a heavy chain variable region (SEQ ID NO:180) encoded by the nucleic acid sequence shown in SEQ ID NO: 179, and a light chain variable region (SEQ ID NO: 182) encoded by the nucleic acid sequence shown in SEQ ID NO: 181. The CDR sequences are shown in boxes.

```
> E10 Heavy chain variable domain nucleic acid sequence (SEQ ID NO: 163):

CAGGTGCAGCTGGTGGAGTCTGGGGGAGGCGTGGTCCAGCCTGGGAGGTCCCTGAGACTC
TCCTGTGCAGCCTCTGGATTCACCTTCAGTAGCTATGCTATGCACTGGGTCCGCCAGGCT
CCAGGCAAGGGGCTAGAGTGGGTGGCAGTTATATCATATGATGGAAGTAATAAATACTAC
GCAGACTCCGTGAAGGGCCGATTCTCCATCTCCAGAGACAATTCCAAGAACACGCTGTAT
CTGCAAATCAACAGCCTGAGAGCTGAGGACACGGCTGTGTATTACTGTGCGAGAGAAACT
TTCCCCCACTACTACTACTACTACATGGACGTCTGGGGCAAGGGGACAATGGTCACCGTC
TCGAGT

> E10 Heavy chain variable domain amino acid sequence (SEQ ID NO: 164):

QVQLVESGGGVVQPGRSLRLSCAASGFTFSSYAMHWVRQAPGKGLEWVAVISYDGSNKYY
ADSVKGRFSISRDNSKNTLYLQMNSLRAEDTAVYYCARETFPHYYYYYMDVWGKGTMVTV
SS

> E10 Light chain variable domain nucleic acid sequence (SEQ ID NO: 165):

TCCTATGTGCTGACTCAGCCACCCTCGGTGTCCGTGGCCCCAGGGCAGACGGCCAGAATT
TCCTGTGGGGGAGGCAACTTTGACGATGAAGGTGTTCACTGGTACCAGCAGACCCCAGGC
CAGGCCCCTGTACTGGTCGTCTATGATGATACCGGCCGGCCCTCAGGGATCCCTGAGCGA
TTCTCTGGCTCCAGTTCTGGGAATACGGCCACCCTGACCATCAGCCGGGTCGAAGCCGGG
GATGAGGCCGACTATTACTGTCAGGCGTGGGATAGTAGTAATGATCATCCCGTGTTCGGC
GGAGGGACCCAGCTCACCGTCCTA

> E10 Light chain variable domain amino acid sequence (SEQ ID NO: 166)

SYVLTQPPSVSVAPGQTARISCGGGNFDDEGVHWYQQTPGQAPVLVVYDDTGRPSGIPER
FSGSSSGNTATLTISRVEAGDEADYYCQAWDSSNDHPVFGGGTQLTVL
```

> C10 Heavy chain variable domain nucleic acid sequence (SEQ ID NO: 179):

```
GAGGTGCAGCTGTTGGAGTCTGGGGGAGGCTTGGTACAGCCTGGGGGGTCCCTGAGACTC
TCCTGTGCAGCCTCTGGATTCACCTTTAGCAGCTATGCCATGAGCTGGGTCCGCCAGGCT
CCAGGGAAGGGGCTGGAGTGGGTCTCAGCTATTAGTGGTAGTGGTGGTAGCACATACTAC
GCAGACTCCGTGAAGGGCCGGTTCACCATCTCCAGAGACAATTCCAAAAACACGCTGTAT
CTGCAAATGAACAGCCTGAGAGCCGAGGACACGGCCGTGTATTACTGTGCAAGAGTAAGG
GGGAGTTCCCAGTACGATTTTTGGAGTGGGTCCGAGTTTGACTACTGGGGCCAGGGGACA
ATGGTCACCGTCTCGAGT
```

> C10 Heavy chain variable domain amino acid sequence (SEQ ID NO: 180):

```
EVQLLESGGGLVQPGGSLRLSCAASGFTFSSYAMSWVRQAPGKGLEWVSAISGSGGSTYY
ADSVKGRFTISRDNSKNTLYLQMNSLRAEDTAVYYCARVRGSSQYDFWSGSEFDYWGQGT
MVTVSS
```

> C10 Light chain variable domain nucleic acid sequence (SEQ ID NO: 181):

```
TCCTATGTGCTGACTCAGCCACCCTCAGTGTCAGTGGCCCCAGGAAAGACGGCCAGCATT
TCCTGTGGGGGAGACAACATTGGAGGTCAAAATGTTCACTGGTATCAGCAGAAGCCAGGC
CAGGCCCCTGTGCTCGTCATCTATTATGATACCGACCGGCCCTCAGGGATCCCTGAGCGA
TTCTCTGGCTCCAACTCTGGGAACACGGCCACCCTGTCCATCAGCAGGGTCGAAGCCGGG
GATGAGGCCGACTATTACTGTCAGGTGTGGGATGTTGATAGTGATCATCCTTGGGTGTTC
GGCGGAGGGACCAAGCTGACCGTCCTA
```

> C10 Light chain variable domain amino acid sequence (SEQ ID NO: 182)

```
SYVLTQPPSVSVAPGKTASISCGGDNIGGQNVHWYQQKPGQAPVLVIYYDTDRPSGIPER
FSGSNSGNTATLSISRVEAADEADYYCQVWDVDSDHPWVFGGGTKLTVL
```

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the C10 antibody have the following sequences: SYAMS (SEQ ID NO:106), encoded by the nucleic acid sequence AGCTATGCCATGAGC (SEQ ID NO: 103); AISGSGGSTYYADSVKG (SEQ ID NO:107), encoded by the nucleic acid sequence GCTATTAGTGG-TAGTGGTGGTAGCACATACTACGCA-GACTCCGTGAAGGGC (SEQ ID NO: 104); and VRGSSQYDFWSGSEFDY (SEQ ID NO:188), encoded by the nucleic acid sequence GTAAGGGGGAGTTCCCAG-TACGATTTTTGGAGTGGGTCCGAGTTTGACTAC (SEQ ID NO: 185). The light chain CDRs of the C10 antibody have the following sequences: GGDNIGGQNVH (SEQ ID NO:192), encoded by the nucleic acid sequence GGGG-GAGACAACATTGGAGGTCAAAATGTTCAC (SEQ ID NO:189); YDTDRPS (SEQ ID NO:193), encoded by the nucleic acid sequence TATGATACCGACCGGCCCTCA (SEQ ID NO: 190); and QVWDVDSDHPWV (SEQ ID NO:194), encoded by the nucleic acid sequence CAGGT-GTGGGATGTTGATAGTGATCATCCTTGGGTG (SEQ ID NO: 191).

An exemplary huRANTES monoclonal antibody is the 2D1 antibody described herein. As shown below, the 2D1 antibody includes a heavy chain variable region (SEQ ID NO:60) encoded by the nucleic acid sequence shown in SEQ ID NO: 59, and a light chain variable region (SEQ ID NO: 196) encoded by the nucleic acid sequence shown in SEQ ID NO: 195. The CDR sequences are shown in boxes.

> 2D1 Heavy chain variable domain nucleic acid sequence (SEQ ID NO: 59)

```
CAGGTGCAGCTGGTGCAGTCTGGGGCTGAGGTGAAGAAGCCTGGGGCCTCAGTGAAGGTT
TCCTGCAAGGTTTCCGGATACACCCTCAATGACTTCGCCATGCACTGGGTGCGACAGGCT
CCTGGAAAAGGGCTTGAGTGGATGGGAGGTTATGTTCCTGAAGATGGTGACACAATCTAC
GCGCAGAAGTTCCAGGGCAGAGTCACCATGACCGAGGACACATCTACAGACACAGCCTAC
ATGGAGCTGAGCAGCCTGAGATCTGAGGACACGGCCGTGTATTACTGTGCAACAGATCCC
CTGTATAGTGGGAGCTTATCCTACTGGGGCCAGGGGACCACGGTCACCGTCTCGAGT
```

> 2D1 Heavy chain variable domain amino acid sequence (SEQ ID NO: 60)

```
QVQLVQSGAEVKKPGASVKVSCKVSGYTLNDFAMHWVRQAPGKGLEWMGGYVPEDGDTIY
AQKFQGRVTMTEDTSTDTAYMELSSLRSEDTAVYYCATDPLYSGSLSYWGQGTTVTVSS
```

> 2D1 Light chain variable domain nucleic acid sequence (SEQ ID NO: 195):

```
TCCTATGTGCTGACTCAGCCACCCTCGGTGTCAGTGGCCCCAGGACAGACGGCCAGGATT
ACCTGTGGGGGAAACAACATTGAAAGTAAAAGTGTGCACTGGTACCAGCAGAAGCCAGGC
CAGGCCCCTGTGCTGGTGGTCTATGATGATAGCGACCGGCCCTCAGGGATCCCTGAGCGA
TTCTCTGGCTCCAACTCTGGGAACACGGCCACCCTGACCATCAGCAGGGTCGAAGCCGGG
GATGAGGCCGACTATTACTGTCAGGTGTGGGATAGTAATACTGATCATTGGGTGTTCGGC
GGAGGGACCAAGGTCACCGTCCTA
```

> 2D1 Light chain variable domain amino acid sequence (SEQ ID NO: 196)

```
SYVLTQPPSVSVAPGQTARITCGGNNIESKSVHWYQQKPGQAPVLVVYDDSDRPSGIPER
FSGSNSGNTATLTISRVEAGDEADYYCQVWDSNTDHWVFGGGTKVTVL
```

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the 2D1 antibody have the following sequences: DFAMH (SEQ ID NO:44), encoded by the nucleic acid sequence GACTTCGCCATGCAC (SEQ ID NO: 41); GYVPEDGDTIYAQKFQG (SEQ ID NO:45), encoded by the nucleic acid sequence GGTTATGTTCCTGAAGATGGTGACACAATCTACGCGCAGAAGTTCCAGGGC (SEQ ID NO: 42); and DPLYSGSLSY (SEQ ID NO:64), encoded by the nucleic acid sequence GATCCCCTGTATAGTGGGAGCTTATCCTAC (SEQ ID NO: 53). The light chain CDRs of the 2D1 antibody have the following sequences: GGNNIESKSVH (SEQ ID NO:14), encoded by the nucleic acid sequence GGGGGAAACAACATTGAAAGTAAAAGTGTGCAC (SEQ ID NO:11); DDSDRPS (SEQ ID NO:15), encoded by the nucleic acid sequence GATGATAGCGACCGGCCCTCA (SEQ ID NO: 12); and QVWDSNTDHWV (SEQ ID NO: 16), encoded by the nucleic acid sequence CAGGTGTGGGATAGTAATACTGATCATTGGGTG (SEQ ID NO: 13).

An exemplary huRANTES monoclonal antibody is the A5 antibody described herein. As shown below, the A5 antibody includes a heavy chain variable region (SEQ ID NO:200) encoded by the nucleic acid sequence shown in SEQ ID NO: 199, and a light chain variable region (SEQ ID NO:202) encoded by the nucleic acid sequence shown in SEQ ID NO: 201. The CDR sequences are shown in boxes.

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the A5 antibody have the following sequences: ELSIH (SEQ ID NO:154), encoded by the nucleic acid sequence GAATTATCCATACAC (SEQ ID NO: 203); YIDPEDGEPIYAQKFQG (SEQ ID NO:207), encoded by the nucleic acid sequence TATATTGATCCTGAAGATGGTGAACCAATTTACGCACAGAAGTTCCAGGGC (SEQ ID NO: 204); and VTGSTSDAFDL (SEQ ID NO:208), encoded by the nucleic acid sequence GTCACTGGAAGTACTTCGGATGCCTTTGATCTC (SEQ ID NO: 205). The light chain CDRs of the A5 antibody have the following sequences: GGANLWGLGVH (SEQ ID NO:212), encoded by the nucleic acid sequence GGGGGAGCCAATCTTTGGGGTCTAGGTGTCCAT (SEQ ID NO:209); DNSDRAS (SEQ ID NO:213), encoded by the nucleic acid sequence GATAATAGCGACCGGGCCTCA (SEQ ID NO: 210); and QVWDSSSDHWV (SEQ ID NO:214), encoded by the nucleic acid sequence CAGGTGTGGGATAGTAGTAGTGATCACTGGGTG (SEQ ID NO: 211).

An exemplary huRANTES monoclonal antibody is the H11 antibody described herein. As shown below, the H11 antibody includes a heavy chain variable region (SEQ ID NO:216) encoded by the nucleic acid sequence shown in SEQ ID NO: 215, and a light chain variable region (SEQ ID NO:218) encoded by the nucleic acid sequence shown in SEQ ID NO: 217. The CDR sequences are shown in boxes.

> A5 Heavy chain variable domain nucleic acid sequence (SEQ ID NO: 199)

```
CAGGTGCAGCTGGTGCAGTCTGGGGCTGAGGTGAAGAAGCCTGGGGCCTCAGTGAAGGTC
TCCTGCAAGGTTTCCGGATACGCCCTCAGTGAATTATCCATACACTGGGTGCGACAGGCT
CCTGGCAAAGGCCTTGAGTGGATGTCGTATATTGATCCTGAAGATGGTGAACCAATTTAC
GCACAGAAGTTCCAGGGCAGAGCCACCATGACCGAGGACTCATCTACAGACACAGCCTAC
ATGGAGATGGGCAGCCTGACATCTGACGACACGGCCGTTTATTACTGTGCAGGTGTCACT
GGAAGTACTTCGGATGCCTTTGATCTCTGGGGCCGGGGAACCCTGGTCACCGTCTCGAGT
```

> A5 Heavy chain variable domain amino acid sequence (SEQ ID NO: 200)

```
QVQLVQSGAEVKKPGASVKVSCKVSGYALSELSIHWVRQAPGKGLEWMSYIDPEDGEPIY
AQKFQGRATMTEDSSTDTAYMEMGSLTSDDTAVYYCAGVTGSTSDAFDLWGRGTLVTVSS
```

> A5 Light chain variable domain nucleic acid sequence (SEQ ID NO: 201):

```
TCCTATGTGCTGACTCAGGACCCCTCGGTGTCAGTGGCCCCAGGACAGACGGCCAGGATC
ACCTGTGGGGGAGCCAATCTTTGGGGTCTAGGTGTCCATTGGTATCAACAAAAGTCAGGC
CAGGCCCCTGTGTTGGTCGTCTCTGATAATAGCGACCGGGCCTCAGGGATCCCTGAGCGA
TTCTCTGGCTCCAATTCTGGGACCACGGCCACCCTGACCCTCAGCAGGGTCGAAGTCGGC
GATGAGGCCGACTATTACTGTCAGGTGTGGGATAGTAGTAGTGATCACTGGGTGTTCGGC
GGCAGGACCAAGCTGACCGTCCTA
```

> A5 Light chain variable domain amino acid sequence (SEQ ID NO: 202)

```
SYVLTQDPSVSVAPGQTARITCGGANLWGLGVHWYQQKSGQAPVLVVSDNSDRASGIPER
FSGSNSGTTATLTLSRVEVGDEADYYCQVWDSSSDHWVFGGRTKLTVL
```

> H11 Heavy chain variable domain nucleic acid sequence (SEQ ID NO: 215)

CAGGTGCAGCTGGTGCAGTCTGGGGCTGAGGTGAAGAAGCCTGGGTCGTCGGTGAAGGTC
TCCTGCAAGGCCTCTGGAGGCATCTCCGACAACTATGCTCTCAGCTGGGTGCGACAGGCC
CCTGGCCAAGGACTTGAGTGGATGGGAGGGTTCATCCCTCTCGTCGATACTACGAACTAC
GCACAGAGGTTTCAGGGCAGACTCACGATTACCGCGGACGACTCCATGAGTACAGTCTAC
ATGGAACTAAGAAGCCTGCGATCTGACGACACGGCCATGTATTATTGTGCGAGAGAGCAG
GTGGCGGTGGGACCTGGACCCACCTCAGACCGGGGGCCCGATGGTCTTGATGTCTGGGGC
CAAGGGACAATGGTCACCGTCTCGAGT

> H11 Heavy chain variable domain amino acid sequence (SEQ ID NO: 216)

QVQLVQSGAEVKKPGSSVKVSCKASGGISDNYALSWVRQAPGQGLEWMGGFIPLVDTTNY
AQRFQGRLTITADDSMSTVYMELRSLRSDDTAMYYCAREQVAVGPGPTSDRGPDGLDVWG
QGTMVTVSS

> H11 Light chain variable domain nucleic acid sequence (SEQ ID NO: 217):

CAGTCTGTGCTGACTCAGCCGTCCTCAGTGTCTGGGGCCCCAGGGCACAGGGTCACCATT
TCCTGCACTGGGAGCAACTCCAACCTCGGGGCGGATTATGATGTACACTGGTATCAGCAG
CTTCCAGGGTCAGCCCCCAAACTCCTCATCTATGATAACAACATTCGTCCCTCAGGGGTC
CCTGCCCGATTCTCTGGCTCCAAGTCTGGCACCTCAGCCTCCCTGGCCATCACTGGGCTC
CAGGCTGAAGATGAGGCTGATTATTACTGCCAGTCGTATGACACCGGCCTGACTTCTTCG
GATGTGATATTCGGCGGAGGGACCAAGCTGACCGTCCTA

> H11 Light chain variable domain amino acid sequence (SEQ ID NO: 218)

QSVLTQPSSVSGAPGHRVTISCTGSNSNLGADYDVHWYQQLPGSAPKLLIYDNNIRPSGV
PARFSGSKSGTSASLAITGLQAEDEADYYCQSYDTGLTSSDVIFGGGTKLTVL

The amino acids encompassing the complementarity determining regions (CDR) are as defined by Chothia et al. and E. A. Kabat et al. (See Chothia, C, et al., Nature 342:877-883 (1989); Kabat, E A, et al., Sequences of Protein of immunological interest, Fifth Edition, US Department of Health and Human Services, US Government Printing Office (1991)). The heavy chain CDRs of the H11 antibody have the following sequences: NYALS (SEQ ID NO:222), encoded by the nucleic acid sequence AACTATGCTCTCAGC (SEQ ID NO: 219); GFIPLVDTTNYAQRFQG (SEQ ID NO:223), encoded by the nucleic acid sequence GGGTTCATCCCTCTCGTC-GATACTACGAACTACGCACAGAGGTTTCAGGGC (SEQ ID NO: 220); and EQVAVGPGPTSDRGPDGLDV (SEQ ID NO:224), encoded by the nucleic acid sequence GAGCAGGTGGCGGTGGGACCTGGAC-CCACCTCAGACCGGGGGCCCGATGGTCTTG ATGTC (SEQ ID NO: 221). The light chain CDRs of the H11 antibody have the following sequences: TGSNSNLGADYDVH (SEQ ID NO:228), encoded by the nucleic acid sequence ACTGG-GAGCAACTCCAACCTCGGGGCGGATTAT-GATGTACAC (SEQ ID NO:225); DNNIRPS (SEQ ID NO:229), encoded by the nucleic acid sequence GATAA-CAACATTCGTCCCTCA (SEQ ID NO: 226); and QSYDT-GLTSSDVI (SEQ ID NO:230), encoded by the nucleic acid sequence CAGTCGTATGACACCGGCCTGACTTCT-TCGGATGTGATA (SEQ ID NO: 227).

An exemplary huRANTES monoclonal antibody is the D1 antibody described herein. As shown below, the D1 antibody includes a heavy chain variable region (SEQ ID NO:232) encoded by the nucleic acid sequence shown in SEQ ID NO: 231, and a light chain variable region (SEQ ID NO:234) encoded by the nucleic acid sequence shown in SEQ ID NO: 233. The CDR sequences are shown in boxes.

> D1 Heavy chain variable domain nucleic acid sequence (SEQ ID NO: 231)

GAGGTGCAGCTGGTGCAGTCTGGGCCTGAGGTGAAGAAGCCTGGGGCCACAGTGAAAATTTCC
TGCAAGCGTCTCTGCAGAAACCTTCACCGACTACTACATACAGTGGGTCAAACAGGCCCCTGGA
AGAGGGCTGGAGTGGATGGGGCTTGTTGATTCTGAAGAAGATGGTGAAACATTATTCGCAGAG
ACTTTCAGGGGCAGAGTCGCCCTAACCGCGGACAGGTCCACAAACACCGCCTACATGGAGTTG
CGCAGCCTGAGACATGACGACACGGCCGTCTATTATTGTGCAGCAGAATATGGTGAATATGGG
TTCTTCCAATCGTGGGGCCAGGGAACCCTGGTCACCGTCTCGAGT

> D1 Heavy chain variable domain amino acid sequence (SEQ ID NO: 232)

EVQLVQSGPEVKKPGATVKISCNVSAETFTDYYIHWVKQAPGRGLEWMGLVDSEEDGETLFA
ETFRGRVALTADRSTNTAYMELRSLRHDDTAVYYCAAEYGEYGFFQSWGQGTLVTVSS

> D1 Light chain variable domain nucleic acid sequence (SEQ ID NO: 233):

CAGTCTGTGCTGACTCAGCCACCCTCAGTGTCTGGGGCCCCAGGGCAGAGGGTCACCATC
TCCTGCACTGGGAGCAGCTCCAACATCGGGGCAGATTATGATGTAAACTGGTACCAGCAG
CTTCCAGGAACTTCCCCCAAACTCCTCATCTATGGTGACATCAATCGGCCCTCAGGGGTC
CCTGACCGATTCTCTGCCTCCAAGTCTGGCACCTCAGCCTCCCTGGCCATCACTGGGCTC
CAGGCTGAGGATGAGGCTGATTATTACTGCCAGTCGTTTGACAACAGCCTGAGTGGGTCT
GTGATTTTCGGCGGAGGGACCAAGCTGACCGTCCTA

> D1 Light chain variable domain amino acid sequence (SEQ ID NO: 234)

QSVLTQPPSVSGAPGQRVTISCTGSSSNIGADYDVNWYQQLPGTSPKLLIYGDINRPSGV
PDRFSASKSGTSASLAITGLQAEDEADYYCQSFDNSLSGSVIFGGGTKLTVL

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the D1 antibody have the following sequences: DYYIH (SEQ ID NO:74), encoded by the nucleic acid sequence GACTACTACATACAC (SEQ ID NO: 71); LVDSEEDGETLFAETFRG(SEQ ID NO:239), encoded by the nucleic acid sequence CTTGTTGATTCTGAAGAAGATGGTGAAACATTATTCGCAGAGACTTTCAGGGGC (SEQ ID NO: 236); and EYGEYGFFQS (SEQ ID NO:240), encoded by the nucleic acid sequence GAATATGGTGAATATGGGTTCTTCCAATCG (SEQ ID NO: 237). The light chain CDRs of the D1 antibody have the following sequences: TGSSSNIGADYDVN (SEQ ID NO:244), encoded by the nucleic acid sequence ACTGGGAGCAGCTCCAACATCGGGGCAGATTATGATGTAAAC (SEQ ID NO:241); GDINRPS (SEQ ID NO:245), encoded by the nucleic acid sequence GGTGACATCAATCGGCCCTCA (SEQ ID NO: 242); and QSFDNSLSGSVI (SEQ ID NO:246), encoded by the nucleic acid sequence CAGTCGTTTGACAACAGCCTGAGTGGGTCTGTGATT (SEQ ID NO: 243).

An exemplary huRANTES monoclonal antibody is the E7 antibody described herein. As shown below, the E7 antibody includes a heavy chain variable region (SEQ ID NO:248) encoded by the nucleic acid sequence shown in SEQ ID NO: 247, and a light chain variable region (SEQ ID NO:250) encoded by the nucleic acid sequence shown in SEQ ID NO: 249. The CDR sequences are shown in boxes.

The amino acids encompassing the complementarity determining regions (CDR) are as defined by Chothia et al. and E.A. Kabat et al. (See Chothia, C, et al., Nature 342:877-883 (1989); Kabat, EA, et al., Sequences of Protein of immunological interest, Fifth Edition, US Department of Health and Human Services, US Government Printing Office (1991)). The heavy chain CDRs of the E7 antibody have the following sequences: NYALS (SEQ ID NO:222), encoded by the nucleic acid sequence AACTACGCTCTGAGC (SEQ ID NO: 251); AVIPLVETTSYAQRFQG (SEQ ID NO:255), encoded by the nucleic acid sequence GCGGTCATCCCTCTCGTCGAGACTACGAGCTACGCACAGAGGTTCCAGGGC (SEQ ID NO: 252); and EQVAVGPGPTSNRGPDGLDV (SEQ ID NO: 169), encoded by the nucleic acid sequence GAGCAGGTGGCGGTGGGACCTGGACCCACTTCAAATCGGGGGCCCGATGGCCTAGA TGTC (SEQ ID NO: 253). The light chain CDRs of the E7 antibody have the following sequences: TGSSSNIGDGYDVH (SEQ ID NO: 190), encoded by the nucleic acid sequence ACTGGGAGCAGCTCCAACATCGGGGACGGTTATGATGTACAC ( SEQ ID NO: 183); GNSNRPS (SEQ ID NO: 191), encoded by the nucleic acid sequence GGTAACAGTAATCGGCCCTCA (SEQ ID NO: 184); and GTWDDILNGWV (SEQ ID NO: 235), encoded by the nucleic acid sequence GGAACATGGGATGACATCCTGAATGGTTGGGTG (SEQ ID NO: 189).

huRANTES antibodies of the invention also include antibodies that include a heavy chain variable amino acid sequence that is at least 90%, 92%, 95%, 97%, 98%, 99% or more identical the amino acid sequence of SEQ ID NO: 2, 18, 22, 38, 48, 52, 56, 60, 68, 84, 100, 116, 132, 148, 164, 180, 200, 216, 232, or 248 and/or a light chain variable amino acid that is at least 90%, 92%, 95%, 97%, 98%, 99% or more identical the amino acid sequence of SEQ ID NO: 4, 24, 40, 62, 70, 86, 102, 118, 134, 150, 166, 182, 196, 202, 218, 234, or 250.

Alternatively, the monoclonal antibody is an antibody that binds to the same epitope as 1D9, 1E4, C8, 3E7,4D8, 5E1, 6A8, 7B5, CG11, BG11, A9, E6, H6, G2, E10, C10, 2D1, A5, H11, D1 and/or E7.

Unless otherwise defined, scientific and technical terms used in connection with the present invention shall have the > E7 Heavy chain variable domain nucleic acid sequence (SEQ ID NO: 247)

```
CAGGTGCAGCTGGTGCAGTCTGGGGCTGAGGTGAAGAAGCCGGGGTCGTCGGTGAAGGTC
TCCTGCAAGATTTCTGGAGGCATCTCCGACAACTACGCTCTGAGCTGGGTGCGACAGGCC
CCTGGGCAAGGACTTGAGTGGATGGGAGCGGTCATCCCTCTCGTCGAGACTACGAGCTAC
GCACAGAGGTTCCAGGGCAGACTCACAATTACCGCGGACGACTCCTTGAATACACTGTAC
ATGGAATTGGGAAGCCTGCGATCTGACGACACGGCCATGTATTACTGTGCGAGAGAGCAG
GTGGCGGTGGGACCTGGACCCACTTCAAATCGGGGGCCCGATGGCCTAGATGTCTGGGGC
AGAGGGACAATGGTCACCGTCTCGAGT
```

> E7 Heavy chain variable domain amino acid sequence (SEQ ID NO: 248)

```
QVQLVQSGAEVKKPGSSVKVSCKISGGISDNYALSWVRQAPGQGLEWMGAVIPLVETTSY
AQRFQGRLTITADDSLNTLYMELGSLRSDDTAMYYCAREQVAVGPGPTSNRGPDGLDVWG
RGTMVTVSS
```

> E7 Light chain variable domain nucleic acid sequence (SEQ ID NO: 249):

```
CAGTCTGTGCTGACTCAGCCACCCTCAGTGTCTGGGGCCCCAGGGCAGAGGGTCACCATC
TCCTGCACTGGGAGCAGCTCCAACATCGGGGACGGTTATGATGTACACTGGTATCAGCAG
CTTCCAGGAACAGCCCCCAAACTCCTCATCTATGGTAACAGTAATCGGCCCTCAGGGGTC
CCTGACCGATTCTCTGGCTCCACCTCTGGCACCTCCGCCTCCCTGGCCATCCGTGGGCTC
CAGTCTGAGGATGAGGCTGATTACTACTGTGGAACATGGGATGACATCCTGAATGGTTGG
GTGTTCGGCGGAGGGACCAAGCTGACCGTCCTA
```

> E7 Light chain variable domain amino acid sequence (SEQ ID NO: 250)

```
QSVLTQPPSVSGAPGQRVTISCTGSSSNIGDGYDVHWYQQLPGTAPKLLIYGNSNRPSGV
PDRFSGSTSGTSASLAIRGLQSEDEADYYCGTWDDILNGWVFGGGTKLTVL
``` meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA and oligonucleotide synthesis, as well as tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, delivery and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, $F_{ab}$, $F_{ab'}$ and $F_{(ab')2}$ fragments, and antibodies in an $F_{ab}$ expression library. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ea., 2nd ed. Raven Press, N.Y. (1989)). The variable regions of each light/heavy chain pair form the antibody binding site.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is $\leq 1$ µM; e.g., $\leq 100$ nM, preferably $\leq 10$ nM and more preferably $\leq 1$ nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a RANTES epitope when the equilibrium binding constant ($K_d$) is $\leq 1$ µM, e.g., $\leq 100$ nM, preferably $\leq 10$ nM, and more preferably $\leq 1$ nM, as measured by assays such as radioligand binding assays or surface plasmon resonance (SPR) or similar assays known to those skilled in the art. For example, the huRANTES antibodies provided herein exhibit a $K_d$ in the range approximately between $\leq 10$ nM to about 100 pM.

Those skilled in the art will recognize that it is possible to determine, without undue experimentation, if a human monoclonal antibody has the same specificity as a human monoclonal antibody of the invention (e.g., monoclonal antibody D9, E4 or C8) by ascertaining whether the former prevents the latter from binding to a RANTES antigen polypeptide. If the human monoclonal antibody being tested competes with a human monoclonal antibody of the invention, as shown by a decrease in binding by the human monoclonal antibody of the invention, then the two monoclonal antibodies bind to the same, or a closely related, epitope. Another way to determine whether a human monoclonal antibody has the specificity of a human monoclonal antibody of the invention is to preincubate the human monoclonal antibody of the invention with the RANTES antigen polypeptide with which it is normally reactive, and then add the human monoclonal antibody being tested to determine if the human monoclonal antibody being tested is inhibited in its ability to bind the RANTES antigen polypeptide. If the human monoclonal antibody being tested is inhibited then, in all likelihood, it has the same, or functionally equivalent, epitopic specificity as the monoclonal antibody of the invention.

Various procedures known within the art are used for the production of the monoclonal antibodies directed against a protein such as a RANTES protein, or against derivatives, fragments, analogs homologs or orthologs thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

In some instances, it may be desirable to modify the antibody of the invention with respect to effector function, so as to enhance, e.g., the effectiveness of the antibody in treating immune-related diseases. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)). In a preferred embodiment, the huRANTES antibodies of the invention are not modified with respect to effector function.

The invention also includes $F_v$, $F_{ab}$, $F_{ab'}$ and $F_{(ab')2}$ huRANTES antibody fragments, single chain huRANTES antibodies, bispecific huRANTES antibodies and heteroconjugate huRANTES antibodies.

Bispecific antibodies are antibodies that have binding specificities for at least two different antigens. In the present case, one of the binding specificities is for RANTES. The second binding target is any other antigen, and in some embodiments, the second binding target is an extracellular target such as a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

Other approaches for generating bispecific antibodies are described, e.g., in WO 96/27011, which is hereby incorporated by reference in its entirety. Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared using chemical linkage. See e.g., Brennan et al., Science 229:81 (1985), which is hereby incorporated by reference in its entirety.

Additionally, Fab' fragments can be directly recovered from E. coli and chemically coupled to form bispecific antibodies. See e.g., Shalaby et al., J. Exp. Med. 175:217-225 (1992), which is hereby incorporated by reference in its entirety.

Various techniques for making and isolating bispecific antibody fragments directly from recombinant cell culture have also been described. For example, bispecific antibodies have been produced using leucine zippers. See e.g., Kostelny et al., J. Immunol. 148(5):1547-1553 (1992), which is hereby incorporated by reference in its entirety. The "diabody" technology described by Hollinger et al., Proc. Natl. Acad. Sci.

USA 90:6444-6448 (1993), which is hereby incorporated by reference in its entirety, has provided an alternative mechanism for making bispecific antibody fragments. Another strategy for making bispecific antibody fragments by the use of single-chain Fv (sFv) dimers has also been reported. See, Gruber et al., J. Immunol. 152:5368 (1994), which is hereby incorporated by reference in its entirety.

Antibodies with more than two valencies are contemplated. For example, trispecific antibodies can be prepared. See, Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, IFNγ, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{86}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling is accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding is achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Preferred polypeptides in accordance with the invention comprise the human heavy chain immunoglobulin molecules presented herein and the human light chain immunoglobulin molecules presented herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes Oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest will be at least 80%, and more typically with preferably increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention.

Similarly, unless specified otherwise, the lefthand end of single-stranded polynucleotide sequences is the 5' end the lefthand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, preferably at least 14 amino acids long more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to RANTES, under suitable binding conditions or (2) ability to block appropriate RANTES binding. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TIBS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects. The term subject includes humans and other mammals.

Human Antibodies and Humanization of Antibodies

A huRANTES antibody is generated, for example, using the procedures described in the Examples provided below.

In other, alternative methods, a huRANTES antibody is developed, for example, using phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of RANTES or fragments thereof. In another approach, a huRANTES antibody can be produced by a process wherein at least one step of the process includes immunizing a transgenic, non-human animal with human RANTES protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. No. 6,075,181 and No. 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963, 6,150,584, 6, 114,598, 6,075,181, and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

In an alternative approach, others have utilized a "minilocus" approach in which an exogenous Ig locus is mimicked through the inclusion of pieces (individual genes) from the Ig locus. Thus, one or more VH genes, one or more $D_H$ genes, one or more $J_H$ genes, a mu constant region, and a second constant region (preferably a gamma constant region) are formed into a construct for insertion into an animal. See e.g., U.S. Pat. Nos. 5,545,806; 5,545,807; 5,591,669; 5,612,205; 5,625,825; 5,625,126; 5,633,425; 5,643,763; 5,661,016; 5,721,367; 5,770,429; 5,789,215; 5,789,650; 5,814,318; 5,877; 397; 5,874,299; 6,023,010; and 6,255,458; and European Patent No. 0 546 073 B1; and International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and related family members.

Generation of human antibodies from mice in which, through microcell fusion, large pieces of chromosomes, or entire chromosomes, have been introduced, has also been demonstrated. See European Patent Application Nos. 773 288 and 843 961.

Human anti-mouse antibody (HAMA) responses have led the industry to prepare chimeric or otherwise humanized antibodies. While chimeric antibodies have a human constant region and a immune variable region, it is expected that certain human anti-chimeric antibody (HACA) responses will be observed, particularly in chronic or multi-dose utilizations of the antibody. Thus, it would be desirable to provide fully human antibodies against RANTES in order to vitiate or otherwise mitigate concerns and/or effects of HAMA or HACA response.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit, Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101, 5,585,089, 5, 693, 761, 5,693,792, 5,714,350, and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to RANTES expressing cells, RANTES itself, forms of RANTES, epitopes or peptides thereof, and expression libraries thereto (See e.g., U.S. Pat. No. 5,703,057) which can thereafter be screened as described above for the activities described above.

Design and Generation of Other Therapeutics

In accordance with the present invention and based on the activity of the antibodies that are produced and characterized herein with respect to RANTES, the design of other therapeutic modalities beyond antibody moieties is facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

For example, in connection with bispecific antibodies, bispecific antibodies can be generated that comprise (i) two antibodies one with a specificity to RANTES and another to a second molecule that are conjugated together, (ii) a single antibody that has one chain specific to RANTES and a second chain specific to a second molecule, or (iii) a single chain antibody that has specificity to RANTES and a second molecule. Such bispecific antibodies are generated using techniques that are well known for example, in connection with (i) and (ii) See e.g., Fanger et al. Immunol Methods 4:72-81 (1994) and Wright et al. Crit, Reviews in Immunol. 12125-168 (1992), and in connection with (iii) See e.g., Traunecker et al. Int. J. Cancer (Suppl.) 7:51-52 (1992).

In connection with immunotoxins, antibodies can be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing RANTES.

In connection with the generation of therapeutic peptides, through the utilization of structural information related to RANTES and antibodies thereto, such as the antibodies of the invention or screening of peptide libraries, therapeutic peptides can be generated that are directed against RANTES. Design and screening of peptide therapeutics is discussed in connection with Houghten et al. Biotechniques 13:412-421 (1992), Houghten PNAS USA 82:5131-5135 (1985), Pinalla et al. Biotechniques 13:901-905 (1992), Blake and Litzi-Davis BioConjugate Chem. 3:510-513 (1992). Immunotoxins and radiolabeled molecules can also be prepared, and in a similar manner, in connection with peptidic moieties as discussed above in connection with antibodies. Assuming that the RANTES molecule (or a form, such as a splice variant or alternate form) is functionally active in a disease process, it will also be possible to design gene and antisense therapeutics thereto through conventional techniques. Such modalities can be utilized for modulating the function of RANTES. In connection therewith the antibodies of the present invention facilitate design and use of functional assays related thereto. A design and strategy for antisense therapeutics is discussed in detail in International Patent Application No. WO 94/29444. Design and strategies for gene therapy are well known. However, in particular, the use of gene therapeutic techniques involving intrabodies could prove to be particularly advantageous. See e.g., Chen et al. Human Gene Therapy 5:595-601 (1994) and Marasco Gene Therapy 4:11-15 (1997). General design of and considerations related to gene therapeutics is also discussed in International Patent Application No. WO 97/38137.

Knowledge gleaned from the structure of the RANTES molecule and its interactions with other molecules in accordance with the present invention, such as the antibodies of the invention, and others can be utilized to rationally design additional therapeutic modalities. In this regard, rational drug design techniques such as X-ray crystallography, computer-aided (or assisted) molecular modeling (CAMM), quantitative or qualitative structure-activity relationship (QSAR), and similar technologies can be utilized to focus drug discovery efforts. Rational design allows prediction of protein or synthetic structures which can interact with the molecule or specific forms thereof which can be used to modify or modulate the activity of RANTES. Such structures can be synthesized chemically or expressed in biological systems. This approach has been reviewed in Capsey et al. Genetically Engineered Human Therapeutic Drugs (Stockton Press, NY (1988)). Further, combinatorial libraries can be designed and synthesized and used in screening programs, such as high throughput screening efforts.

Therapeutic Administration and Formulations

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa.

(1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2): 210-8 (2000), Wang W. "Lyophilization and development of solid protein pharmaceuticals." Int. J. Pharm. 203(1-2):1-60 (2000), Charman W N "Lipids, lipophilic drugs, and oral drug delivery—some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The RANTES antagonists, huRANTES antibodies and therapeutic formulations of the invention, which include a RANTES antagonist, such as a huRANTES antibody of the invention, are used to treat or alleviate ischemia, a clinical indication associated with ischemia, reperfusion injury, a symptom associated with an immune-related disorder, such as, for example, an autoimmune disease or an inflammatory disorder.

Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The huRANTES antibodies modulate an immune response in a subject, e.g., in a human subject and transplanted organ. In one embodiment, the RANTES antagonist, huRANTES antibody, fragment thereof or therapeutic formulation thereof is used to treat ischemia, a clinical indication associated with ischemia, reperfusion injury, and/or another immune-related disorder in conjunction with a surgical treatment or other interventional therapy used in the art to treat a given disorder. For example, interventional therapies used in the treatment of ischemia, a clinical indication associated with ischemia, and/or reperfusion injury include surgical intervention or angioplasty. The RANTES antagonist, huRANTES antibody, fragment thereof or therapeutic formulation thereof is administered simultaneously (i.e., during) the interventional therapy, or the RANTES antagonist, huRANTES antibody, fragment thereof or therapeutic formulation thereof is administered at a different time than the interventional therapy. For example, the RANTES antagonist, huRANTES antibody, fragment thereof or therapeutic formulation thereof is administered in some embodiments after an interventional therapy.

In one embodiment, the RANTES antagonist, huRANTES antibody, fragment thereof or therapeutic formulation thereof used to treat ischemia, a clinical indication associated with ischemia, reperfusion injury, and/or another immune-related disorder are administered in combination with any of a variety of anti-cytokine agents or anti-chemokine agents. Suitable anti-cytokine or anti-chemokine reagents recognize, for example, cytokines such as interleukin 1 (IL-1), IL-2, IL-4, IL-6, IL-12, IL-13, IL-15, IL-17, IL-18, IL-20, IL-21, IL-22, IL-23, IL-27 and IL-31, and/or chemokines such as MIP1 alpha, MIP1 beta, RANTES, MCP1, RANTES, ITAC, MIG, SDF and fractalkine.

In one embodiment, the RANTES antagonist, huRANTES antibody, fragment thereof or therapeutic formulation thereof used to treat ischemia, a clinical indication associated with ischemia, reperfusion injury, and/or another immune-related disorder are administered in conjunction with one or more additional agents, or a combination of additional agents. For example, the RANTES antagonist (e.g., huRANTES antibody) and additional agent are formulated into a single therapeutic composition, and the RANTES antagonist and additional agent are administered simultaneously. Alternatively, the RANTES antagonist and additional agent are separate from each other, e.g., each is formulated into a separate therapeutic composition, and the RANTES antagonist and the additional agent are administered simultaneously, or the RANTES antagonist and the additional agent are administered at different times during a treatment regimen. For example, the RANTES antagonist (e.g., huRANTES antibody) is administered prior to the administration of the additional agent, the RANTES antagonist is administered subsequent to the administration of the additional agent, or the RANTES antagonist and the additional agent are administered in an alternating fashion. As described herein, the RANTES antagonist and additional agent are administered in single doses or in multiple doses.

For example, in the treatment of coronary artery disease, the RANTES antagonist, huRANTES antibody, fragment thereof or therapeutic formulation thereof, is administered in conjunction with one or more additional agents such as cholesterol-lowering medicines, such as statins; anticoagulants, such as heparin and/or oral anticoagulants such as warfarin and dicumarol; aspirin, and other antiplatelet medicines; ACE (angiotensin-converting enzyme) inhibitors, such as sulfhydryl-containing ACE inhibitors (e.g., Captopril), dicarboxylate-containing ACE inhibitors (e.g., Enalapril, Ramipril, Quinapril, Perindopril, Lisinopril, Benazepril); phosphonate-containing ACE inhibitors (e.g., Fosinopril); beta blockers; calcium channel blockers; nitroglycerin; long-acting nitrates; glycoprotein IIb-IIIa inhibitors; and thrombolytic agents. The RANTES antagonist and the additional agent are administered simultaneously, or RANTES antagonist and the additional agent are administered at different times during a treatment regimen.

For example, in the treatment of cerebral vascular disease, the RANTES antagonist, huRANTES antibody, fragment thereof or therapeutic formulation thereof, is administered in conjunction with one or more additional agents such as cholesterol-lowering medicines, such as statins, aspirin, and other antiplatelet medicines. The RANTES antagonist and the additional agent are administered simultaneously, or RANTES antagonist and the additional agent are administered at different times during a treatment regimen.

For example, in the treatment of cardiac ischemia, the RANTES antagonist, huRANTES antibody, fragment thereof or therapeutic formulation thereof, is administered in conjunction with one or more additional agents such as aspirin, and other antiplatelet medicines; ACE (angiotensin-converting enzyme) inhibitors, such as sulfhydryl-containing ACE inhibitors (e.g., Captopril), dicarboxylate-containing ACE inhibitors (e.g., Enalapril, Ramipril, Quinapril, Perindopril, Lisinopril, Benazepril); phosphonate-containing ACE inhibitors (e.g., Fosinopril); beta blockers; calcium channel blockers; nitroglycerin; and long-acting nitrates. The RANTES antagonist and the additional agent are administered simultaneously, or RANTES antagonist and the additional agent are administered at different times during a treatment regimen.

For example, in the treatment of myocardial ischemia, the RANTES antagonist, huRANTES antibody, fragment thereof or therapeutic formulation thereof is administered in conjunction with one or more additional agents such as beta blockers; calcium channel blockers; nitroglycerin; and long-acting nitrates. The RANTES antagonist and the additional agent are administered simultaneously, or RANTES antagonist and the additional agent are administered at different times during a treatment regimen.

For example, in the treatment of renal ischemia, the RANTES antagonist, huRANTES antibody, fragment thereof or therapeutic formulation thereof is administered in conjunction with one or more additional agents such as cholesterol-lowering medicines, such as aspirin, and other antiplatelet medicines. The RANTES antagonist and the additional agent are administered simultaneously, or RANTES antagonist and the additional agent are administered at different times during a treatment regimen.

For example, in the treatment of peripheral vascular disease, the RANTES antagonist, huRANTES antibody, fragment thereof or therapeutic formulation thereof is administered in conjunction with one or more additional agents such as anticoagulants, such as heparin and/or oral anticoagulants such as warfarin and dicumarol; aspirin, and other antiplatelet medicines; pentoxifylline; cilostazol; and thrombolytic agents. The RANTES antagonist and the additional agent are administered simultaneously, or RANTES antagonist and the additional agent are administered at different times during a treatment regimen.

For example, in the treatment of multiple sclerosis, the huRANTES antibody, or therapeutic formulation thereof, is administered in conjunction with one or more additional agents such as interferon beta 1a, interferon beta 1b, glatiramer acetate, natalizumab, copaxone, and combinations thereof. The huRANTES antibody and the additional agent are administered simultaneously, or the huRANTES antibody and the additional agent are administered at different times during a treatment regimen.

In the treatment of Crohn's disease, the huRANTES antibody, or therapeutic formulation thereof, is administered in conjunction with one or more additional agents such as an antibiotic, an aminosalicylate, Infliximab, Adalimumab, and combinations thereof. Suitable antibiotics include, e.g., metronidazole and/or ciprofloxacin. Suitable aminosalicylates include, for example, mesalamine and/or sulfasalazine. The huRANTES antibody and the additional agent are administered simultaneously, or the huRANTES antibody and the additional agent are administered at different times during a treatment regimen.

In the treatment of ulcerative colitis, the huRANTES antibody, or therapeutic formulation thereof, is administered in conjunction with one or more additional agents such as 6-mercaptopurine, azathioprine, Infliximab and combinations thereof. The huRANTES antibody and the additional agent are administered simultaneously, or the huRANTES antibody and the additional agent are administered at different times during a treatment regimen.

In the treatment of psoriasis, the huRANTES antibody, or therapeutic formulation thereof, is administered in conjunction with one or more additional agents such as alefacept, efalizumab, Adalimumab, Infliximab, cyclosporine, Methotrexate, and combinations thereof. The huRANTES antibody and the additional agent are administered simultaneously, or the huRANTES antibody and the additional agent are administered at different times during a treatment regimen.

In the treatment of atherosclerosis, the huRANTES antibody, or therapeutic formulation thereof, is administered in conjunction with one or more additional agents such as warfarin, a cholesterol lowering drug, and combinations thereof. Suitable cholesterol lowering drugs include, for example, statins and fibrates. The huRANTES antibody and the additional agent are administered simultaneously, or the huRANTES antibody and the additional agent are administered at different times during a treatment regimen.

The huRANTES antibodies and therapeutic formulations thereof are used in methods of treating or alleviating a symptom associated with an immune-related disorder. For example, the compositions of the invention are used to treat or alleviate a symptom of any of the autoimmune diseases and inflammatory disorders described herein. Symptoms associated with immune-related disorders include, for example, inflammation, fever, loss of appetite, weight loss, abdominal symptoms such as, for example, abdominal pain, diarrhea or constipation, joint pain or aches (arthralgia), fatigue, rash, anemia, extreme sensitivity to cold (Raynaud's phenomenon), muscle weakness, muscle fatigue, changes in skin or tissue tone, shortness of breath or other abnormal breathing patterns, chest pain or constriction of the chest muscles, abnormal heart rate (e.g., elevated or lowered), light sensitivity, blurry or otherwise abnormal vision, and reduced organ function.

The RANTES antagonists, such as a huRANTES antibody, and therapeutic formulations thereof are administered to a subject suffering from ischemia, a clinical indication associated with ischemia, reperfusion injury, and/or an immune-related disorder, such as an autoimmune disease or an inflammatory disorder. A subject or organ suffering from ischemia, a clinical indication associated with ischemia, reperfusion injury, an autoimmune disease or an inflammatory disorder is identified by methods known in the art. For example, subjects are identified using any of a variety of clinical and/or laboratory tests such as, physical examination, radiologic examination and blood, urine and stool analysis to evaluate immune status. For example, patients suffering from lupus are identified, e.g., by using the anti-nuclear antibody test (ANA) to determine if auto-antibodies to cell nuclei are present in the blood. Patients suffering from Crohn's are identified, e.g., using an upper gastrointestinal (GI) series and/or a colonoscopy to evaluate the small and large intestines, respectively. Patients suffering from psoriasis are identified, e.g., using microscopic examination of tissue taken from the affected skin patch, while patients suffering from rheumatoid arthritis are identified using, e.g., blood tests and/or x-ray or other imaging evaluation. Patients suffering from atherosclerosis are identified, e.g., using blood tests, electrocardiograms (ECG), stress testing, coronary angiography, ultrasound, and computed tomography (CT).

Administration of a RANTES antagonist, such as a huRANTES antibody, to a patient suffering from ischemia, a clinical indication associated with ischemia, reperfusion injury, or an immune-related disorder such as an autoimmune disease or an inflammatory disorder is considered successful if any of a variety of laboratory or clinical results is achieved. For example, administration of a huRANTES antibody to a patient suffering from ischemia, a clinical indication associated with ischemia, reperfusion injury, an immune-related disorder such as an autoimmune disease or an inflammatory disorder is considered successful one or more of the symptoms associated with the disorder is alleviated, reduced, inhibited or does not progress to a further, i.e., worse, state. Administration of a huRANTES antibody to a patient suffering from ischemia, a clinical indication associated with ischemia, reperfusion injury, an immune-related disorder such as an autoimmune disease or an inflammatory disorder is considered successful if the disorder, e.g., an autoimmune disorder, enters remission or does not progress to a further, i.e., worse, state.

Diagnostic and Prophylactic Formulations

The fully human anti-RANTES MAbs of the invention are used in diagnostic and prophylactic formulations. In one embodiment, a RANTES antagonist, such as a huRANTES MAb of the invention, is administered to patients that are at risk of developing ischemia, a clinical indication associated with ischemia, reperfusion injury, and/or one of the aforementioned autoimmune diseases. A patient's or organ's predisposition to ischemia, a clinical indication associated with ischemia, reperfusion injury, and/or one or more of the aforementioned autoimmune diseases can be determined using genotypic, serological or biochemical markers.

In another embodiment of the invention, a RANTES antagonist, such as a huRANTES antibody is administered to human individuals diagnosed with a clinical indication associated with ischemia, reperfusion injury, one or more of the aforementioned autoimmune diseases. Upon diagnosis, a RANTES antagonist, such as a huRANTES antibody is administered to mitigate or reverse the effects of the clinical indication associated with ischemia, reperfusion injury, or autoimmunity.

Antibodies of the invention are also useful in the detection of RANTES in patient samples and accordingly are useful as diagnostics. For example, the huRANTES antibodies of the invention are used in in vitro assays, e.g., ELISA, to detect RANTES levels in a patient sample.

In one embodiment, a huRANTES antibody of the invention is immobilized on a solid support (e.g., the well(s) of a microtiter plate). The immobilized antibody serves as a capture antibody for any RANTES that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of RANTES antigen in the test sample is determined by comparison with a standard curve developed from the standard samples.

It will be appreciated that based on the results obtained using the huRANTES antibodies of the invention in an in vitro diagnostic assay, it is possible to stage a disease (e.g., a clinical indication associated with ischemia, an autoimmune or inflammatory disorder) in a subject based on expression levels of the RANTES antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following examples, including the experiments conducted and results achieved are provided for illustrative purposes only and are not to be construed as limiting upon the present invention.

Example 1

Cloning, Expression and Purification of Human RANTES

Cloning

The gene encoding the mature protein human RANTES (GenBank Accession No. M21121) or other chemokines were cloned in an expression plasmid pET43 (Novagen Madison, Wis.) by PCR amplification. The sequence for the Factor X protease cleavage site was introduced at the C-terminus of NusA. The sequence for the AviTag (Avidity, Denver Colo.) biotinylation site was introduced at the C-terminus of the chemokine coding sequence. The pET-derived plasmids were used for the co-transformation of bacterial strain Origami B with pACYC184-BirA plasmid that encodes the biotin ligase gene. For expression in mammalian cells, the gene encoding relevant chemokines were cloned from cDNA in the pEAK8 expression vector (Edge Biosystems, Gaithersburg, Md.). An AviTag biotinylation site was introduced at the C-terminus of the protein followed by an internal ribosome entry site (IRES) allowing for the expression of the BirA gene encoding a biotin ligase. This construct allows for the secreted expression of chemokines biotinylated in vivo at a single site.

Expression of NusA-huRANTES Fusion Protein in E. coli

An overnight culture of bacteria harboring the expression construct was diluted 1:30 into Terrific broth (InvitroGen) containing 50 µg/mL Ampicillin, 10 µg/mL Kanamicin, 5 µg/mL Tetracycline, 20 µg/mL Chloramphenicol and 50 µM Biotin. The culture was incubated at 37° C. with shaking until OD 600=0.7 was reached. IPTG was then added to a final concentration of 1 mM, incubated for 15 min. at 37° C. and overnight at 25° C.

Expression of huRANTES in Mammalian Cells

PEAK cells were cultures in DMEM (Sigma) supplemented with 10% FCS, 2 mM L-Glutamine (Sigma), 25 µg/ml gentamycin (Sigma) and incubated at 37° C., 5% $CO_2$. PEAK cells were transfected with the modified pEAK8 vectors using Mirus transfection reagent. Puromycin (Sigma) was added at 1 µg/ml after cell adherence in order to select and maintain transfected cell populations. Biotin (Sigma) was added to production batches at 50 µM. Biotinylated chemokines from the transfected PEAK cell supernatants were shown to be active in chemotaxis assays.

Purification and Cleavage of Fusion Proteins

Bacterial pellets were resuspended in Bugbuster (Novagen) containing Benzonase Nuclease and protease inhibitor Complete EDTA-free (Roche) and incubated for 1 hour at 4° C. The soluble and insoluble fractions were separated by centrifugation at 10,000 g for 15 min at 4° C. Soluble and insoluble protein fractions were analyzed by SDS-PAGE (Novex gels, InvitroGen). The soluble fraction was diluted ½ with Buffer A (Tris-HCl 100 mM pH 8.0, NaCl 600 mM, $CaCl_2$ 10 mM, Imidazole 40 mM), mixed with 50% (v/v) Ni-NTA agarose (Qiagen) previously equilibrated in Buffer B (Tris-HCl 50 mM pH 8.0, NaCl 300 mM, $CaCl_2$ 5 mM, Imidazole 20 mM). The mixture was incubated for 30 min at RT with gentle shaking. The beads obtained after centrifugation were loaded in Poly-Prep chromatography columns (Biorad), washed three times with 5 volumes of Buffer B and eluted with Buffer C (Tris-HCl 50 mM pH 8.0, NaCl 200 mM, $CaCl_2$ 5 mM, Imidazole 400 mM). Elution fractions containing the protein were pooled and desalted using PD-10 columns (Amersham). NusA-chemokine fusion proteins were cleaved by Factor X (Novagen, Madison, Wis.) by incubating 1 mg protein with 25 U Factor X at 30° C. for up to 24 h in cleavage buffer (Tris-HCl 50 mM pH 8.0, NaCl 200 mM, $CaCl_2$ 5 mM). For some of the fusions proteins, the parameters for optimal cleavage were slightly different but were easily determined by varying incubation time (4-24 h) and/or temperature (25-37° C.). The cleaved protein was analyzed by SDS-PAGE and the activity tested by chemotaxis.

Example 2

Screening of Human scFv Libraries

General procedures for construction and handling of human scFv libraries are described in Vaughan et al., (Nat. Biotech. 1996, 14:309-314), hereby incorporated by reference in its entirety. Libraries of human scFv were screened against huRANTES according to the following procedure.

Liquid Phase Selections.

Aliquots of scFv phage libraries ($10^{12}$ Pfu) obtained from Cambridge Antibody Technology (Cambridge, UK) were blocked with PBS containing 3% (w/v) skimmed milk for one hour at room temperature on a rotary mixer. Blocked phage was then deselected on streptavidin magnetic beads (Dynal M-280) for one hour at room temperature on a rotary mixer. Deselected phage was then incubated with in vivo biotinylated huRANTES (100 nM) for two hours at room temperature on a rotary mixer. This selection step was performed either on NusA-huRANTES biotinylated fusion protein or on biotinylated-huRANTES released from the fusion by proteolytic cleavage. Beads were captured using a magnetic stand followed by four washes with PBS/0.1% Tween 20 and 3 washes with PBS. Beads were then directly added to 10 ml of exponentially growing TG1 cells and incubated for one hour at 37° C. with slow shaking (100 rpm). An aliquot of the infected TG1 was serial diluted to titer the selection output. The remaining infected TG1 were spun at 3000 rpm for 15 minutes and re-suspended in 0.5 ml 2×TY-AG (2×TY media containing 100 µg/ml ampicillin and 2% glucose) and spread on 2×TYAG agar Bioassay plates. After overnight incubation at 30° C. 10 ml of 2×TYAG was added to the plates and the cells were scraped form the surface and transferred to a 50 ml polypropylene tube. 2×TYAG containing 50% glycerol was added to the cell suspension to obtain a final concentration of 17% glycerol. Aliquots of the selection round were kept at −80° C.

Phage Rescue.

100 µl of cell suspension obtained from previous selection rounds were added to 20 ml of 2×TYAG and grown at 37° C. with agitation (240 rpm) until an $OD_{600}$ of 0.3 to 0.5 was reached. The culture was then super-infected with $3.3 \times 10^{10}$ MK13K07 helper phage and incubated for one hour at 37° C. (150 rpm). The medium was then changed by centrifugating the cells at 2000 rpm for 10 minutes, removing the medium and resuspending the pellet in 20 ml of 2×TY-AK (100 µg/ml ampicillin; 50 µg/ml kanamycin). The culture was then grown overnight at 30° C. (240 rpm).

Monoclonal Phage Rescue for ELISA.

Single clones were picked into a microtiter plate containing 150 µl of 2×TYAG media (2% glucose) per well and grown at 37° C. (100-120 rpm) for 5-6 h. M13KO7 helper phage was added to each well to obtain a multiplicity of infection (MOI) of 10 (i.e., 10 phage for each cell in the culture) and incubated at 37° C. (100 rpm) for 1 h. Following growth, plates were centrifuged at 3,200 rpm for 10 min. Supernatant was carefully removed, cells re-suspended in 150 µl 2×TYAK medium and grown overnight at 30° C. (120 rpm). For the ELISA, the phage are blocked by adding 150 µl of 2× concentration PBS containing 5% skimmed milk powder followed by one hour incubation at room temperature. The plates were then centrifuged 10 minutes at 3000 rpm and the phage containing supernatant used for the ELISA.

Phage ELISA.

ELISA plates (Maxisorb, NUNC) were coated overnight with 2 µg/ml NusA-Rantes fusion protein in PBS. Control plates were coated with 2 µg/ml NusA. Plates were then blocked with 3% skimmed milk/PBS at room temperature for 1 h. Plates were washed 3 times with PBS 0.05% Tween 20 before transferring the pre-blocked phage supernatants and incubation for one hour at room temperature. Plates were then washed 3 times with PBS 0.05% Tween 20. 50 µl of 3% skimmed milk/PBS containing (HRP)-conjugated anti-M13 antibody (Amersham, diluted 1:10,000) to each well. Following incubation at room temperature for 1 hr, the plates were washed 5 times with PBS 0.05% Tween 20. The ELISA was then revealed by adding 50 µl of TMB (Sigma) and 50 µl of 2N H$_2$SO$_4$ to stop the reaction. Absorption intensity was read at 450 nm.

Phage Clone Sequencing

Single clones were placed in a microtiter plate containing 150 µl of 2×TYAG media (2% glucose) per well and grown at 30° C. (120 rpm) overnight. The next day 5 µl of culture was transferred into another plate containing 45 µl of dH$_2$O and mixed. The plates was then frozen at −20° C. After thawing, 1 µl of this suspension was used for PCR amplification using standard PCR protocols with primer specific for pCANTAB6: mycseq, 5'-CTCTTCTGAGATGAGTTTTTG-3' (SEQ ID NO: 197) and gene3leader, 5'-TTATTATTCG-CAATTCCTTTAGTTGTTCCT-3' (SEQ ID NO: 198).

The PCR reactions were purified in 96 well format using the Montage PCRµ96 system (Millipore). 5 µl of the eluted DNA was sequencing using the mycseq and gene3leader primers.

ScFv Periplasmic Preparation for Functional Tests.

Individual clones were inoculated into a deep well microtiter plate containing 0.9 ml of 2×TYAG media (0.1% glucose) per well and grown at 37° C. for 5-6 h (250 rpm). 100 µl per well of 0.2 mM IPTG in 2×TY medium were then added to give a final concentration of 0.02 mM IPTG. Plates were then incubated overnight at 30° C. with shaking at 250 rpm. The deep-well plates were centrifuged at 2,500 rpm for 10 min and the supernatant carefully removed. The pellets were re-suspended in 150 µl TES buffer (50 mM Tris/HCl (pH 8), 1 mM EDTA (pH 8), 20% sucrose, complemented with Complete protease inhibitor, Roche). A hypotonic shock was produced by adding 150 µl of diluted TES buffer (1:5 TES:water dilution) and incubation on ice for 30 min. Plates were then centrifuged at 4000 rpm for 10 minutes to remove cells and debris. The supernatants were carefully transferred into another microtiter plate and kept on ice for immediate testing in functional assays or ELISAs.

Large Scale scFv Purification

A starter culture of 1 ml of 2×TYAG was inoculated with a single colony from a freshly streaked 2×TYAG agar plate and incubated with shaking (240 rpm) at 37° C. for 5 hours. 0.9 ml of this culture was used to inoculate a 400 ml culture of the same media and was grown overnight at 30° C. with vigorous shaking (300 rpm).

The next day the culture was induced by adding 400 µl of 1M IPTG and incubation was continued for an additional 3 hours. The cells were collected by centrifugation at 5,000 rpm for 10 minutes at 4° C. Pelleted cells were resuspended in 10 ml of ice-cold TES buffer complemented with protease inhibitors as described above. Osmotic shock was achieved by adding 15 ml of 1:5 diluted TES buffer and incubation for 1 hour on ice. Cells were centrifuged at 10,000 rpm for 20 minutes at 4° C. to pellet cell debris. The supernatant was carefully transferred to a fresh tube. Imidazole was added to the supernatant to a final concentration of 10 mM. 1 ml of Ni-NTA resin (Qiagen), equilibrated in PBS was added to each tube and incubated on a rotary mixer at 4° C. (20 rpm) for 1 hour.

The tubes were centrifuged at 2,000 rpm for 5 minutes and the supernatant carefully removed. The pelleted resin was resuspended in 10 ml of cold (4° C.) Wash buffer 1 (50 mM NaH$_2$PO$_4$, 300 mM NaCl, 10 mM imidazole, pH to 8.0). The suspension was added to a polyprep column (Biorad). 8 ml of cold Wash Buffer 2 (50 mM NaH$_2$PO$_4$, 300 mM NaCl, 20 mM imidazole, pH to 8.0) were used to wash the column by gravity flow. The scFv were eluted from the column with 2 ml of Elution buffer (50 mM NaH$_2$PO$_4$, 300 mM NaCl, 250 mM imidazole, pH to 8.0). Fractions were analyzed by absorption at 280 nm and protein containing fractions were pooled before buffer exchange on a PD10 desalting column (Amersham) equilibrated with PBS. The scFv in PBS were analyzed by SDS-PAGE and quantified by absorption at 280 nm. The purified scFv were aliquoted and stored at −20° C. and at 4° C.

Example 3

Inhibition of huRANTES Induced Calcium Flux Using scFv Extracts

Periplasmic extracts of various huRANTES scFv were produced as described above. L1.2 cells expressing hCCR5 were cultured in RPMI medium supplemented with 10% FCS. Extracts containing the scFv were incubated with 2-10 nM of huRANTES (Peprotech, Rocky Hill N.J.) for 30 minutes at room temperature. Cells were washed in PBS and loaded with 2 µM Fura 2/AM. 100 µl of loaded cells were added to each well of a 96-well black, transparent flat-bottom plate and calcium flux kinetics were recorded by measuring the fluorescence at 514 nm upon excitation at 340 or 380 nm on a Flex station II instrument (Molecular Devices) upon addition of the chemokine scFv mix. The inhibitory activity of each scFv extract was assessed by comparison to an extract containing an irrelevant scFv.

Example 4 scFv Inhibition of huRANTES-Induced Cell Chemotaxis

Wild type L1.2 cells and L1.2 cells expressing hCCR5 were cultured in RPMI medium supplemented with 10% FCS. The day before the experiment cells were incubated with 0.6 mg/ml of butyric acid. Different concentrations of purified scFv were incubated with 0.2-10 nM huRANTES and placed in the bottom chamber of chemotaxis 96-well plate (Neuroprobe). The filter plate was placed on top of the chemotaxis plate and each well was overlaid with 20 µl of a 10$^6$ cells/ml suspension. The plate was incubated for 2 hours at 37° C. Cells that migrated through the filter were stained with DRAQ5 (Alexis Corporation) and counted on an FMAT 8200 reader (Applied Biosystems, Foster City Calif.). The IC$_{50}$ (where 50% of the huRANTES induced cell migration is inhibited, i.e., 50% inhibitory concentration), for each candidate antibody was determined (Table 4).

TABLE 4

Potency of antibodies tested in scFv format in chemotaxis functional assays.
Chemotaxis was performed using 1 nM. of huRANTES,

| Clone ID | Chemotaxis IC$_{50}$ (nM) |
|---|---|
| CG11 | 3.6 |
| BG11 | 7 |
| A9 | 72 |
| E6 | 72 |
| H6 | 25 |
| G2 | 62 |
| E10 | 9.4 |
| C10 | 41 |
| 2D1 | 1.3 |
| A5 | 21 |
| H11 | 4.3 |
| D1 | 22 |
| E7 | 3.8 |
| C8 | 90 |
| 1D9 | 0.82 |

TABLE 4-continued

Potency of antibodies tested in scFv format
in chemotaxis functional assays.
Chemotaxis was performed using 1 nM. of huRANTES.

| Clone ID | Chemotaxis IC$_{50}$ (nM) |
| --- | --- |
| 1E4 | 1.25 |
| 3E7 | 0.47 |
| 4D8 | 0.08 |
| 5E1 | 0.2 |
| 6A8 | 0.94 |
| 7B5 | 1.6 |

Example 5

Reformatting scFv into IgG Format

The V$_H$ and V$_L$ sequence of selected scFv were amplified with specific oligonucleotides introducing a leader sequence and a HindIII restriction site at the 5' end. An ApaI or an AvrII site was introduced at the 3' end of the heavy and light chain sequence, respectively. The amplified V$_H$ sequences were digested HindIII/ApaI and cloned into the pCon_gamma1 expression vector (LONZA, Basel, Switzerland). The amplified V$_L$ sequences were digested HindIII/AvrII and cloned into the pCon_lambda2 expression vector (LONZA). The constructions were verified by sequencing before transfection into mammalian cells.

The V$_H$ and V$_L$ cDNA sequences in their appropriate expression vectors were transfected into mammalian cells using the Fugene 6 Transfection Reagent (Roche, Basel, Switzerland). Briefly, Peak cells were cultured in 6-well plates at a concentration of 6×10$^5$ cells per well in 2 ml culture media containing fetal bovine serum. The expression vectors, encoding the candidate V$_H$ and V$_L$ sequences, were co-transfected into the cells using the Fugene 6 Transfection Reagent according to manufacturer's instructions. One day following transfection, the culture media was aspirated, and 3 ml of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE.

Example 6

Production of Native Human huRANTES

THP1 cells were cultured in 10 ml media at a concentration at 1×10$^6$/ml with 10 μg/ml LPS. Following overnight incubation at 37° C., cells were centrifuged, supernatant was collected and the concentration of native huRANTES was estimated in a chemotaxis assay as described in Example 4. Not only native huRANTES but also other ligands of CCR5 are produced by THP1 cells when stimulated with LPS as described above. Therefore, when using these supernatants in chemotaxis assays to determine the neutralization potential of anti-huRANTES antibodies, the other ligands of CCR5 were neutralized with a mixture of antibodies against hMIP-1α, hMIP-1β, hMCP-2, hMIP-1δ each at a concentration of 5 μg/ml (R&D Systems).

Example 7

Figure 1B:
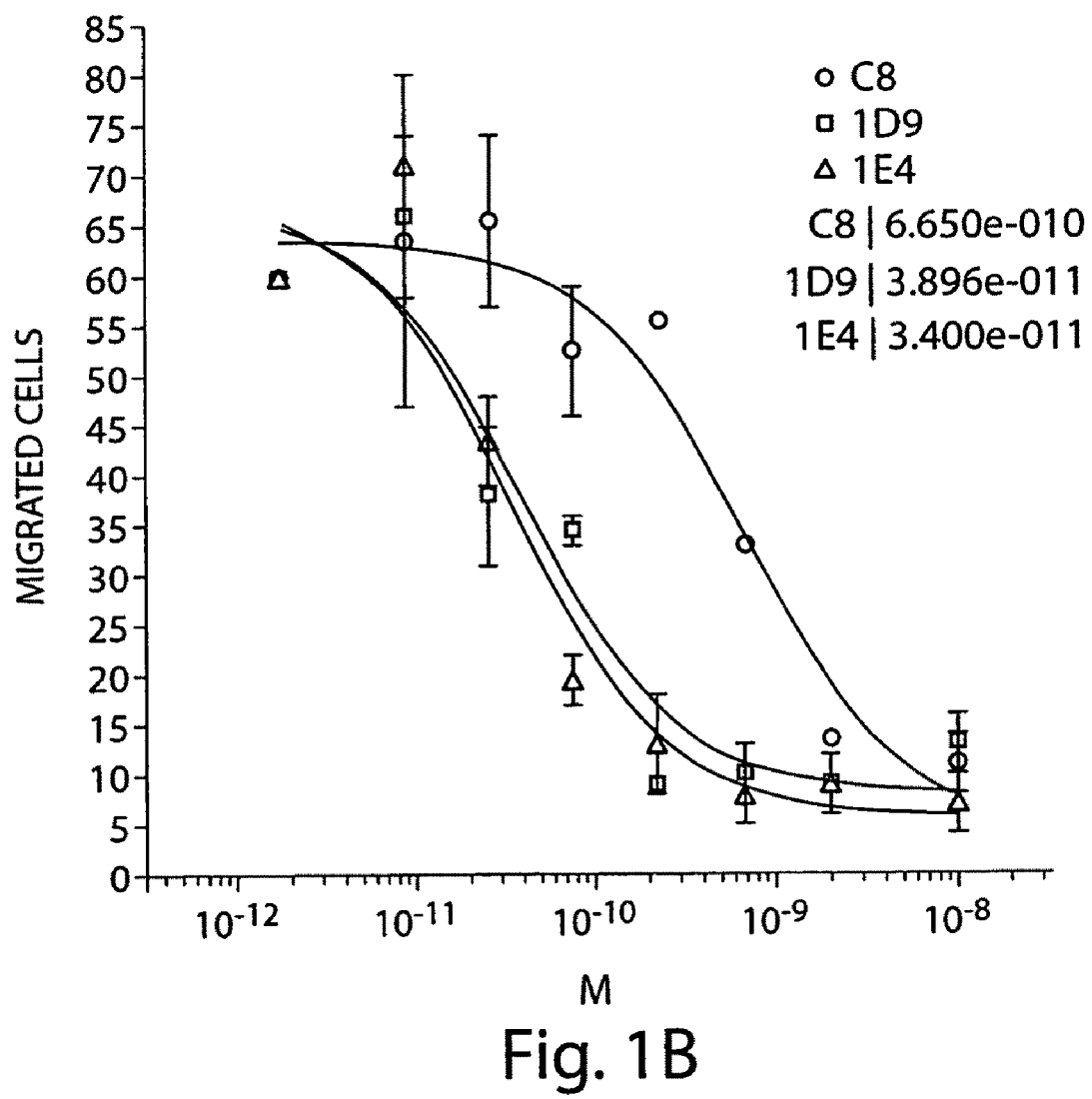
Figure 1C:
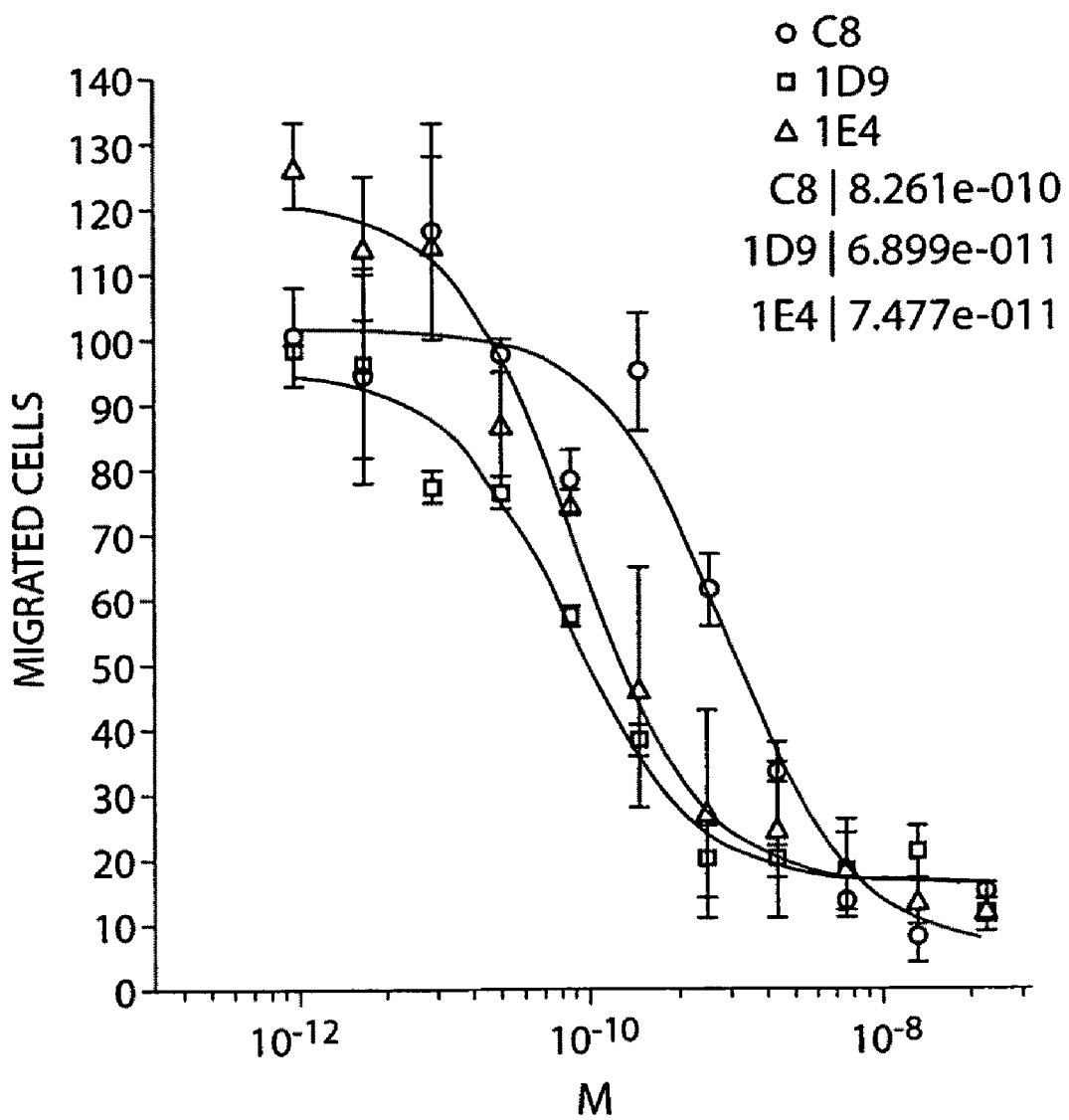

Inhibition of huRANTES-Induced Calcium Flux or Cell Chemotaxis Using Reformatted scFv into IgG1 Format scFv were reformatted into an IgG format as described above in Example 5. The neutralizing potential of the IgG on huRANTES-induced calcium flux or cell chemotaxis was evaluated using the cell-based assays described in Example 3 and 4. As shown as examples in FIG. 1 IgGs C8, 1D9 and 1E4 inhibit the activity of both recombinant and native huRANTES in a dose-dependent manner. The IC$_{50}$ values in these assays for all antibodies are summarized in Tables 5 and 6.

TABLE 5

Potency of antibodies tested in IgG1 format in chemotaxis and
calcium flux functional assays. Chemotaxis was performed using
either 1 nM or 0.2 nM of recombinant huRANTES while calcium flux
was induced with 10 nM of recombinant huRANTES.

| Clone ID | Chemotaxis IC$_{50}$ (nM) 1 nM huRANTES | Chemotaxis IC$_{50}$ (nM) 0.2 nM huRANTES | Calcium Flux IC$_{50}$ (nM) rhuRANTES |
| --- | --- | --- | --- |
| CG11 | 4.8 | ND | 9.5 |
| BG11 | 29 | ND | 7.7 |
| A9 | 1 | ND | 3.3 |
| E6 | 14 | ND | 12.7 |
| H6 | 8.7 | ND | 9 |
| G2 | 18.4 | ND | ND |
| E10 | 16 | ND | ND |
| C10 | 17 | ND | ND |
| 2D1 | 1.7 | 1.3 | ND |
| A5 | 13.2 | ND | ND |
| H11 | 1.3 | ND | ND |
| D1 | 7 | ND | ND |
| E7 | 2.2 | ND | ND |
| C8 | 2.1 | 0.49 | ND |
| 1D9 | 0.35 | 0.038 | ND |
| 1E4 | 0.46 | 0.034 | ND |
| 3E7 | 0.68 | 0.25 | ND |
| 4D8 | 1.16 | 0.22 | ND |
| 5E1 | 0.82 | 0.25 | ND |
| 6A8 | 0.74 | 0.31 | ND |
| 7B5 | 1.1 | 0.31 | ND |

TABLE 6

Potency of antibodies tested in IgG1 format in chemotaxis
functional assay performed using native human RANTES produced
by THP1 cells at a concentration of <1 nM.

| Clone ID | Chemotaxis IC$_{50}$ (nM) >1 nM native huRANTES |
| --- | --- |
| C8 | 1.6 |
| 1D9 | 0.033 |
| 1E4 | 0.028 |

Example 8

Antibody Binding to huRANTES Immobilized on Glycosaminoglycan

Figure 2:
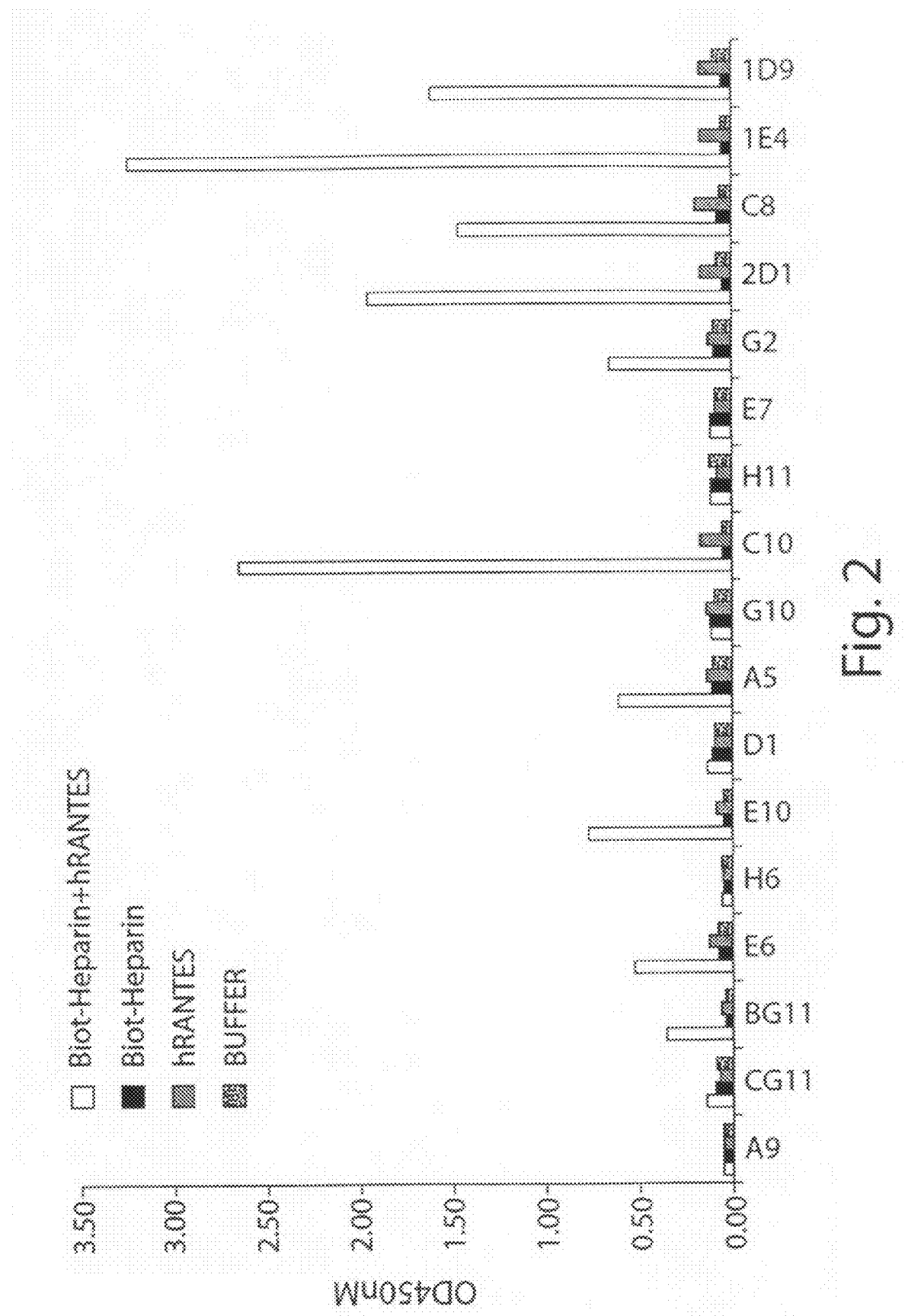
FIG. 2 is a graph depicting the capacity of anti-huRANTES antibodies to bind to huRANTES in the context of glycosaminoglycans in and ELISA assay.

As with many chemokines, huRANTES is able to oligomerize and bind to glycosaminoglycans (GAG) expressed at surface of cells such as endothelial cells. In order to make sure that the antibodies were able to bind to huRANTES in this context, they were tested in the following assay. Streptavidin coated 96 well plates (Roche, Basel, Switzerland) were coated with biotin labeled heparin as a prototypic GAG (Sigma, St. Louis, Mo.). After washing the excess heparin huRANTES was added the wells for immobilization GAG. After incubation with the antibodies to be tested, the wells were washed and binding was revealed with an anti-human IgG Fcg specific antibody coupled to HRP (Jackson, West Grove, Pa.). As shown in FIG. 2 some antibodies were able to bind huRANTES when bound to GAG whereas others were unable to do so probably because their epitope on huRANTES was no longer accessible within the oligomeric structure. The capacity of the antibodies to bind huRANTES in the context of GAG is summarized in Table 7.

TABLE 7

Ability of antibodies to bind to huRANTES immobilized on GAG.

| Clone ID | Binding to huRANTES immobilized on GAGs |
|---|---|
| CG11 | No |
| BG11 | Yes |
| A9 | No |
| E6 | Yes |
| H6 | No |
| G2 | Yes |
| E10 | Yes |
| C10 | Yes |
| 2D1 | Yes |
| A5 | Yes |
| H11 | No |
| D1 | No |
| E7 | No |
| C8 | Yes |
| 1E4 | Yes |
| 1D9 | Yes |

Example 9

Affinity Maturation of Antibody 2D1

A selected lead candidate (2D1) was subjected to affinity maturation in order to increase its affinity for huRANTES and its potency in huRANTES neutralization assays. Stretches of 5 residues in the CDR3 of the heavy or light chain were randomized in order to generate 6 libraries (Library size ranging from $5 \times 10^7$ to $10^9$). Three high stringency selection rounds were performed as described in Example 2. Screening for improved variant was performed using scFv periplasmic extracts in an epitope competition assay. Briefly, the parent antibody (2D1) was coated on plates and diluted periplasmic scFv extracts were added to each well. Biotinylated huRANTES was then added and incubated for 2 hours at room temperature. After washing, huRANTES remaining bound to the coated parent antibody was revealed using streptavidin coupled HRP (Jackson, West Grove Pa.). As a reference to identify improved variants 2D1 scFv was used to compete coated 2D1 in an IgG format.

Example 10

Generation of a Stable CHOK1SV Cell Line Expressing 1E4

The CHOK1SV cell line, property of Lonza Biologics, plc, was used to generate pools through semi-stable transfection for the production of the antibody 1E4. Briefly, exponentially growing cells in the medium CD-CHO (Invitrogen) supplemented with 6 mM of L-glutamine, were electroporated under the following conditions: in a 0.4 cm cuvette, $1.0 \times 10^7$ viable cells in 700 μL of fresh CD-CHO were gently mixed with 40 μg of DNA in 100 μL of Tris EDTA buffer solution, pH 7.4, immediately followed by delivering of a single pulse of 300 volts, 900 μF. The contents of 2 cuvettes were immediately transferred in 200 mL of fresh pre-warmed CD-CHO medium. This cell suspension was subsequently distributed in 4 tissue culture-treated T75 flasks and placed in a humidified incubator set at 10% $CO_2$ in air and a temperature of 37° C. to generate semi-stable pools. Around twenty-four hours after transfection, selective pressure (by MSX supplementation at 50 μM) was applied. Individual stably transfected clones were then selected using ClonePix technology (Genetix) and screened for 1E4 productivity.

Example 11

Large Scale Purification of 1E4 from CHO Supernatant

The process involves MabSelect SuRe affinity chromatography (GE Healthcare), retrovirus inactivation by low pH treatment, pH adjustment for SP Sepharose cation exchange chromatography, concentration/diafiltration before Capto Q (GE Healthcare) anion exchange chromatography and concentration/diafiltration into final formulation buffer.

Briefly, supernatant produced by 25 L Wave Bag fermentation of clone was clarified and captured on MabSelect SuRe Protein A Affinity column with an overall recovery of 95% at 80% of the maximum loading capacity (32 mg of Antibody per mL of matrix). The eluate was proven to be stable at elution pH up to 48 h. The stability of the 1E4 antibody was also evaluated at the low pH (3.7) used for viral inactivation and the Antibody was stable up to 48 h.

The pool of Protein A eluates was then loaded onto an SP Sepharose cation exchange column after pH adjustment (pH 5). This step was optimised for efficient residual aggregate removal, the optimal elution buffer was found to be 107 mM Sodium Chloride (in 25 mM Sodium Acetate pH 5). A concentration/diafiltration step was then used to buffer exchange the 1E4 antibody into the appropriate buffer for Capto Q Chromatography (25 mM Sodium Acetate, 40 mM Sodium Chloride pH 5). A concentration of about 50 mg/mL was reached without any problems of degradation or aggregation. The Capto Q Chromatography in non-binding mode was optimised for efficient contaminant removal (Host Cell Proteins, Protein A and DNA). Antibody 1E4 was finally concentrated and diafiltered into the 25 mM Histidine, 125 mM NaCl, pH 6 formulation buffer to a final concentration of about 10 mg/mL.

Antibody 1E4 did not show a tendency to aggregate throughout the purification process, and presented good stability across the purification process. The final product reached all prerequisite specifications in terms of aggregates levels and residual contamination.

Example 12

Functional Characterization of Antibody 1E4 Purified Form CHO Supernatant

RANTES is a ligand for the receptors CCR1, CCR3 and CCR5. The capacity of 1E4 purified from CHO supernatants to block the interaction with each one of these receptors was assessed in chemotaxis and calcium flux assays.

Calcium Flux

Figure 3A:
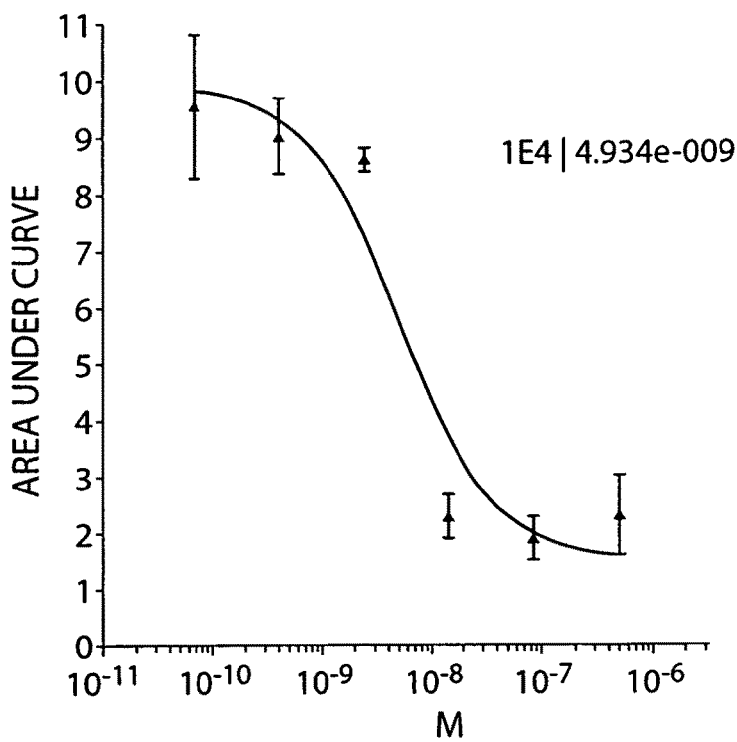
FIG. 3 is a series of graphs depicting the activity of anti-huRANTES antibody 1E4 in calcium flux assays using: L1.2 cells expressing hCCR1 and 25 nM recombinant human RANTES (FIG. 3A); L1.2 cells expressing hCCR3 and 25 nM recombinant human RANTES (FIG. 3B); L1.2 cells expressing hCCR5 and 4 nM recombinant human RANTES (FIG. 3C).
Figure 3B:
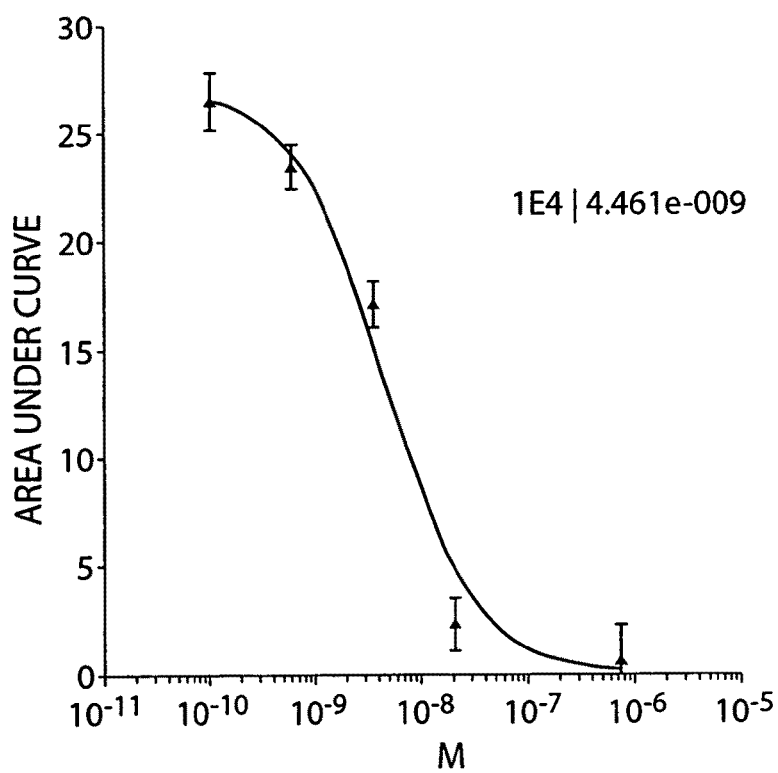
Figure 3C:
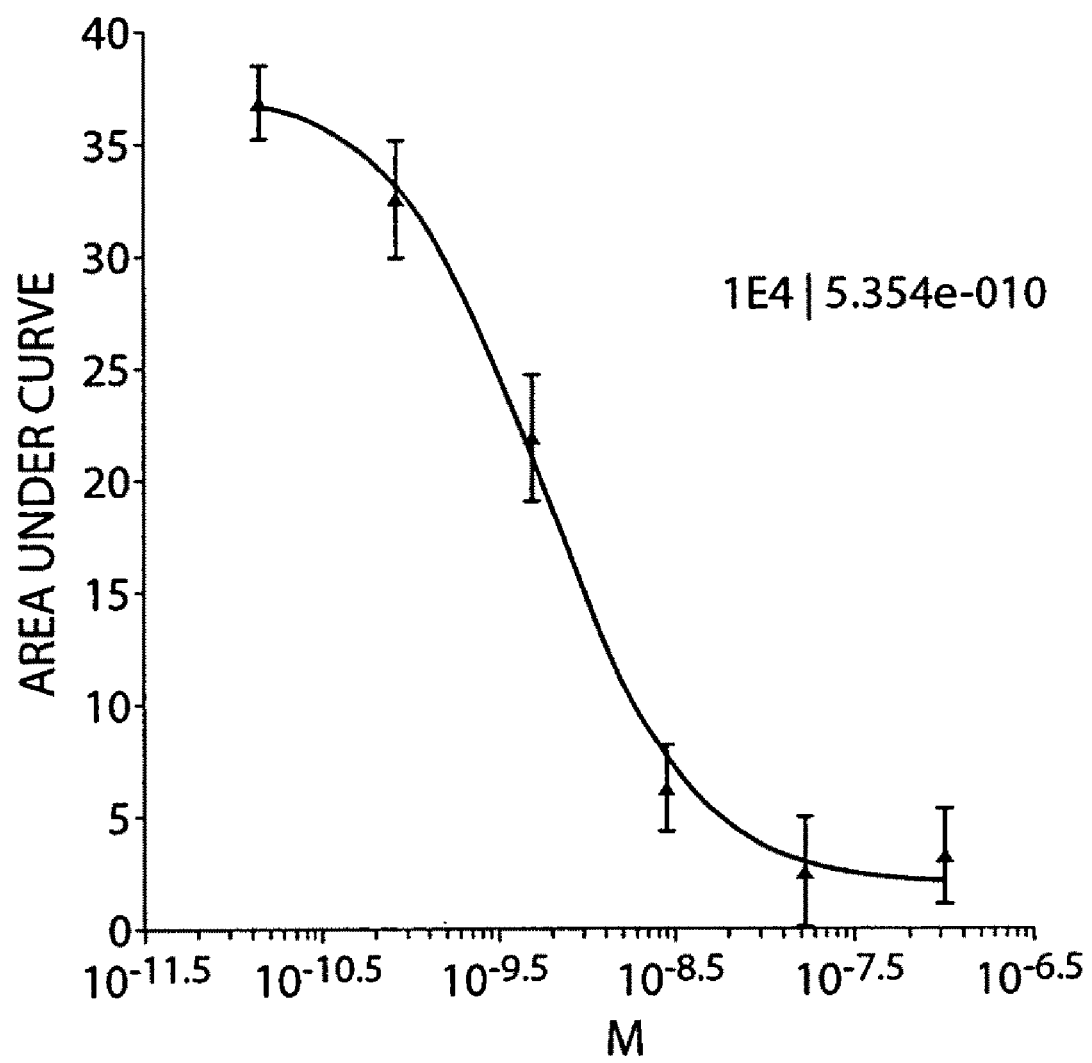
Figure 4A:
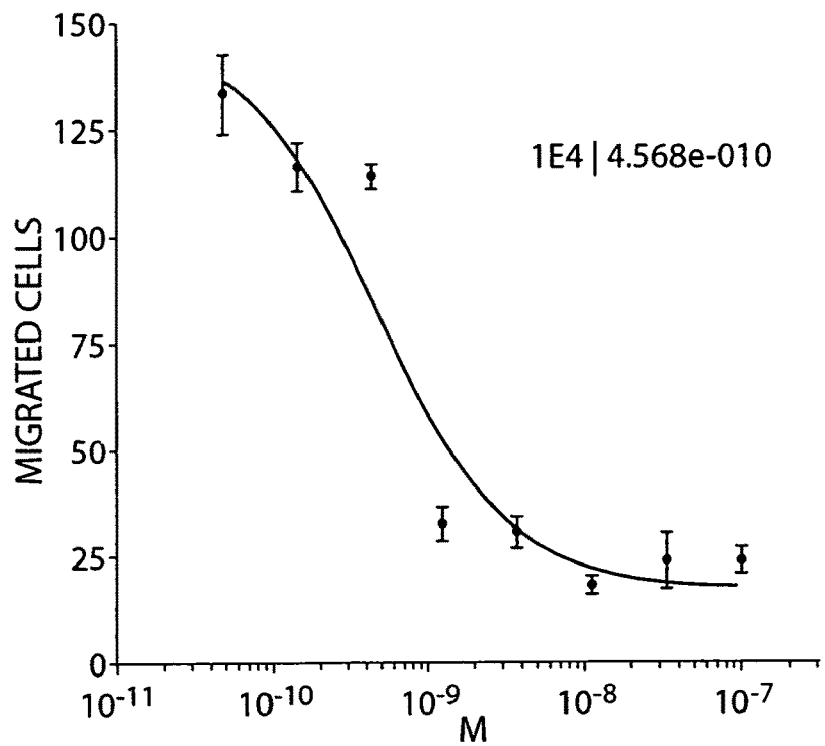
FIG. 4 is a series of graphs depicting the activity of anti-huRANTES antibody 1E4 in chemotaxis assays using: L1.2 cells expressing hCCR1 and 2 nM of recombinant human RANTES (FIG. 4A); L1.2 cells expressing hCCR3 and 10 nM of recombinant human RANTES (FIG. 4B); L1.2 cells expressing hCCR5 and 1 nM of recombinant human RANTES (FIG. 4C); L1.2 cells expressing hCCR5 and about 1 nM of native human RANTES (FIG. 4D).
Figure 4B:
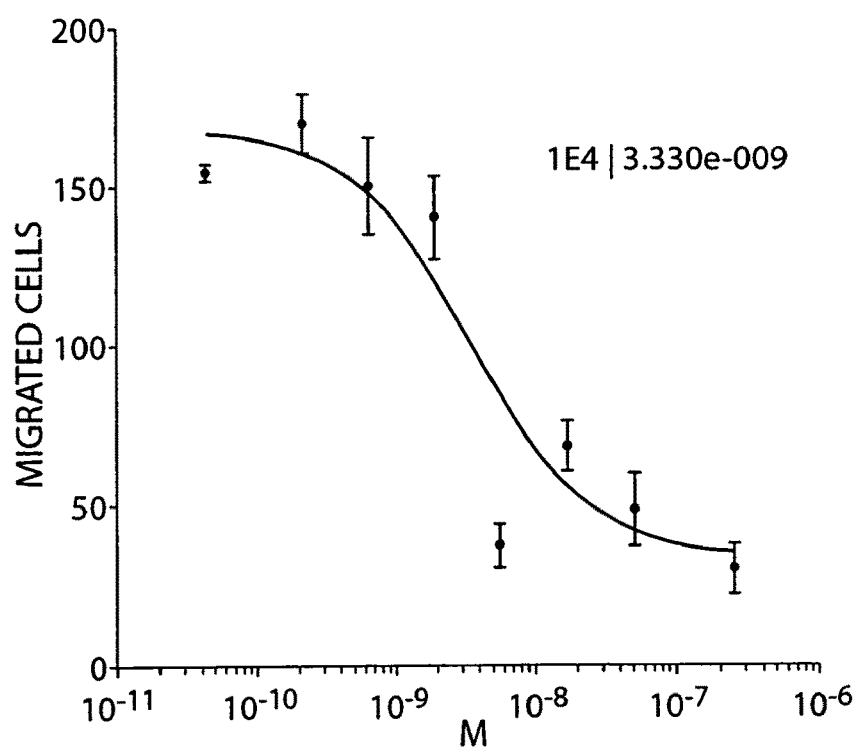
Figure 4C:
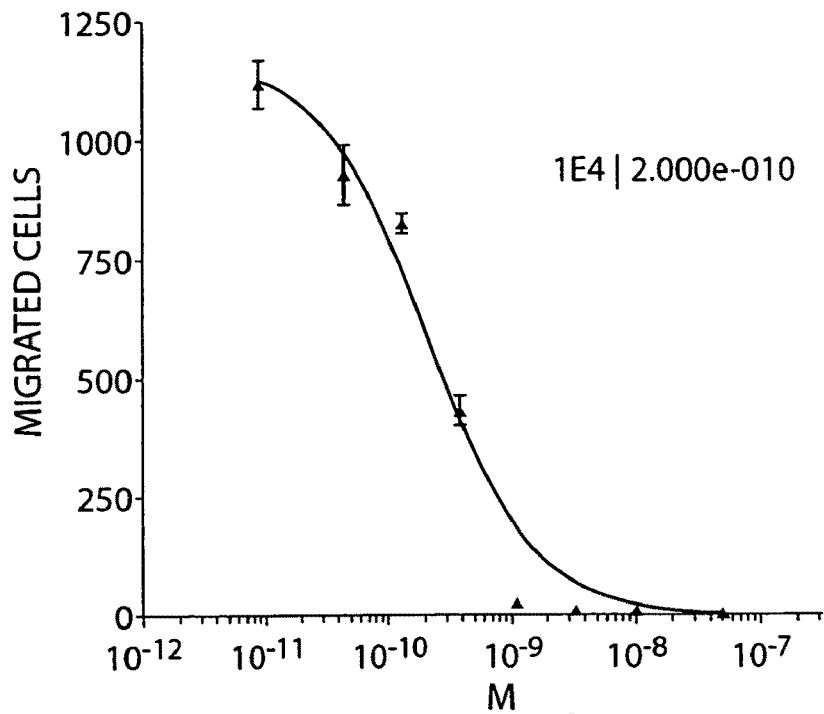
Figure 4D:
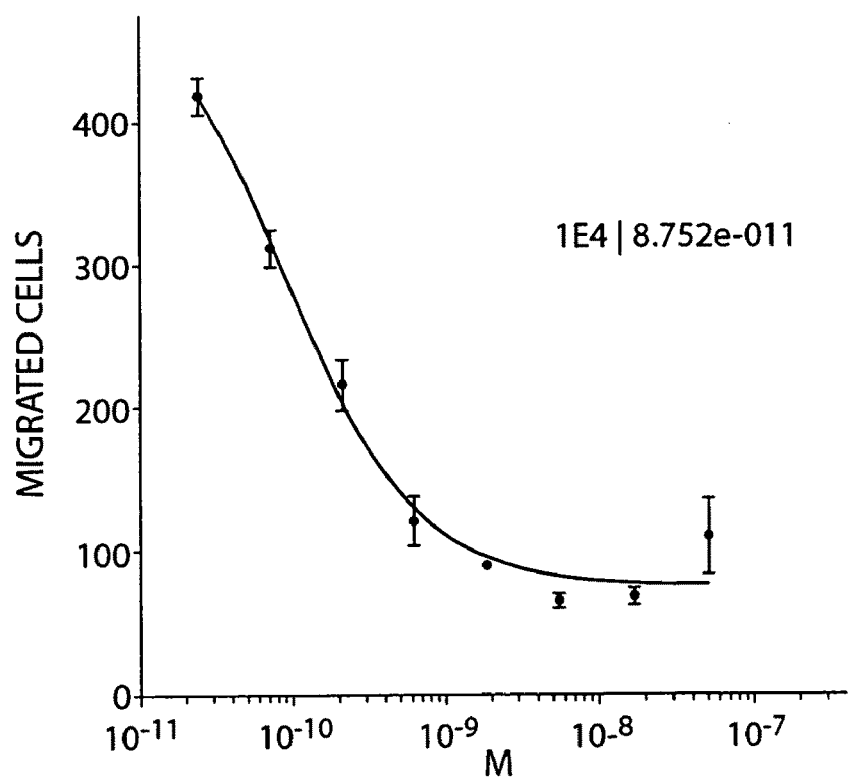

L1.2 cells expressing either hCCR1, hCCR3 or hCCR5 were cultured in RPMI medium supplemented with 10% FCS. For optimal results, cells expressing hCCR1 were starved overnight in medium containing 1% of FCS. The day before the experiment all cells were incubated with 0.3 mg/ml of butyric acid. Different concentrations of 1E4 were incubated with 4 to 25 nM of huRANTES (Peprotech, Rocky Hill N.J.) for 30 minutes at room temperature. Cells were washed in PBS and loaded with 2 µM Fura 2/AM. 100 µl of loaded cells were added to each well of a 96-well black, transparent flat-bottom plate and calcium flux kinetics were recorded by measuring the fluorescence at 514 nm upon excitation at 340 or 380 nm on a Flex station II instrument (Molecular Devices) after addition of the chemokine-antibody mix. As shown in FIG. 3, 1E4 was able to inhibit calcium flux in cells that express either hCCR1, hCCR3 or hCCR5 in a dose dependent manner. The $IC_{50}$ (where 50% of the huRANTES induced calcium flux is inhibited, i.e., 50% inhibitory concentration) was determined (Table 8).

TABLE 8

Potency of antibody 1E4 purified from CHO supernatant in calcium flux functional assay using cells expressing the one three cognate receptors of RANTES.

| Cells and concentration of huRANTES used for calcium flux induction | $IC_{50}$ (nM) |
| --- | --- |
| L1.2-hCCR1; 25 nM huRANTES | 4.9 |
| L1.2-hCCR3; 25 nM huRANTES | 4.46 |
| L1.2-hCCR5; 4 nM huRANTES | 0.54 |

Chemotaxis

Wild type L1.2 cells and L1.2 cells expressing either hCCR1, hCCR3 or hCCR5 were cultured in RPMI medium supplemented with 10% FCS. For optimal results, cells expressing hCCR1 were starved overnight in medium containing 1% of FCS. The day before the experiment all cells were incubated with 0.3 mg/ml of butyric acid. For optimal results, cells expressing hCCR1 were starved overnight in medium containing 1% of FCS. Different concentrations of 1E4 were incubated with 1-10 nM of recombinant huRANTES or 1 nM of native huRANTES (generated as described in example 6) and placed in the bottom chamber of chemotaxis 96-well plate (Neuroprobe). The filter plate was placed on top of the chemotaxis plate and each well was overlaid with 20 µl of a $10^6$ cells/ml suspension. The plate was incubated for 2 hours at 37° C. Cells that migrated through the filter were stained with DRAQ5 (Alexis Corporation) and counted on an FMAT 8200 reader (Applied Biosystems, Foster City Calif.). As shown in FIG. 4, 1E4 was able to inhibit calcium flux in cells that express either hCCR1, hCCR3 or hCCR5 in a dose dependent manner. The $IC_{50}$ (where 50% of the huRANTES induced cell migration is inhibited, i.e., 50% inhibitory concentration) was determined (Table 9).

TABLE 9

Potency of antibody 1E4 purified from CHO supernatant in chemotaxis functional assay using cells expressing the one three cognate receptors of RANTES.

| Cells and concentration of huRANTES used for chemotaxis assays | $IC_{50}$ (nM) |
| --- | --- |
| L1.2-hCCR1; 2 nM huRANTES | 0.46 |
| L1.2-hCCR3; 10 nM huRANTES | 3.33 |
| L1.2-hCCR5; 1 nM huRANTES | 0.2 |
| L1.2-hCCR5; 1 nM native huRANTES | 0.09 |

Example 13

Cross-Reactivity of 1E4 Antibody

Figure 5:
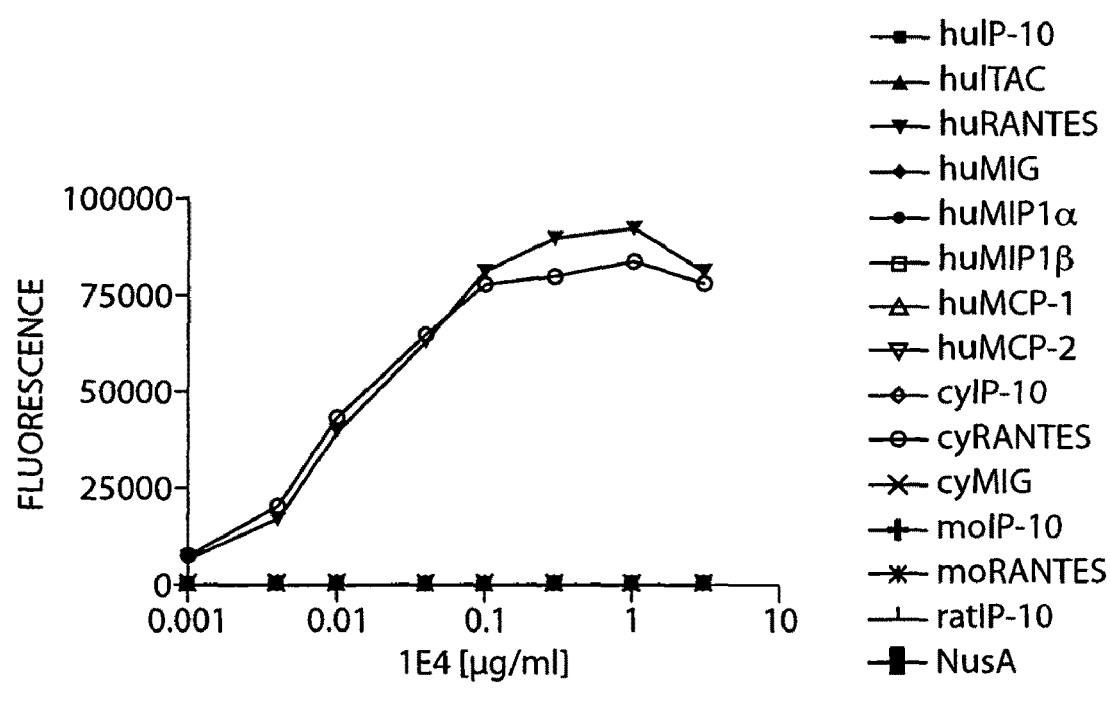
FIG. 5 is a graph depicting the cross-reactivity profile of antibody 1E4 against a panel of human, cynomolgus, mouse and rat chemokines in an ELISA.

1E4 was tested for its ability to bind to a panel of chemokines from different species in an ELISA. The panel included the following chemokines: human RANTES, cynomolgus monkey RANTES, rat RANTES, mouse RANTES, human ITAC, human IP-10, cynomolgus monkey IP-10, human MIG, cynomolgus monkey MIG, human MIP1α, human MIP1β, human MCP-1, human MCP-2. Briefly, chemokines cloned from cDNA isolated from human, mouse, rat, and cynomolgus monkey were expressed as fusion proteins and purified as described in Example 1. The chemokines were coated at 5 µg/ml in an maxisopb plate (Nunc, Denmark) and incubated with a concentration range of 1E4. The level of binding was revealed using an anti-human Fc-γ specific antibody coupled to horse radish peroxidase (Jackson) and a fluorescent substrate. As shown in FIG. 5, the antibody 1E4 only binds to human and cynomolgus RANTES and not with RANTES from other species nor with any of the other human chemokines tested. Proper coating of all the chemokines was controlled using monoclonal antibodies directed against each chemokine and all the chemokines tested could be detected in this format.

Example 14

Epitope Mapping of 1E4 Antibody

Figure 6:
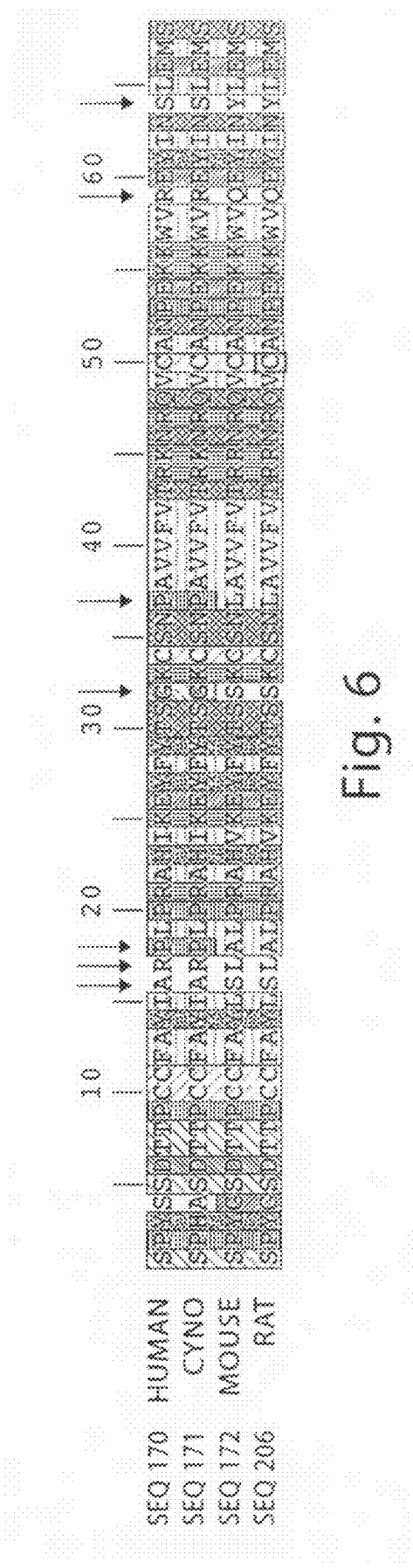
FIG. 6 is a sequence alignment of mature RANTES protein from human (SEQ ID NO: 170), cynomolgus monkey (SEQ ID NO: 171), mouse (SEQ ID NO: 172) and rat (SEQ ID NO: 206). The arrows indicate positions that are conserved in human and cynomolgus RANTES but not in the mouse or rat sequences and that were targeted by site-directed mutagenesis.
Figure 7:
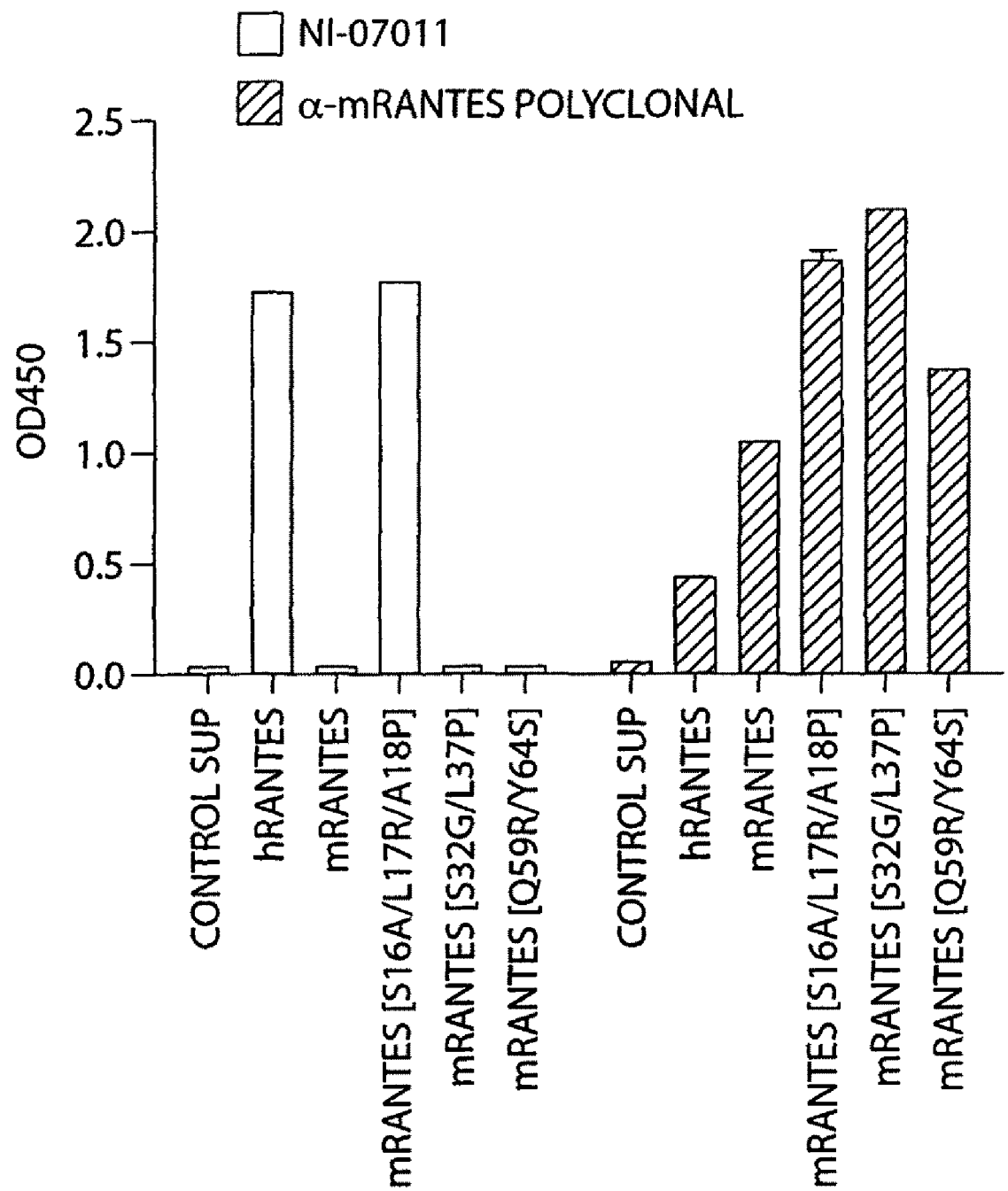
FIG. 7 is a graph depicting the binding of antibody 1E4 (open bars) or of a polyclonal antibody raised against mouse RANTES (hatched bars) to human RANTES, mouse RANTES and variants of mouse RANTES in which the indicated mouse amino acids have been replaced by the amino acids found in the human sequence at the same position.
Figure 8:
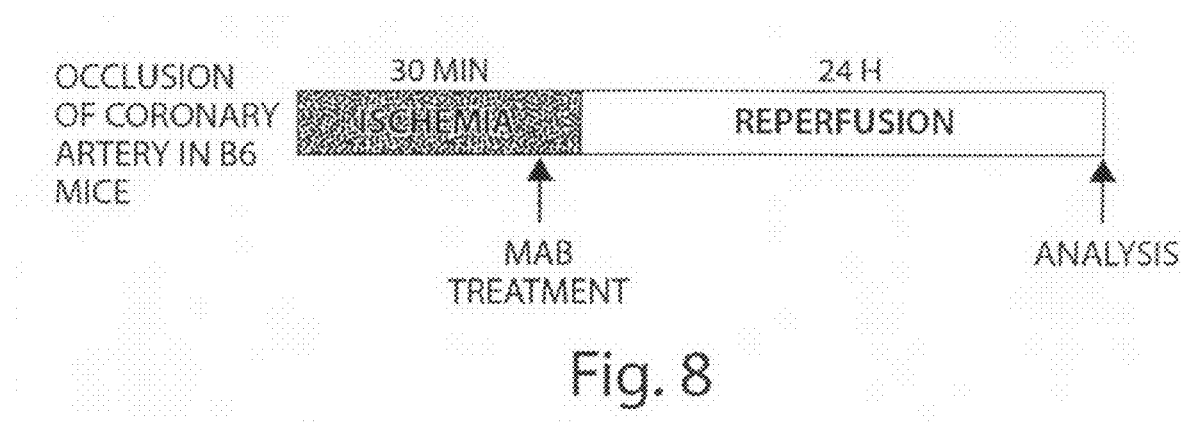
FIG. 8 is an illustration depicting the protocol of a murine ischemia reperfusion model provided herein.

In an ELISA, the antibody 1E4 binds with equivalent apparent affinity to both human and cynomolgus RANTES (FIG. 5). In order to identify residues potentially required on huRANTES for binding to 1E4, the RANTES protein sequences from several species were aligned as shown in FIG. 6. In the alignment, residues that are conserved between the human and cynomolgus sequences and that are different in mouse and rat RANTES to which 1E4 is unable to bind were analyzed to identify the following amino acids: A16, R17, P18, G32, P37, R59 and S64. Three mutants of mouse RANTES were generated by site directed mutagenesis in order to introduce the human residues at those positions: [S16A/L17R/A18P]; [S32G/L37P] and [Q59R/Y64S]. These mutant forms of mouse RANTES were expressed and biotinylated in vivo as described in Example 1. These variant of mouse RANTES were captured in streptavidin coated plates (Streptawell, Roche). The coating of the biotinylated chemokine was confirmed using a anti-mouse RANTES polyclonal antibody (R&D Systems). It was then tested whether the introduction of these residues could restore 1E4 binding to mouse RANTES. Briefly, mouse RANTES, human RANTES as well as three mutant forms of mouse RANTES and control supernatants were captured in Streptawell plates (Roche) for 30 minutes at room temperature. After washing, antibody 1E4 was added at a concentration of 1 μg/ml in 1% BSA-PBS and incubated for 1 hour at room temperature. The plate was washed and incubated with a goat anti-human IgG Fcγ-specific antibody coupled to horse radish peroxidase (Jackson). After washing the signal was revealed with TMB (Roche) and stopped with $H_2SO_4$. The plates were read at 450 nm. As shown in FIG. 7, the [S16A/L17R/A18P]mutant restores binding of 1E4 to mouse RANTES indicating that A16, R17 and P18 are critical for the 1E4 epitope integrity on human RANTES.

Example 15

Affinity and Binding Kinetics of 1E4

The affinity and binding kinetics of 1E4 on human RANTES and cynomolgus RANTES were characterized on a Biacore 2000 instrument (Biacore AB, Uppsala, Sweden). 433 RU (response unit) of a donkey anti-human IgG polyclonal antibody were immobilized by EDC/NHS chemistry on a C1 Biacore chip. This surface was used to capture antibody 1E4. The surface was regenerated after each cycle by injection of 10 mM glycine pH=2 at 30 μL/min, for 60 s followed by 1 min. of stabilization time in HBS-EP buffer.

Binding was measured by passing either huRANTES (Peprotech, Rocky Hill N.J.) or a NusA-fusion proteins of human RANTES (NusA-huRANTES) and *Cynomolgus* RANTES (NusA-cynoRANTES) at various concentrations. All proteins were diluted in the running buffer HBS-EP buffer (Biacore AB, Uppsala, Sweden). Injection was performed at 75 μl/min for 3 min. followed by 15 min. of dissociation time and the temperature was set at 25° C. The data was fitted according to 1:1 Langmuir model and the $K_{on}$, $K_{off}$ and $K_D$ values determined. Very similar values were obtained using huRANTES or the NusA-huRANTES fusion, but better response signals were obtained with the fusion protein due to its larger size that induces a better response on the Biacore. The affinity of antibody 1E4 for huRANTES and cynoRANTES are 0.45 nM and 2.24 nM, respectively. The Affinities and kinetic constants of both antibodies are summarized in Table 10.

TABLE 10

Kinetic and affinity constants of antibody 1E4 for human and cynomolgus RANTES measured by Biacore.

| | huRANTES | NusA-huRANTES | NusA-cynoRANTES |
|---|---|---|---|
| Ka (1/Ms) | $5.36 \times 10^{6}$ | $1.87 \times 10^{6}$ | $5.46 \times 10^{6}$ |
| Kd (1/s) | $2.44 \times 10^{-3}$ | $8.35 \times 10^{-4}$ | $1.22 \times 10^{-3}$ |
| KD (M) | $4.55 \times 10^{-10}$ | $4.47 \times 10^{-10}$ | $2.24 \times 10^{-9}$ |

Example 16

Animal Model of Ischemia

Materials and Methods

Animals: Eight to 12 week old C57BL/6 mice are used for the experiments. All animal studies were approved by the local ethical Committee.

Antibodies and in vivo treatment: C57BL/6 mice were injected either in the peritoneal cavity (i.p.) or intraveneously (i.v.). For the ischemia followed by reperfusion model, monoclonal antibodies (mAb) were injected 5 minutes before the end of the occlusion period. For the permanent ligation model, mAbs were injected 5 minutes after the chronic ligature was put in place. The mAbs included: (1) the rat anti-mouse RANTES (mRANTES), mAb478 and (2) the rat anti-mouse isotype mAb control, mAb64. Hybridomas that produced mAb478 or mAb64 were obtained from R&D or the American Tissue Culture Collection, respectively, and all mAb were produced, purified and stored in-house.

For the i.p. treatment, 1 mg/mouse of the IgG control or anti-mRANTES mAbs was administered. For the i.v. treatment, either 0.1, 0.3, 0.5 or 1 mg/mouse of the anti-mRANTES mAb or 1 mg/mouse of the IgG control (i.e. highest dose of anti-mRANTES) was administered.

In Vivo Ischemia-Reperfusion or Ligation Permanent Model

Surgery: Mice were initially anesthetized with 4% isofluorane then intubated. Mechanical ventilation was performed with a tidal volume of 300 μL at 120 breaths using a rodent respirator (model 683; Harvard Apparatus). Anesthesia was maintained with 2% isofluorane delivered 100% through the ventilator. A thoracotomy was performed in the left fourth intercostal space, and the pericardial sac was then removed. An 8-0 Prolene suture was passed under the left coronary artery at the inferior edge of the left atrium and tied with a slipknot to produce occlusion.

For the reperfusion model, a small piece of polyethylene tubing was used to secure the ligature without damaging the artery and after 30 minutes of ischemia, the left anterior descending (LAD) coronary artery occlusion was released and reperfusion permitted to occur.

For the permanent legation model, the LAD coronary artery was irreversibly occluded by using a double knot 8-0 Prolene suture. The chest was then closed and air was evacuated from the chest cavity. The endotracheal tube was then removed and normal respiration restored.

After 24 hours of reperfusion or after 24 hours of permanent occlusion, animals were euthanized to determine infarct size.

Evaluation of Risk Zone and Infarct Size: At the end of the reperfusion period, mice were re-anesthetized with 0.3 mL ketamine-xylazine and the LAD coronary artery was re-ligated. 3% Evans Blue dye (Sigma) was injected i.v. (retro-orbital administration) to delineate the in vivo risk zone (R). The heart was rapidly excised and rinsed in saline. After removal of the right ventricle and connective tissues, the heart was frozen and then sectioned into 3-mm transverse sections from apex to base (5 slices/heart). Following thawing, the sections were incubated at 37° C. with 1% triphenyltetrazolium chloride in phosphate buffer (pH7.4) for 15 min, fixed in 10% formaldehyde solution and, after 24 hours, photographed with a digital camera to distinguish areas of stained viable versus unstained necrotic tissue. Left ventricular infarct zone (I) was determined using a computerized planimetric technique (MetaMorph6 software, Zeiss) and expressed as a percentage of either the area at risk (AAR) or ventricular area (V).

Example 17

Effect of Inhibiting RANTES in Ischemia Reperfusion Models

Model 1: Ischemia Reperfusion

A diagram illustrating the protocol of the murine ischemia reperfusion model is shown in FIG. 8. In this protocol, B6 mice are divided into three groups and administered a vehicle control (PBS), an isotype control (mAb 64 described in Example 10) or a rat anti-mRANTES monoclonal antibody according to the following schedule:

Group 1: PBS administered i.p. or i.v. 5 minutes prior to reperfusion;
Group 2: rat IgG2a (mAb 64; isotype control) administered i.p. (1 mg/mouse) or i.v. (1.0 mg/mouse) 5 minutes prior to reperfusion;
Group 3: rat anti-mouse RANTES (mAb 478) administered i.p. (1 mg/mouse) or i.v. (0.1, 0.3, 0.5, 1.0 mg/mouse) 5 minutes prior to reperfusion;

All animals were killed 24 hours post-reperfusion. Each group of mice was evaluated by assessing the following parameters:
weight of mice;
AAR/V=area at risk divided by the total area of heart (ischemic zone);
I/AAR=infarcted area divided by the area at risk; and
I/V=infarcted area divided by the total area of the ventricles.

Both I/AAR and I/V provide data on extent of infarcted tissue.

Figure 9:
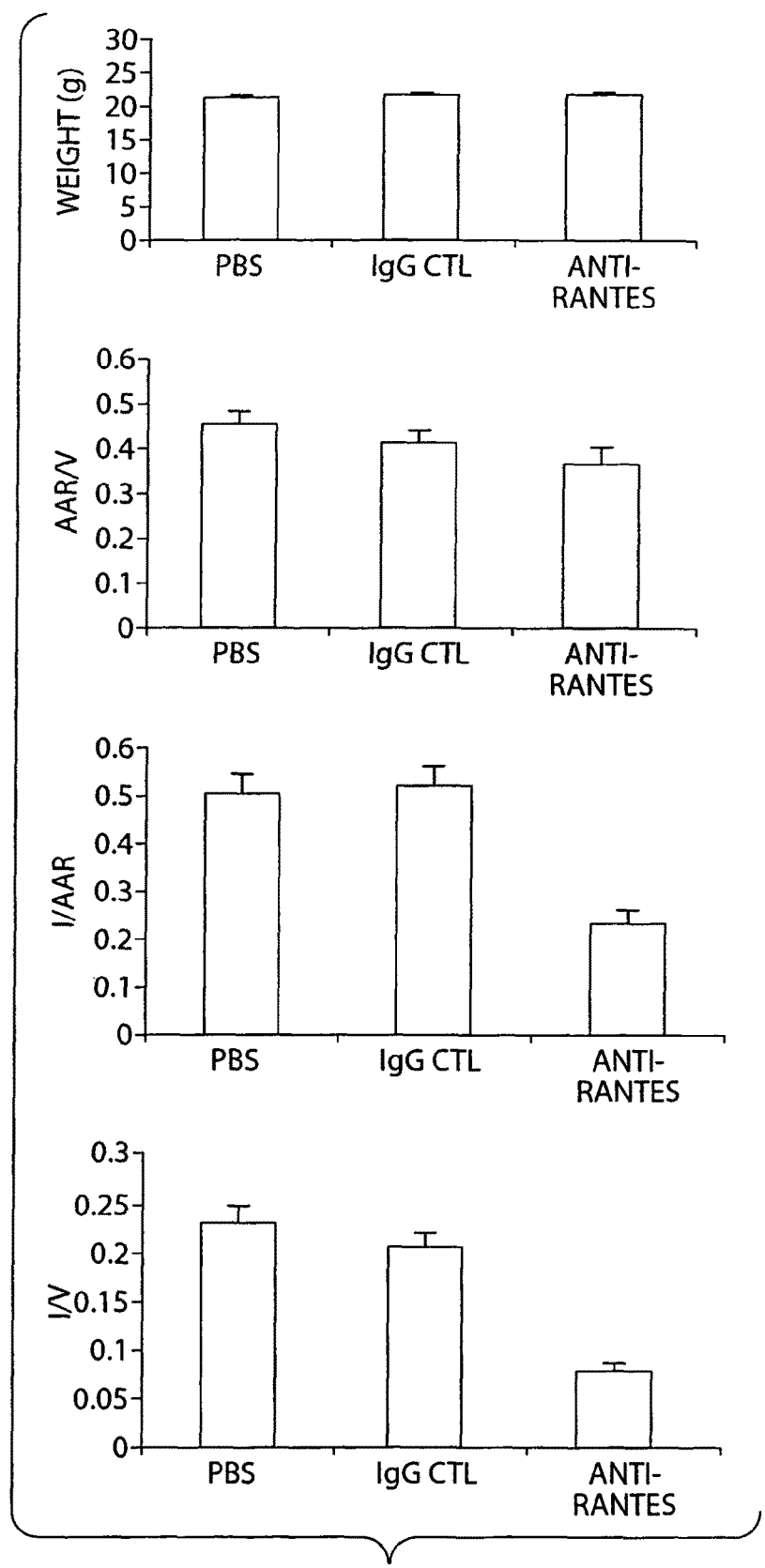
FIG. 9 is a series of graphs depicting that anti-RANTES treatment decreased infarct size in a murine model of ischemia reperfusion. The data represents 20 mice per group.

As shown in FIG. 9, treatment with the anti-RANTES monoclonal antibody decreased infarct size in the murine model of ischemia reperfusion provided herein. Injecting mAb 478 (1 mg/mouse i.p.) five minutes prior to reperfusion significantly decreased the infarct size as compared to isotype control or PBS treated mice. Data represents 20 mice per group.

Figure 10:
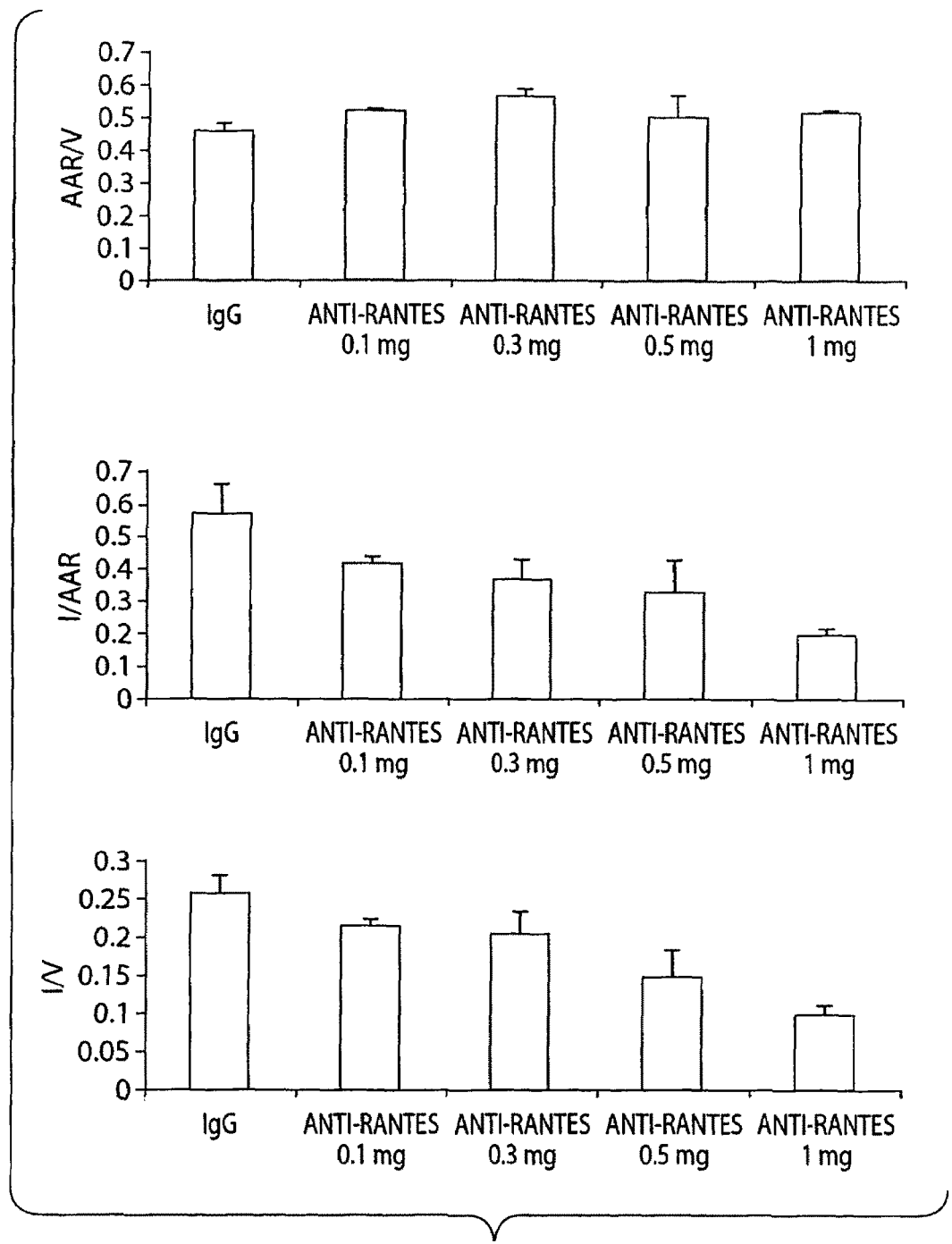
FIG. 10 is a series of graphs depicting that anti-RANTES treatment decreased infarct size in a murine model of ischemia reperfusion in a dose-dependent manner. Data represents 3 mice per group.

FIG. 10 demonstrates that treatment with the anti-RANTES monoclonal antibody decreased infarct size in the murine model of ischemia reperfusion in a dose-dependent manner. Injecting mAb 478 i.v. (at doses of 0.1, 0.3, 0.5, 1.0 mg/mouse) five minutes prior to reperfusion significantly decreased the infarct size at higher doses as compared to isotype control (1 mg/mouse). Data represents 3 mice per group.

Model 2: Permanent Occlusion

Figure 11:
FIG. 11 is an illustration depicting the protocol of a murine ischemia model provided herein.

A diagram illustrating the protocol of the murine permanent occlusion model is shown in FIG. 11. In this protocol, B6 mice are divided into three groups and administered a vehicle control (PBS), an isotype control (mAb 64 described in Example 10) or a rat anti-mRANTES monoclonal antibody according to the following schedule:
Group 1: PBS administered i.p. or i.v.;
Group 2: rat IgG2a (mAb 64; isotype control) administered i.p. (1 mg/mouse) or i.v. (1.0 mg/mouse);
Group 3: rat anti-mouse RANTES (mAb 478) administered i.p. (1 mg/mouse) or i.v. (0.1, 0.3, 0.5, 1.0 mg/mouse).

Each group of mice was evaluated by assessing the following parameters:
weight of mice;
AAR/V=area at risk divided by the total area of heart (ischemic zone);
I/AAR=infarcted area divided by the area at risk; and
I/V=infarcted area divided by the total area of the ventricles.

All animals were killed at 24 hrs post occlusion.

Figure 12:
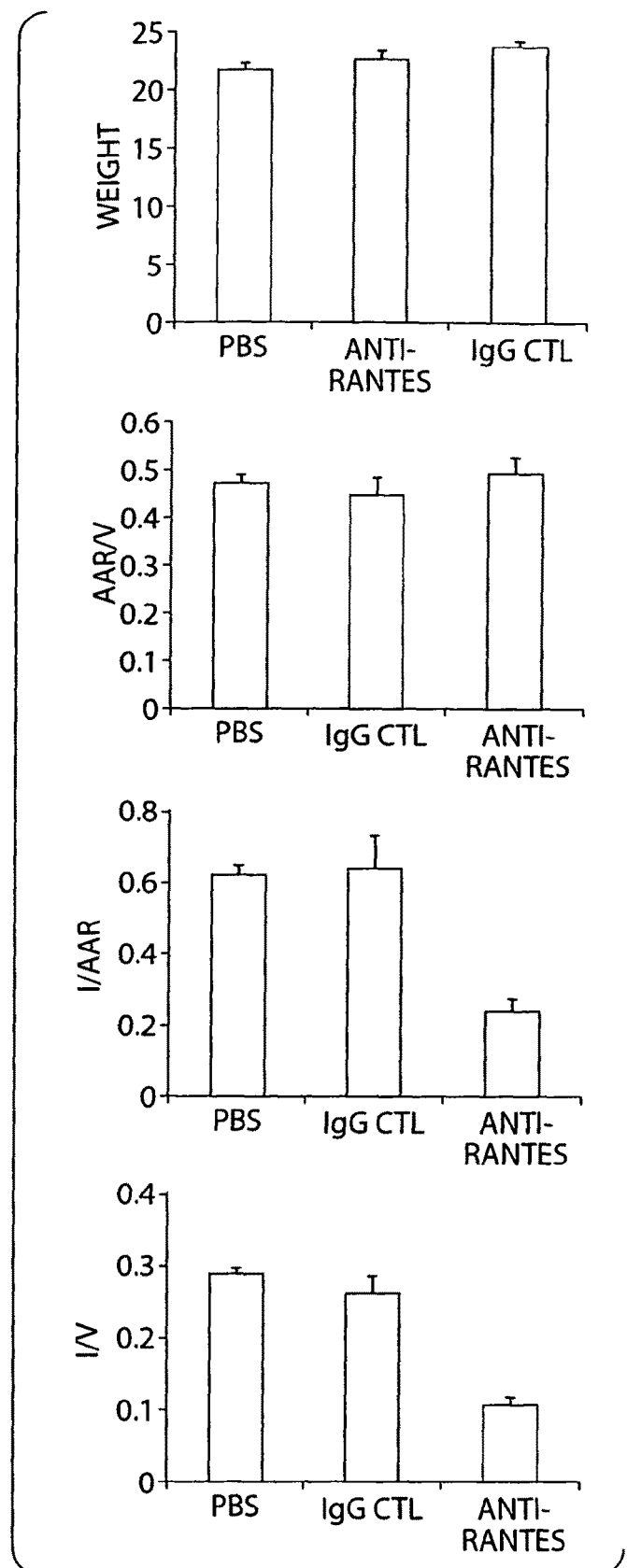
FIG. 12 is a series of graphs depicting that anti-RANTES treatment decreased infarct size in a murine model of ischemia. The data represents 10 mice per group.

As shown in FIG. 12, treatment with the anti-RANTES monoclonal antibody decreased infarct size in the murine model of ischemia provided herein. Injecting mAb 478 (1 mg/mouse i.p.) significantly decreased the infarct size as compared to isotype control or PBS treated mice. Data represents 10 mice per group.

Figure 13:
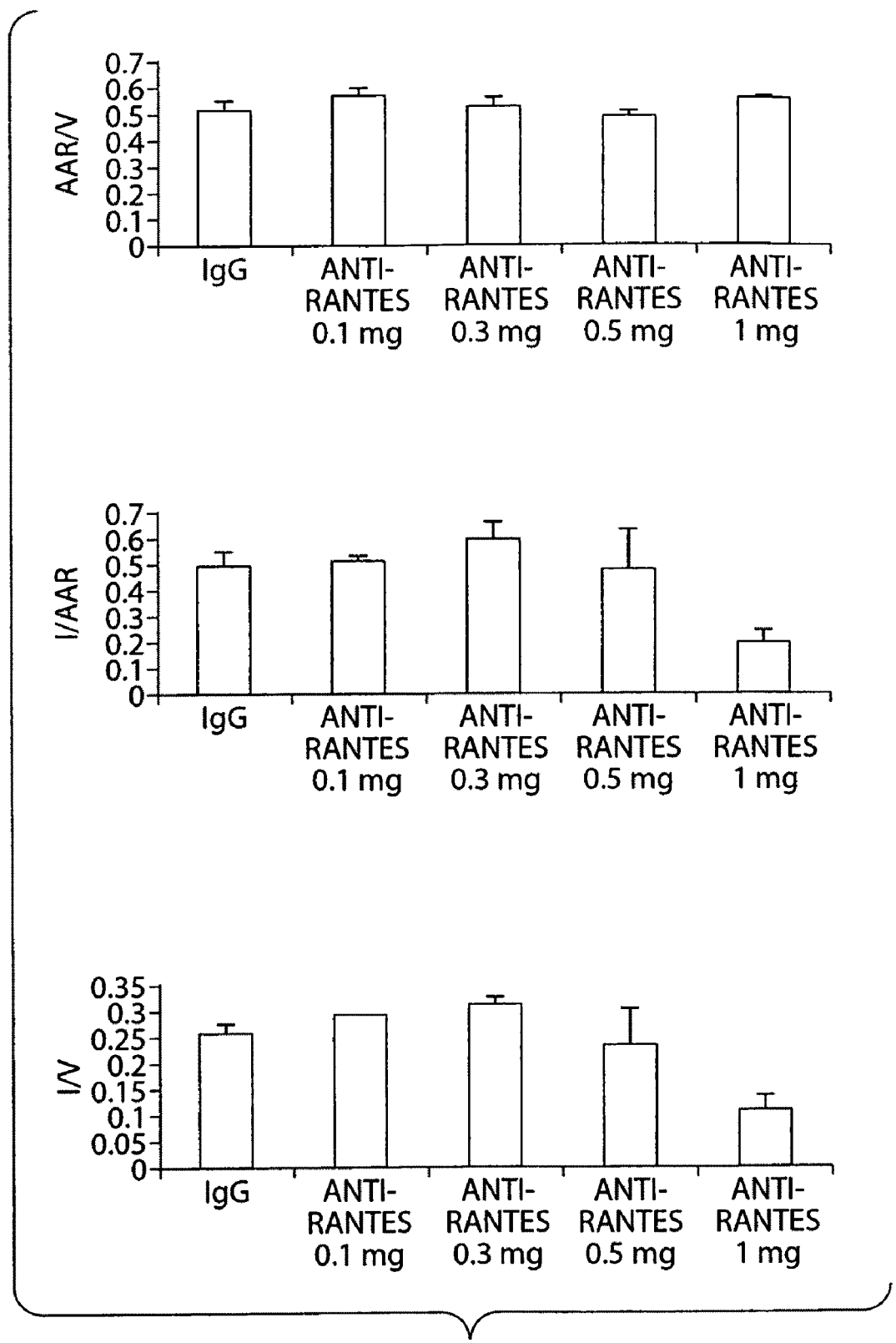
FIG. 13 is a series of graphs depicting that anti-RANTES treatment decreased infarct size in a murine model of ischemia in a dose-dependent manner. Data represents 3 mice per group.

FIG. 13 demonstrates that treatment with the anti-RANTES monoclonal antibody decreased infarct size in the murine model of ischemia in a dose-dependent manner. Injecting mAb 478 i.v. (at doses of 0.1, 0.3, 0.5, 1.0 mg/mouse) significantly decreased the infarct size at higher doses as compared to isotype control (1 mg/mouse). Data represents 3 mice per group.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated fully human monoclonal antibody or fragment thereof that binds human Regulated upon Activation, Normal T-cell Expressed, and Secreted (RANTES), wherein said antibody comprises:
   (a) a $V_H$ CDR1 region comprising the amino acid sequence of SEQ ID NO: 8;
   (b) a $V_H$ CDR2 region comprising the amino acid sequence of SEQ ID NO: 9;
   (c) a $V_H$ CDR3 region comprising the amino acid sequence of SEQ ID NO: 20;
   (d) a $V_L$ CDR1 region comprising the amino acid sequence of SEQ ID NO: 14;
   (e) a $V_L$ CDR2 region comprising the amino acid sequence of SEQ ID NO: 15; and
   (f) a $V_L$ CDR3 region comprising the amino acid sequence of SEQ ID NO: 16,
wherein said antibody binds RANTES.

2. The antibody of claim 1, wherein said antibody is an IgG isotype.

3. The antibody of claim 1, wherein said antibody is an IgG1 isotype.

4. The antibody of claim 1, wherein said antibody further comprises a heavy chain variable sequence comprising the amino acid sequence of SEQ ID NO: 18 and a light chain variable sequence comprising the amino acid sequence of SEQ ID NO: 4.

5. A pharmaceutical composition comprising the antibody of claim 1 and a carrier.

6. An isolated fully human monoclonal antibody comprising a heavy chain variable sequence comprising the amino acid sequence of SEQ ID NO: 18 and a light chain variable sequence comprising the amino acid sequence of SEQ ID NO: 4, wherein said antibody binds RANTES.

7. The antibody of claim 6, wherein said antibody is an IgG isotype.

8. The antibody of claim 6, wherein said antibody further comprises a heavy chain sequence comprising the amino acid sequence of SEQ ID NO:238 and a light chain sequence comprising the amino acid sequence of SEQ ID NO:254.

9. An isolated antibody that binds human Regulated upon Activation, Normal T-cell Expressed, and Secreted (RANTES) when human RANTES is bound to a glycosaminoglycan (GAG), wherein said antibody comprises:
   (a) a $V_H$ CDR1 region comprising the amino acid sequence of SEQ ID NO: 8;
   (b) a $V_H$ CDR2 region comprising the amino acid sequence of SEQ ID NO: 9;
   (c) a $V_H$ CDR3 region comprising the amino acid sequence of SEQ ID NO: 20;
   (d) a $V_L$ CDR1 region comprising the amino acid sequence of SEQ ID NO: 14;
   (e) a $V_L$ CDR2 region comprising the amino acid sequence of SEQ ID NO: 15; and
   (f) a $V_L$ CDR3 region comprising the amino acid sequence of SEQ ID NO: 16.

10. The antibody of claim 9, wherein said antibody is a monoclonal antibody or an antigen-binding fragment thereof.

11. The antibody of claim 9, wherein said antibody is a fully human monoclonal antibody or an antigen-binding fragment thereof.

12. The antibody of claim 9, wherein said antibody is an IgG isotype.

13. The antibody of claim 9, wherein said antibody is an IgG1 isotype.

* * * * *

SEQUENCE LISTING

```
<160> NUMBER OF SEQ ID NOS: 255

<210> SEQ ID NO 1
<211> LENGTH: 357
<212> TYPE: DNA
<213> ORGANISM: Artificial Sequence
<220> FEATURE:
<223> OTHER INFORMATION: chemically synthesized

<400> SEQUENCE: 1
caggtgcagc tggtgcagtc tggggctgag gtgaagaagc ctggggcctc agtgaaggtt    60
tcctgcaagg tttccggata caccctcact gagttcgcca tgcactgggt gcgacaggct   120
cctggaaaag ggcttgagtg gatgggaggt tttgttcctg aagatggtga gacaatctac   180
gcgcagaagt tccagggcag agtcaccatg accgaggaca catctacaga cacagcctac   240
atggagctga gcagcctgag atctgaggac acggccgtgt attactgtgc aacagatccc   300
ctgtatactc cgggtcttga gccttggggg caggggacca cggtcaccgt ctcgagt      357

<210> SEQ ID NO 2
<211> LENGTH: 119
<212> TYPE: PRT
```

```
<213> ORGANISM: Artificial Sequence
<220> FEATURE:
<223> OTHER INFORMATION: chemically synthesized

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Phe
            20                  25                  30

Ala Met His Trp Val Arg Gln Ala Pro Gly Lys Gly Leu Glu Trp Met
        35                  40                  45

Gly Gly Phe Val Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Pro Leu Tyr Thr Pro Gly Leu Glu Pro Trp Gly Gln Gly
            100                 105                 110

Thr Thr Val Thr Val Ser Ser
        115

<210> SEQ ID NO 3
<211> LENGTH: 324
<212> TYPE: DNA
<213> ORGANISM: Artificial Sequence
<220> FEATURE:
<223> OTHER INFORMATION: chemically synthesized

<400> SEQUENCE: 3
tcctatgtgc tgactcagcc accctcggtg tcagtggccc caggacagac ggccaggatt    60
acctgtgggg gaaacaacat tgaaagtaaa agtgtgcact ggtaccagca gaagccaggc   120
caggcccctg tgctggtggt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtaata ctgatcattg ggtgttcggc   300
ggagggacca agctcaccgt ccta                                          324

<210> SEQ ID NO 4
<211> LENGTH: 108
<212> TYPE: PRT
<213> ORGANISM: Artificial Sequence
<220> FEATURE:
<223> OTHER INFORMATION: chemically synthesized

<400> SEQUENCE: 4

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Glu Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Asn Thr Asp His
                85                  90                  95
```

```
Trp Val Phe Gly Gly Gly Thr Lys Leu Thr Val Leu
            100                 105
```

<210> SEQ ID NO 5
<211> LENGTH: 15
<212> TYPE: DNA
<213> ORGANISM: Artificial Sequence
<220> FEATURE:
<223> OTHER INFORMATION: chemically synthesized

<400> SEQUENCE: 5
gagttcgcca tgcac    15

<210> SEQ ID NO 6
<211> LENGTH: 51
<212> TYPE: DNA
<213> ORGANISM: Artificial Sequence
<220> FEATURE:
<223> OTHER INFORMATION: chemically synthesized

<400> SEQUENCE: 6
ggttttgttc ctgaagatgg tgagacaatc tacgcgcaga agttccaggg c    51

<210> SEQ ID NO 7
<211> LENGTH: 30
<212> TYPE: DNA
<213> ORGANISM: Artificial Sequence
<220> FEATURE:
<223> OTHER INFORMATION: chemically synthesized

<400> SEQUENCE: 7
gatcccctgt atactccggg tcttgagcct    30

<210> SEQ ID NO 8
<211> LENGTH: 5
<212> TYPE: PRT
<213> ORGANISM: Artificial Sequence
<220> FEATURE:
<223> OTHER INFORMATION: chemically synthesized

<400> SEQUENCE: 8

```
Glu Phe Ala Met His
1               5
```

<210> SEQ ID NO 9
<211> LENGTH: 17
<212> TYPE: PRT
<213> ORGANISM: Artificial Sequence
<220> FEATURE:
<223> OTHER INFORMATION: chemically synthesized

<400> SEQUENCE: 9

```
Gly Phe Val Pro Glu Asp Gly Glu Thr Ile Tyr Ala Gln Lys Phe Gln
1               5                   10                  15

Gly
```

<210> SEQ ID NO 10
<211> LENGTH: 10
<212> TYPE: PRT
<213> ORGANISM: Artificial Sequence
<220> FEATURE:
<223> OTHER INFORMATION: chemically synthesized

<400> SEQUENCE: 10

```
Asp Pro Leu Tyr Thr Pro Gly Leu Glu Pro
1               5                   10
```

<210> SEQ ID NO 11
<211> LENGTH: 33
<212> TYPE: DNA
<213> ORGANISM: Artificial Sequence
<220> FEATURE:
<223> OTHER INFORMATION: chemically synthesized

<400> SEQUENCE: 11 ggggaaaca acattgaaag taaaagtgtg cac                          33

<210> SEQ ID NO 12
<211> LENGTH: 21
<212> TYPE: DNA
<213> ORGANISM: Artificial Sequence
<220> FEATURE:
<223> OTHER INFORMATION: chemically synthesized

<400> SEQUENCE: 12
gatgatagcg accggccctc a                                      21

<210> SEQ ID NO 13
<211> LENGTH: 33
<212> TYPE: DNA
<213> ORGANISM: Artificial Sequence
<220> FEATURE:
<223> OTHER INFORMATION: chemically synthesized

<400> SEQUENCE: 13
caggtgtggg atagtaatac tgatcattgg gtg                         33

<210> SEQ ID NO 14
<211> LENGTH: 11
<212> TYPE: PRT
<213> ORGANISM: Artificial Sequence
<220> FEATURE:
<223> OTHER INFORMATION: chemically synthesized

<400> SEQUENCE: 14

Gly Gly Asn Asn Ile Glu Ser Lys Ser Val His
1               5                   10

<210> SEQ ID NO 15
<211> LENGTH: 7
<212> TYPE: PRT
<213> ORGANISM: Artificial Sequence
<220> FEATURE:
<223> OTHER INFORMATION: chemically synthesized

<400> SEQUENCE: 15

Asp Asp Ser Asp Arg Pro Ser
1               5

<210> SEQ ID NO 16
<211> LENGTH: 11
<212> TYPE: PRT
<213> ORGANISM: Artificial Sequence
<220> FEATURE:
<223> OTHER INFORMATION: chemically synthesized

<400> SEQUENCE: 16

Gln Val Trp Asp Ser Asn Thr Asp His Trp Val
1               5                   10

<210> SEQ ID NO 17
<211> LENGTH: 357
<212> TYPE: DNA
<213> ORGANISM: Artificial Sequence -continued

```
<220> FEATURE:
<223> OTHER INFORMATION: chemically synthesized

<400> SEQUENCE: 17
caggtgcagc tggtgcagtc tggggctgag gtgaagaagc ctggggcctc agtgaaggtt      60
tcctgcaagg tttccggata caccctcact gagttcgcca tgcactgggt gcgacaggct     120
cctggaaaag gcttgagtg gatgggaggt tttgttcctg aagatggtga gacaatctac      180
gcgcagaagt tccagggcag agtcaccatg accgaggaca catctacaga cacagcctac     240
atggagctga gcagcctgag atctgaggac acggccgtgt attactgtgc aacagatccc     300
ctgtatgagg gttcgttttc tgtttggggg caggggacca cggtcaccgt ctcgagt        357

<210> SEQ ID NO 18
<211> LENGTH: 119
<212> TYPE: PRT
<213> ORGANISM: Artificial Sequence
<220> FEATURE:
<223> OTHER INFORMATION: chemically synthesized

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Phe
            20                  25                  30

Ala Met His Trp Val Arg Gln Ala Pro Gly Lys Gly Leu Glu Trp Met
        35                  40                  45

Gly Gly Phe Val Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Pro Leu Tyr Glu Gly Ser Phe Ser Val Trp Gly Gln Gly
            100                 105                 110

Thr Thr Val Thr Val Ser Ser
        115

<210> SEQ ID NO 19
<211> LENGTH: 30
<212> TYPE: DNA
<213> ORGANISM: Artificial Sequence
<220> FEATURE:
<223> OTHER INFORMATION: chemically synthesized

<400> SEQUENCE: 19
gatcccctgt atgagggtcc gttttctgtt                                       30

<210> SEQ ID NO 20
<211> LENGTH: 10
<212> TYPE: PRT
<213> ORGANISM: Artificial Sequence
<220> FEATURE:
<223> OTHER INFORMATION: chemically synthesized

<400> SEQUENCE: 20

Asp Pro Leu Tyr Glu Gly Ser Phe Ser Val
1               5                   10

<210> SEQ ID NO 21
<211> LENGTH: 366
<212> TYPE: DNA
```

<213> ORGANISM: Artificial Sequence
<220> FEATURE:
<223> OTHER INFORMATION: chemically synthesized

<400> SEQUENCE: 21

```
caggtgcagc tggtggagtc tgggggaggc gtggtccagc ctggagggtc cctgagactc      60
tcctgtgcag cctctggatt caccttcagt agctatgcta tgcactgggt ccgccaggct     120
ccaggcaagg gctagagtg gtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagagaaact     300 ttccccccact actactacta ctacatggac gtctggggcc ggggcaccct ggtcaccgtc     360
tcgagt                                                                 366
```

<210> SEQ ID NO 22
<211> LENGTH: 122
<212> TYPE: PRT
<213> ORGANISM: Artificial Sequence
<220> FEATURE:
<223> OTHER INFORMATION: chemically synthesized

<400> SEQUENCE: 22

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Phe Pro His Tyr Tyr Tyr Tyr Met Asp Val Trp
            100                 105                 110

Gly Arg Gly Thr Leu Val Thr Val Ser Ser
        115                 120
```

<210> SEQ ID NO 23
<211> LENGTH: 324
<212> TYPE: DNA
<213> ORGANISM: Artificial Sequence
<220> FEATURE:
<223> OTHER INFORMATION: chemically synthesized

<400> SEQUENCE: 23

```
tcctatgtgc tgactcagcc cccctcggtg tcagtggccc cagggcagac ggcccgcatt      60
acctgtgagg gagacgacac tgacattggt actgtcaact ggtaccagca gaaaccaggc     120
caggcccctg tgttggtcat tagtgaggat ggctaccggc cctcagggat ccctgaacga     180
ttctctggct ccaactctgg gaacacggcc acccttacca tctccagggt cgaggccggg     240
gatgaggccg actattactg tcagttctgg gatgttgaca gtgatcatcc ggttttcggc     300
ggagggaccc agctcaccgt ccta                                             324
```

<210> SEQ ID NO 24
<211> LENGTH: 108
<212> TYPE: PRT

```
<213> ORGANISM: Artificial Sequence
<220> FEATURE:
<223> OTHER INFORMATION: chemically synthesized

<400> SEQUENCE: 24

Ser Tyr Val Leu Thr Gln Pro Pro Ser Val Ser Val Ala Pro Gly Gln
1               5                   10                  15

Thr Ala Arg Ile Thr Cys Glu Gly Asp Asp Thr Asp Ile Gly Thr Val
            20                  25                  30

Asn Trp Tyr Gln Gln Lys Pro Gly Gln Ala Pro Val Leu Val Ile Ser
        35                  40                  45

Glu Asp Gly Tyr Arg Pro Ser Gly Ile Pro Glu Arg Phe Ser Gly Ser
50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Phe Trp Asp Val Asp Ser Asp His
                85                  90                  95

Pro Val Phe Gly Gly Gly Thr Gln Leu Thr Val Leu
            100                 105

<210> SEQ ID NO 25
<211> LENGTH: 15
<212> TYPE: DNA
<213> ORGANISM: Artificial Sequence
<220> FEATURE:
<223> OTHER INFORMATION: chemically synthesized

<400> SEQUENCE: 25
agctatgcta tgcac                                                      15

<210> SEQ ID NO 26
<211> LENGTH: 51
<212> TYPE: DNA
<213> ORGANISM: Artificial Sequence
<220> FEATURE:
<223> OTHER INFORMATION: chemically synthesized

<400> SEQUENCE: 26
gttatatcat atgatggaag taataaatac tacgcagact ccgtgaaggg c              51

<210> SEQ ID NO 27
<211> LENGTH: 39
<212> TYPE: DNA
<213> ORGANISM: Artificial Sequence
<220> FEATURE:
<223> OTHER INFORMATION: chemically synthesized

<400> SEQUENCE: 27
gaaactttcc cccactacta ctactactac atggacgtc                            39

<210> SEQ ID NO 28
<211> LENGTH: 5
<212> TYPE: PRT
<213> ORGANISM: Artificial Sequence
<220> FEATURE:
<223> OTHER INFORMATION: chemically synthesized

<400> SEQUENCE: 28

Ser Tyr Ala Met His
1               5

<210> SEQ ID NO 29
<211> LENGTH: 17
<212> TYPE: PRT
```

<213> ORGANISM: Artificial Sequence
<220> FEATURE:
<223> OTHER INFORMATION: chemically synthesized

<400> SEQUENCE: 29

Val Ile Ser Tyr Asp Gly Ser Asn Lys Tyr Tyr Ala Asp Ser Val Lys
1               5                   10                  15
Gly

<210> SEQ ID NO 30
<211> LENGTH: 13
<212> TYPE: PRT
<213> ORGANISM: Artificial Sequence
<220> FEATURE:
<223> OTHER INFORMATION: chemically synthesized

<400> SEQUENCE: 30

Glu Thr Phe Pro His Tyr Tyr Tyr Tyr Met Asp Val
1               5                   10

<210> SEQ ID NO 31
<211> LENGTH: 33
<212> TYPE: DNA
<213> ORGANISM: Artificial Sequence
<220> FEATURE:
<223> OTHER INFORMATION: chemically synthesized

<400> SEQUENCE: 31
gagggagacg acactgacat tggtactgtc aac                          33

<210> SEQ ID NO 32
<211> LENGTH: 21
<212> TYPE: DNA
<213> ORGANISM: Artificial Sequence
<220> FEATURE:
<223> OTHER INFORMATION: chemically synthesized

<400> SEQUENCE: 32
gaggatggct accggccctc a                                       21

<210> SEQ ID NO 33
<211> LENGTH: 33
<212> TYPE: DNA
<213> ORGANISM: Artificial Sequence
<220> FEATURE:
<223> OTHER INFORMATION: chemically synthesized

<400> SEQUENCE: 33
cagttctggg atgttgacag tgatcatccg gtt                          33

<210> SEQ ID NO 34
<211> LENGTH: 11
<212> TYPE: PRT
<213> ORGANISM: Artificial Sequence
<220> FEATURE:
<223> OTHER INFORMATION: chemically synthesized

<400> SEQUENCE: 34

Glu Gly Asp Asp Thr Asp Ile Gly Thr Val Asn
1               5                   10

<210> SEQ ID NO 35
<211> LENGTH: 7
<212> TYPE: PRT
<213> ORGANISM: Artificial Sequence
<220> FEATURE:
<223> OTHER INFORMATION: chemically synthesized

<400> SEQUENCE: 35

Glu Asp Gly Tyr Arg Pro Ser
1               5

<210> SEQ ID NO 36
<211> LENGTH: 11
<212> TYPE: PRT
<213> ORGANISM: Artificial Sequence
<220> FEATURE:
<223> OTHER INFORMATION: chemically synthesized

<400> SEQUENCE: 36

Gln Phe Trp Asp Val Asp Ser Asp His Pro Val
1               5                   10

<210> SEQ ID NO 37
<211> LENGTH: 357
<212> TYPE: DNA
<213> ORGANISM: Artificial Sequence
<220> FEATURE:
<223> OTHER INFORMATION: chemically synthesized

<400> SEQUENCE: 37
caggtgcagc tggtgcagtc tggggctgag gtgaagaagc ctggggcctc agtgaaggtt      60
tcctgcaagg tttccggata caccctcaat gacttcgcca tgcactgggt gcgacaggct     120
cctggaaaag ggcttgagtg gatgggaggt tatgttcctg aagatggtga cacaatctac     180
gcgcagaagt tccagggcag agtcaccatg accgaggaca catctacaga cacagcctac     240
atggagctga gcagcctgag atctgaggac acggccgtgt attactgtgc aacagatccc     300
ctgtatccgc ctgggctgtc tccttggggg caggggacca cggtcaccgt ctcgagt       357

<210> SEQ ID NO 38
<211> LENGTH: 119
<212> TYPE: PRT
<213> ORGANISM: Artificial Sequence
<220> FEATURE:
<223> OTHER INFORMATION: chemically synthesized

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Asn Asp Phe
                20                  25                  30

Ala Met His Trp Val Arg Gln Ala Pro Gly Lys Gly Leu Glu Trp Met
            35                  40                  45

Gly Gly Tyr Val Pro Glu Asp Gly Asp Thr Ile Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Pro Leu Tyr Pro Pro Gly Leu Ser Pro Trp Gly Gln Gly
            100                 105                 110

Thr Thr Val Thr Val Ser Ser
        115

<210> SEQ ID NO 39
<211> LENGTH: 324
<212> TYPE: DNA
<213> ORGANISM: Artificial Sequence
<220> FEATURE:
<223> OTHER INFORMATION: chemically synthesized

<400> SEQUENCE: 39

```
tcctatgtgc tgactcagcc accctcggtg tcagtggccc caggacagac ggccaggatt    60
acctgtgggg gaaacaacat tgaaagtaaa agtgtgcact ggtaccagca gaagccaggc   120
caggcccctg tgctggtggt ctatgatgat agcgaccggc cctcagggat ccctgagcga   180
ttctctggct ccaactctgg gaacacggcc accctgacca tcagcagggt cgaagccggg   240
gatgaggccg actattactg tcaggtgtgg gatagtaata ctgatcattg ggtgttcggc   300
ggagggacca aggtcaccgt ccta                                          324
```

<210> SEQ ID NO 40
<211> LENGTH: 108
<212> TYPE: PRT
<213> ORGANISM: Artificial Sequence
<220> FEATURE:
<223> OTHER INFORMATION: chemically synthesized

<400> SEQUENCE: 40

```
Ser Tyr Val Leu Thr Gln Pro Pro Ser Val Ser Val Ala Pro Gly Gln
1               5                   10                  15
Thr Ala Arg Ile Thr Cys Gly Gly Asn Asn Ile Glu Ser Lys Ser Val
            20                  25                  30
His Trp Tyr Gln Gln Lys Pro Gly Gln Ala Pro Val Leu Val Val Tyr
        35                  40                  45
Asp Asp Ser Asp Arg Pro Ser Gly Ile Pro Glu Arg Phe Ser Gly Ser
    50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Asn Thr Asp His
                85                  90                  95
Trp Val Phe Gly Gly Gly Thr Lys Val Thr Val Leu
            100                 105
```

<210> SEQ ID NO 41
<211> LENGTH: 15
<212> TYPE: DNA
<213> ORGANISM: Artificial Sequence
<220> FEATURE:
<223> OTHER INFORMATION: chemically synthesized

<400> SEQUENCE: 41

```
gacttcgcca tgcac                                                     15
```

<210> SEQ ID NO 42
<211> LENGTH: 51
<212> TYPE: DNA
<213> ORGANISM: Artificial Sequence
<220> FEATURE:
<223> OTHER INFORMATION: chemically synthesized

<400> SEQUENCE: 42

```
ggttatgttc ctgaagatgg tgacacaatc tacgcgcaga gttccaggg c              51
```

<210> SEQ ID NO 43
<211> LENGTH: 30
<212> TYPE: DNA
<213> ORGANISM: Artificial Sequence
<220> FEATURE:
<223> OTHER INFORMATION: chemically synthesized
```

```
<400> SEQUENCE: 43
gatcccctgt atccgcctgg gctgtctcct                                              30

<210> SEQ ID NO 44
<211> LENGTH: 5
<212> TYPE: PRT
<213> ORGANISM: Artificial Sequence
<220> FEATURE:
<223> OTHER INFORMATION: chemically synthesized

<400> SEQUENCE: 44

Asp Phe Ala Met His
1               5

<210> SEQ ID NO 45
<211> LENGTH: 17
<212> TYPE: PRT
<213> ORGANISM: Artificial Sequence
<220> FEATURE:
<223> OTHER INFORMATION: chemically synthesized

<400> SEQUENCE: 45

Gly Tyr Val Pro Glu Asp Gly Asp Thr Ile Tyr Ala Gln Lys Phe Gln
1               5                   10                  15

Gly

<210> SEQ ID NO 46
<211> LENGTH: 10
<212> TYPE: PRT
<213> ORGANISM: Artificial Sequence
<220> FEATURE:
<223> OTHER INFORMATION: chemically synthesized

<400> SEQUENCE: 46

Asp Pro Leu Tyr Pro Pro Gly Leu Ser Pro
1               5                   10

<210> SEQ ID NO 47
<211> LENGTH: 357
<212> TYPE: DNA
<213> ORGANISM: Artificial Sequence
<220> FEATURE:
<223> OTHER INFORMATION: chemically synthesized

<400> SEQUENCE: 47
caggtgcagc tggtgcagtc tggggctgag gtgaagaagc ctggggcctc agtgaaggtt            60
tcctgcaagg tttccggata caccctcaat gacttcgcca tgcactgggt gcgacaggct           120
cctggaaaag ggcttgagtg gatgggaggt tatgttcctg aagatggtga cacaatctac           180
gcgcagaagt tccagggcag agtcaccatg accgaggaca tctacagaca cagcctac             240 atggagctga gcagcctgag atctgaggac acggccgtgt attactgtgc aacagatccc           300
ctgtatacgc ctggtctgta tgtgtggggg caggggacca cggtcaccgt ctcgagt              357

<210> SEQ ID NO 48
<211> LENGTH: 119
<212> TYPE: PRT
<213> ORGANISM: Artificial Sequence
<220> FEATURE:
<223> OTHER INFORMATION: chemically synthesized

<400> SEQUENCE: 48

Gln Val Gln Leu Val Gln Ser Gly Ala Glu Val Lys Lys Pro Gly Ala
1               5                   10                  15
```

```
Ser Val Lys Val Ser Cys Lys Val Ser Gly Tyr Thr Leu Asn Asp Phe
            20                  25                  30

Ala Met His Trp Val Arg Gln Ala Pro Gly Lys Gly Leu Glu Trp Met
        35                  40                  45

Gly Gly Tyr Val Pro Glu Asp Gly Asp Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Pro Leu Tyr Thr Pro Gly Leu Tyr Val Trp Gly Gln Gly
                100                 105                 110

Thr Thr Val Thr Val Ser Ser
        115
```

<210> SEQ ID NO 49
<211> LENGTH: 30
<212> TYPE: DNA
<213> ORGANISM: Artificial Sequence
<220> FEATURE:
<223> OTHER INFORMATION: chemically synthesized

<400> SEQUENCE: 49
gatcccctgt atacgcctgg tctgtatgtg                                    30

<210> SEQ ID NO 50
<211> LENGTH: 10
<212> TYPE: PRT
<213> ORGANISM: Artificial Sequence
<220> FEATURE:
<223> OTHER INFORMATION: chemically synthesized

<400> SEQUENCE: 50

```
Asp Pro Leu Tyr Thr Pro Gly Leu Tyr Val
1               5                   10
```

<210> SEQ ID NO 51
<211> LENGTH: 357
<212> TYPE: DNA
<213> ORGANISM: Artificial Sequence
<220> FEATURE:
<223> OTHER INFORMATION: chemically synthesized

<400> SEQUENCE: 51
caggtgcagc tggtgcagtc tggggctgag gtgaagaagc ctggggcctc agtgaaggtt    60
tcctgcaagg tttccggata caccctcaat gacttcgcca tgcactgggt gcgacaggct   120
cctggaaaag gccttgagtg gatgggaggt tatgttcctg aagatggtga cacaatctac   180
gcgcagaagt tccagggcag agtcaccatg accgaggaca catctacaga cacagcctac   240
atggagctga gcagcctgag atctgaggac acggccgtgt attactgtgc aacagattat   300
ttgtatattc ctagcttatc ctactggggg caggggacca cggtcaccgt ctcgagt      357

<210> SEQ ID NO 52
<211> LENGTH: 119
<212> TYPE: PRT
<213> ORGANISM: Artificial Sequence
<220> FEATURE:
<223> OTHER INFORMATION: chemically synthesized

<400> SEQUENCE: 52

```
Gln Val Gln Leu Val Gln Ser Gly Ala Glu Val Lys Lys Pro Gly Ala
1               5                   10                  15
```

Ser Val Lys Val Ser Cys Lys Val Ser Gly Tyr Thr Leu Asn Asp Phe
            20                  25                  30

Ala Met His Trp Val Arg Gln Ala Pro Gly Lys Gly Leu Glu Trp Met
        35                  40                  45

Gly Gly Tyr Val Pro Glu Asp Gly Asp Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Tyr Leu Tyr Ile Pro Ser Leu Ser Tyr Trp Gly Gln Gly
            100                 105                 110

Thr Thr Val Thr Val Ser Ser
            115

<210> SEQ ID NO 53
<211> LENGTH: 30
<212> TYPE: DNA
<213> ORGANISM: Artificial Sequence
<220> FEATURE:
<223> OTHER INFORMATION: chemically synthesized

<400> SEQUENCE: 53
gattatttgt atattcctag cttatcctac                                    30

<210> SEQ ID NO 54
<211> LENGTH: 10
<212> TYPE: PRT
<213> ORGANISM: Artificial Sequence
<220> FEATURE:
<223> OTHER INFORMATION: chemically synthesized

<400> SEQUENCE: 54

Asp Tyr Leu Tyr Ile Pro Ser Leu Ser Tyr
1               5                   10

<210> SEQ ID NO 55
<211> LENGTH: 357
<212> TYPE: DNA
<213> ORGANISM: Artificial Sequence
<220> FEATURE:
<223> OTHER INFORMATION: chemically synthesized

<400> SEQUENCE: 55
caggtgcagc tggtgcagtc tggggctgag gtgaagaagc ctggggcctc agtgaaggtt      60
tcctgcaagg tttccggata caccctcaat gacttcgcca tgcactgggt gcgacaggct     120
cctggaaaag ggcttgagtg gatgggaggt tatgttcctg aagatggtga cacaatctac     180
gcgcagaagt tccagggcag agtcaccatg accgaggaca catctacaga cacagcctac     240
atggagctga gcagcctgag atctgaggac acggccgtgt attactgtgc aacagatccc     300
ctgtatcctc cggggctgca gccttggggg caggggacca cggtcaccgt ctcgagt        357

<210> SEQ ID NO 56
<211> LENGTH: 119
<212> TYPE: PRT
<213> ORGANISM: Artificial Sequence
<220> FEATURE:
<223> OTHER INFORMATION: chemically synthesized

<400> SEQUENCE: 56

Gln Val Gln Leu Val Gln Ser Gly Ala Glu Val Lys Lys Pro Gly Ala

```
                1               5                   10                  15
            Ser Val Lys Val Ser Cys Lys Val Ser Gly Tyr Thr Leu Asn Asp Phe
                            20                  25                  30

Ala Met His Trp Val Arg Gln Ala Pro Gly Lys Gly Leu Glu Trp Met
                        35                  40                  45

Gly Gly Tyr Val Pro Glu Asp Gly Asp Thr Ile Tyr Ala Gln Lys Phe
                    50                  55                  60

Gln Gly Arg Val Thr Met Thr Glu Asp Thr Ser Thr Asp Thr Ala Tyr
            65                  70                  75                  80

Met Glu Leu Ser Ser Leu Arg Ser Glu Asp Thr Ala Val Tyr Tyr Cys
                            85                  90                  95

Ala Thr Asp Pro Leu Tyr Pro Pro Gly Leu Gln Pro Trp Gly Gln Gly
                        100                 105                 110

Thr Thr Val Thr Val Ser Ser
                    115

<210> SEQ ID NO 57
<211> LENGTH: 30
<212> TYPE: DNA
<213> ORGANISM: Artificial Sequence
<220> FEATURE:
<223> OTHER INFORMATION: chemically synthesized

<400> SEQUENCE: 57 gatccctgt atcctccggg gctgcagcct                                             30

<210> SEQ ID NO 58
<211> LENGTH: 10
<212> TYPE: PRT
<213> ORGANISM: Artificial Sequence
<220> FEATURE:
<223> OTHER INFORMATION: chemically synthesized

<400> SEQUENCE: 58

Asp Pro Leu Tyr Pro Pro Gly Leu Gln Pro
1               5                   10

<210> SEQ ID NO 59
<211> LENGTH: 357
<212> TYPE: DNA
<213> ORGANISM: Artificial Sequence
<220> FEATURE:
<223> OTHER INFORMATION: chemically synthesized

<400> SEQUENCE: 59
caggtgcagc tggtgcagtc tggggctgag gtgaagaagc ctggggcctc agtgaaggtt           60
tcctgcaagg tttccggata caccctcaat gacttcgcca tgcactgggt gcgacaggct          120
cctggaaaag ggcttgagtg gatgggaggt tatgttcctg aagatggtga cacaatctac          180
gcgcagaagt tccagggcag agtcaccatg accgaggaca catctacaga cacagcctac          240
atggagctga gcagcctgag atctgaggac acggccgtgt attactgtgc aacagatccc          300
ctgtatagtg ggagcttatc ctactggggg caggggacca cggtcaccgt ctcgagt             357

<210> SEQ ID NO 60
<211> LENGTH: 119
<212> TYPE: PRT
<213> ORGANISM: Artificial Sequence
<220> FEATURE:
<223> OTHER INFORMATION: chemically synthesized

<400> SEQUENCE: 60
```

```
Gln Val Gln Leu Val Gln Ser Gly Ala Glu Val Lys Pro Gly Ala
1               5                   10                  15

Ser Val Lys Val Ser Cys Lys Val Ser Gly Tyr Thr Leu Asn Asp Phe
            20                  25                  30

Ala Met His Trp Val Arg Gln Ala Pro Gly Lys Gly Leu Glu Trp Met
        35                  40                  45

Gly Gly Tyr Val Pro Glu Asp Gly Asp Thr Ile Tyr Ala Gln Lys Phe
    50                  55                  60

Gln Gly Arg Val Thr Met Thr Glu Asp Thr Ser Thr Asp Thr Ala Tyr
65              70                  75                  80

Met Glu Leu Ser Ser Leu Arg Ser Glu Asp Thr Ala Val Tyr Tyr Cys
            85                  90                  95

Ala Thr Asp Pro Leu Tyr Ser Gly Ser Leu Ser Tyr Trp Gly Gln Gly
        100                 105                 110

Thr Thr Val Thr Val Ser Ser
        115
```

<210> SEQ ID NO 61
<211> LENGTH: 324
<212> TYPE: DNA
<213> ORGANISM: Artificial Sequence
<220> FEATURE:
<223> OTHER INFORMATION: chemically synthesized

<400> SEQUENCE: 61

```
tcctatgtgc tgactcagcc accctcggtg tcagtggccc caggacagac ggccaggatt      60
acctgtgggg gaaacaacat tgaaagtaaa agtgtgcact ggtaccagca gaagccaggc     120
caggcccctg tgctggccgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtggtc ctgtgtggtg gattttcggc     300
ggagggacca aggtcaccgt ccta                                            324
```

<210> SEQ ID NO 62
<211> LENGTH: 108
<212> TYPE: PRT
<213> ORGANISM: Artificial Sequence
<220> FEATURE:
<223> OTHER INFORMATION: chemically synthesized

<400> SEQUENCE: 62

```
Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Glu Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65              70                  75                  80

Asp Glu Ala Asp Tyr Tyr Cys Gln Val Trp Asp Ser Gly Pro Val Trp
            85                  90                  95

Trp Ile Phe Gly Gly Gly Thr Lys Leu Thr Val Leu
        100                 105
```

<210> SEQ ID NO 63
<211> LENGTH: 30

```
<212> TYPE: DNA
<213> ORGANISM: Artificial Sequence
<220> FEATURE:
<223> OTHER INFORMATION: chemically synthesized

<400> SEQUENCE: 63
gatcccctgt atagtgggag cttatcctac                                          30

<210> SEQ ID NO 64
<211> LENGTH: 10
<212> TYPE: PRT
<213> ORGANISM: Artificial Sequence
<220> FEATURE:
<223> OTHER INFORMATION: chemically synthesized

<400> SEQUENCE: 64

Asp Pro Leu Tyr Ser Gly Ser Leu Ser Tyr
1               5                   10

<210> SEQ ID NO 65
<211> LENGTH: 34
<212> TYPE: DNA
<213> ORGANISM: Artificial Sequence
<220> FEATURE:
<223> OTHER INFORMATION: chemically synthesized

<400> SEQUENCE: 65
tcaggtgtgg gatagtggtc ctgtgtggtg gatt                                     34

<210> SEQ ID NO 66
<211> LENGTH: 11
<212> TYPE: PRT
<213> ORGANISM: Artificial Sequence
<220> FEATURE:
<223> OTHER INFORMATION: chemically synthesized

<400> SEQUENCE: 66

Gln Val Trp Asp Ser Gly Pro Val Trp Trp Ile
1               5                   10

<210> SEQ ID NO 67
<211> LENGTH: 366
<212> TYPE: DNA
<213> ORGANISM: Artificial Sequence
<220> FEATURE:
<223> OTHER INFORMATION: chemically synthesized

<400> SEQUENCE: 67
caggtgcagc tggtgcagtc tgggactgag gtgaagaagc ctggggctac agtgaatgtt         60
tcctgcaaga tttccggaca cctcttcacc gactactaca tacactgggt gcaacaggcc        120
cctggaaaag ggcttgagtg ggtgggactt attgatccta agatggtga atccaatac         180 gcagagaaat tccaggccag agtcaccatt acagcggaca cgtccacaga cacagtttac        240
atggaattga acagcctgag atctgaagac acggccgtgt attactgtgc aacagaggtt        300
ttaagcggta ttagggtttt cccattcgac ccctggggcc agggcaccct ggtcaccgtc        360
tcgagt                                                                  366

<210> SEQ ID NO 68
<211> LENGTH: 122
<212> TYPE: PRT
<213> ORGANISM: Artificial Sequence
<220> FEATURE:
<223> OTHER INFORMATION: chemically synthesized

<400> SEQUENCE: 68
```

Gln Val Gln Leu Val Gln Ser Gly Thr Glu Val Lys Lys Pro Gly Ala
1               5                   10                  15

Thr Val Asn Val Ser Cys Lys Ile Ser Gly His Leu Phe Thr Asp Tyr
            20                  25                  30

Tyr Ile His Trp Val Gln Gln Ala Pro Gly Lys Gly Leu Glu Trp Val
        35                  40                  45

Gly Leu Ile Asp Pro Lys Asp Gly Glu Ile Gln Tyr Ala Glu Lys Phe
    50                  55                  60

Gln Ala Arg Val Thr Ile Thr Ala Asp Thr Ser Thr Asp Thr Val Tyr
65                  70                  75                  80

Met Glu Leu Asn Ser Leu Arg Ser Glu Asp Thr Ala Val Tyr Tyr Cys
                85                  90                  95

Ala Thr Glu Val Leu Ser Gly Ile Arg Val Phe Pro Phe Asp Pro Trp
            100                 105                 110

Gly Gln Gly Thr Leu Val Thr Val Ser Ser
            115                 120

<210> SEQ ID NO 69
<211> LENGTH: 339
<212> TYPE: DNA
<213> ORGANISM: Artificial Sequence
<220> FEATURE:
<223> OTHER INFORMATION: chemically synthesized

<400> SEQUENCE: 69
cagtctgtgc tgactcagcc accctcagtg tctggggccc cagggcagag ggtcaccatc      60
tcttgcactg ggagcagctc aacatcgggg gcaggttatg atgtatattg gtaccaacag     120
tttccaggga agccccccaa actcctcatc tatgatacca caatcgaccc ccaggggtc     180 cctgatcgat tctctggctc caagtctggc acctcagcct ccctggccat cagtgggctc     240
cagactgaag atgaggctga ttattactgc cagtcttatg acatcgccct gagtaactcg     300
aatgtggttt tcggcggagg gaccaagctg accgtccta                            339

<210> SEQ ID NO 70
<211> LENGTH: 113
<212> TYPE: PRT
<213> ORGANISM: Artificial Sequence
<220> FEATURE:
<223> OTHER INFORMATION: chemically synthesized

<400> SEQUENCE: 70

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val Tyr Trp Tyr Gln Gln Phe Pro Gly Lys Ala Pro Lys Leu
        35                  40                  45

Leu Ile Tyr Asp Thr Asn Asn Arg Pro Pro Gly Val Pro Asp Arg Phe
    50                  55                  60

Ser Gly Ser Lys Ser Gly Thr Ser Ala Ser Leu Ala Ile Ser Gly Leu
65                  70                  75                  80

Gln Thr Glu Asp Glu Ala Asp Tyr Tyr Cys Gln Ser Tyr Asp Ile Ala
                85                  90                  95

Leu Ser Asn Ser Asn Val Val Phe Gly Gly Gly Thr Lys Leu Thr Val
            100                 105                 110

Leu

```
<210> SEQ ID NO 71
<211> LENGTH: 15
<212> TYPE: DNA
<213> ORGANISM: Artificial Sequence
<220> FEATURE:
<223> OTHER INFORMATION: chemically synthesized

<400> SEQUENCE: 71
gactactaca tacac                                                      15

<210> SEQ ID NO 72
<211> LENGTH: 51
<212> TYPE: DNA
<213> ORGANISM: Artificial Sequence
<220> FEATURE:
<223> OTHER INFORMATION: chemically synthesized

<400> SEQUENCE: 72
ggttatgttc ctgaagatgg tgacacaatc tacgcgcaga agttccaggg c               51

<210> SEQ ID NO 73
<211> LENGTH: 39
<212> TYPE: DNA
<213> ORGANISM: Artificial Sequence
<220> FEATURE:
<223> OTHER INFORMATION: chemically synthesized

<400> SEQUENCE: 73
gaggttttaa gcggtattag ggttttccca ttcgacccc                             39

<210> SEQ ID NO 74
<211> LENGTH: 5
<212> TYPE: PRT
<213> ORGANISM: Artificial Sequence
<220> FEATURE:
<223> OTHER INFORMATION: chemically synthesized

<400> SEQUENCE: 74

Asp Tyr Tyr Ile His
1               5

<210> SEQ ID NO 75
<211> LENGTH: 17
<212> TYPE: PRT
<213> ORGANISM: Artificial Sequence
<220> FEATURE:
<223> OTHER INFORMATION: chemically synthesized

<400> SEQUENCE: 75

Leu Ile Asp Pro Lys Asp Gly Glu Ile Gln Tyr Ala Glu Lys Phe Gln
1               5                   10                  15

Ala

<210> SEQ ID NO 76
<211> LENGTH: 13
<212> TYPE: PRT
<213> ORGANISM: Artificial Sequence
<220> FEATURE:
<223> OTHER INFORMATION: chemically synthesized

<400> SEQUENCE: 76

Glu Val Leu Ser Gly Ile Arg Val Phe Pro Phe Asp Pro
1               5                   10

<210> SEQ ID NO 77
<211> LENGTH: 14
```

```
<212> TYPE: PRT
<213> ORGANISM: Artificial Sequence
<220> FEATURE:
<223> OTHER INFORMATION: chemically synthesized

<400> SEQUENCE: 77

Thr Gly Ser Ser Ser Asn Ile Gly Ala Gly Tyr Asp Val Tyr
1               5                   10

<210> SEQ ID NO 78
<211> LENGTH: 21
<212> TYPE: DNA
<213> ORGANISM: Artificial Sequence
<220> FEATURE:
<223> OTHER INFORMATION: chemically synthesized

<400> SEQUENCE: 78
gataccaaca atcgaccccc a                                           21

<210> SEQ ID NO 79
<211> LENGTH: 39
<212> TYPE: DNA
<213> ORGANISM: Artificial Sequence
<220> FEATURE:
<223> OTHER INFORMATION: chemically synthesized

<400> SEQUENCE: 79
cagtcttatg acatcgccct gagtaactcg aatgtggtt                         39

<210> SEQ ID NO 80
<211> LENGTH: 42
<212> TYPE: DNA
<213> ORGANISM: Artificial Sequence
<220> FEATURE:
<223> OTHER INFORMATION: chemically synthesized

<400> SEQUENCE: 80
actgggagca gctccaacat cggggcaggt tatgatgtat at                     42

<210> SEQ ID NO 81
<211> LENGTH: 7
<212> TYPE: PRT
<213> ORGANISM: Artificial Sequence
<220> FEATURE:
<223> OTHER INFORMATION: chemically synthesized

<400> SEQUENCE: 81

Asp Thr Asn Asn Arg Pro Pro
1               5

<210> SEQ ID NO 82
<211> LENGTH: 13
<212> TYPE: PRT
<213> ORGANISM: Artificial Sequence
<220> FEATURE:
<223> OTHER INFORMATION: chemically synthesized

<400> SEQUENCE: 82

Gln Ser Tyr Asp Ile Ala Leu Ser Asn Ser Asn Val Val
1               5                   10

<210> SEQ ID NO 83
<211> LENGTH: 363
<212> TYPE: DNA
<213> ORGANISM: Artificial Sequence
<220> FEATURE:
<223> OTHER INFORMATION: chemically synthesized
```

<400> SEQUENCE: 83

```
caggtgcagc tggtgcagtc tggggctgag gtgaagaagc ctggggcctc agtgaaggtc      60
tcctgcaagg tttccggata caccctcact gaattatcca tgcactgggt gcgacaggct     120
cctggaaaag gcttgagtg gatgggaggt tttgatcctg aagatggtga acaatctac       180
gcacagaagt tccagggcag agtcaccatg accgaggaca tcctacaga cacagcctac      240
atggagctga gcagcctgag atctgaggac acggccgtgt attactgtgc aacttattct    300
ggtagtagtg gttggtgggc ttttgatatc tggggccaag gacaatggt caccgtctcg      360
agt                                                                   363
```

<210> SEQ ID NO 84
<211> LENGTH: 121
<212> TYPE: PRT
<213> ORGANISM: Artificial Sequence
<220> FEATURE:
<223> OTHER INFORMATION: chemically synthesized

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Tyr Ser Gly Ser Ser Gly Trp Trp Ala Phe Asp Ile Trp Gly
            100                 105                 110

Gln Gly Thr Met Val Thr Val Ser Ser
        115                 120

<210> SEQ ID NO 85
<211> LENGTH: 318
<212> TYPE: DNA
<213> ORGANISM: Artificial Sequence
<220> FEATURE:
<223> OTHER INFORMATION: chemically synthesized

<400> SEQUENCE: 85

```
tcttctgagc tgactcagga ccctgctgtg tctgtggcct tgggacagac agtcaggatc      60
acatgccaag agacagcct cagaagctat atgcaagct ggtaccagca gaagccagga       120
caggcccctg tacttgtcat ctatggtaaa acaaccggc cctcaggat cccagaccga      180
ttctctggct ccagctcagg aaacacagct tccttgacca tcactggggc tcaggcggaa    240
gatgaggctg actattactg tcagacctgg ggcactggca tttgggtgtt cggcggaggg      300
accaagctga ccgtcccta                                                   318
```

<210> SEQ ID NO 86
<211> LENGTH: 106
<212> TYPE: PRT
<213> ORGANISM: Artificial Sequence
<220> FEATURE:
<223> OTHER INFORMATION: chemically synthesized

<400> SEQUENCE: 86

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Gln Thr Trp Gly Thr Gly Ile Trp Val
                85                  90                  95

Phe Gly Gly Gly Thr Lys Leu Thr Val Leu
                100                 105

<210> SEQ ID NO 87
<211> LENGTH: 15
<212> TYPE: DNA
<213> ORGANISM: Artificial Sequence
<220> FEATURE:
<223> OTHER INFORMATION: chemically synthesized

<400> SEQUENCE: 87
gaattatcca tgcac                                             15

<210> SEQ ID NO 88
<211> LENGTH: 51
<212> TYPE: DNA
<213> ORGANISM: Artificial Sequence
<220> FEATURE:
<223> OTHER INFORMATION: chemically synthesized

<400> SEQUENCE: 88
ggttttgatc ctgaagatgg tgaaacaatc tacgcacaga gttccagggc          51

<210> SEQ ID NO 89
<211> LENGTH: 36
<212> TYPE: DNA
<213> ORGANISM: Artificial Sequence
<220> FEATURE:
<223> OTHER INFORMATION: chemically synthesized

<400> SEQUENCE: 89
tattctggta gtagtggttg gtgggctttt gatatc                      36

<210> SEQ ID NO 90
<211> LENGTH: 5
<212> TYPE: PRT
<213> ORGANISM: Artificial Sequence
<220> FEATURE:
<223> OTHER INFORMATION: chemically synthesized

<400> SEQUENCE: 90

Glu Leu Ser Met His
1               5

<210> SEQ ID NO 91
<211> LENGTH: 17
<212> TYPE: PRT
<213> ORGANISM: Artificial Sequence
<220> FEATURE:
<223> OTHER INFORMATION: chemically synthesized

```
<400> SEQUENCE: 91

Gly Phe Asp Pro Glu Asp Gly Glu Thr Ile Tyr Ala Gln Lys Phe Gln
1               5                   10                  15

Gly

<210> SEQ ID NO 92
<211> LENGTH: 12
<212> TYPE: PRT
<213> ORGANISM: Artificial Sequence
<220> FEATURE:
<223> OTHER INFORMATION: chemically synthesized

<400> SEQUENCE: 92

Tyr Ser Gly Ser Ser Gly Trp Trp Ala Phe Asp Ile
1               5                   10

<210> SEQ ID NO 93
<211> LENGTH: 33
<212> TYPE: DNA
<213> ORGANISM: Artificial Sequence
<220> FEATURE:
<223> OTHER INFORMATION: chemically synthesized

<400> SEQUENCE: 93
caaggagaca gcctcagaag ctattatgca agc                              33

<210> SEQ ID NO 94
<211> LENGTH: 21
<212> TYPE: DNA
<213> ORGANISM: Artificial Sequence
<220> FEATURE:
<223> OTHER INFORMATION: chemically synthesized

<400> SEQUENCE: 94
ggtaaaaaca accggccctc a                                           21

<210> SEQ ID NO 95
<211> LENGTH: 27
<212> TYPE: DNA
<213> ORGANISM: Artificial Sequence
<220> FEATURE:
<223> OTHER INFORMATION: chemically synthesized

<400> SEQUENCE: 95
cagacctggg gcactggcat ttgggtg                                     27

<210> SEQ ID NO 96
<211> LENGTH: 11
<212> TYPE: PRT
<213> ORGANISM: Artificial Sequence
<220> FEATURE:
<223> OTHER INFORMATION: chemically synthesized

<400> SEQUENCE: 96

Gln Gly Asp Ser Leu Arg Ser Tyr Tyr Ala Ser
1               5                   10

<210> SEQ ID NO 97
<211> LENGTH: 7
<212> TYPE: PRT
<213> ORGANISM: Artificial Sequence
<220> FEATURE:
<223> OTHER INFORMATION: chemically synthesized

<400> SEQUENCE: 97

Gly Lys Asn Asn Arg Pro Ser
```

<210> SEQ ID NO 98
<211> LENGTH: 9
<212> TYPE: PRT
<213> ORGANISM: Artificial Sequence
<220> FEATURE:
<223> OTHER INFORMATION: chemically synthesized

<400> SEQUENCE: 98

Gln Thr Trp Gly Thr Gly Ile Trp Val
1               5

<210> SEQ ID NO 99
<211> LENGTH: 372
<212> TYPE: DNA
<213> ORGANISM: Artificial Sequence
<220> FEATURE:
<223> OTHER INFORMATION: chemically synthesized

<400> SEQUENCE: 99
gaggtgcagc tggtggagtc cggggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagattta     300
ggatattgta ctaatggtgt atgctggggt attgactact ggggccaggg gacaatggtc     360
accgtctcga gt                                                          372

<210> SEQ ID NO 100
<211> LENGTH: 124
<212> TYPE: PRT
<213> ORGANISM: Artificial Sequence
<220> FEATURE:
<223> OTHER INFORMATION: chemically synthesized

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Tyr Cys Thr Asn Gly Val Cys Trp Gly Ile Asp
            100                 105                 110

Tyr Trp Gly Gln Gly Thr Met Val Thr Val Ser Ser
        115                 120

<210> SEQ ID NO 101
<211> LENGTH: 330
<212> TYPE: DNA
<213> ORGANISM: Artificial Sequence
<220> FEATURE:
<223> OTHER INFORMATION: chemically synthesized

<400> SEQUENCE: 101

| | | | |
|---|---|---|---|
| aattttatgc tgactcagcc ccactctgtg tcggagtctc cggggaagac ggtaaccatc | | | 60 |
| tcctgcaccc gcagcagtgg cagcattgcc gacaactatg tgcagtggta ccagcagcgc | | | 120 |
| ccgggcagtg cccccaccac tatcatctat gacgatgacc aaagactctc tggggtccct | | | 180 |
| gatcgattct ctggctccat tgacacttcc tccaactctg cctccctctc catctctgga | | | 240 |
| ctgaggactg aggacgaggc tgattactac tgtcagtctt atgatgactc caatgatgtg | | | 300 |
| ttcggcggag ggaccaagct gaccgtccta | | | 330 |

<210> SEQ ID NO 102
<211> LENGTH: 110
<212> TYPE: PRT
<213> ORGANISM: Artificial Sequence
<220> FEATURE:
<223> OTHER INFORMATION: chemically synthesized

<400> SEQUENCE: 102

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Asp Asn
            20                  25                  30

Tyr Val Gln Trp Tyr Gln Gln Arg Pro Gly Ser Ala Pro Thr Thr Ile
        35                  40                  45

Ile Tyr Asp Asp Asp Gln Arg Leu Ser Gly Val Pro Asp Arg Phe Ser
    50                  55                  60

Gly Ser Ile Asp Thr Ser Ser Asn Ser Ala Ser Leu Ser Ile Ser Gly
65                  70                  75                  80

Leu Arg Thr Glu Asp Glu Ala Asp Tyr Tyr Cys Gln Ser Tyr Asp Asp
                85                  90                  95

Ser Asn Asp Val Phe Gly Gly Gly Thr Lys Leu Thr Val Leu
            100                 105                 110

<210> SEQ ID NO 103
<211> LENGTH: 15
<212> TYPE: DNA
<213> ORGANISM: Artificial Sequence
<220> FEATURE:
<223> OTHER INFORMATION: chemically synthesized

<400> SEQUENCE: 103
agctatgcca tgagc                                                    15

<210> SEQ ID NO 104
<211> LENGTH: 51
<212> TYPE: DNA
<213> ORGANISM: Artificial Sequence
<220> FEATURE:
<223> OTHER INFORMATION: chemically synthesized

<400> SEQUENCE: 104
gctattagtg gtagtggtgg tagcacatac tacgcagact ccgtgaaggg c             51

<210> SEQ ID NO 105
<211> LENGTH: 45
<212> TYPE: DNA
<213> ORGANISM: Artificial Sequence
<220> FEATURE:
<223> OTHER INFORMATION: chemically synthesized

<400> SEQUENCE: 105
gatttaggat attgtactaa tggtgtatgc tggggtattg actac    45

<210> SEQ ID NO 106
<211> LENGTH: 5
<212> TYPE: PRT
<213> ORGANISM: Artificial Sequence
<220> FEATURE:
<223> OTHER INFORMATION: chemically synthesized

<400> SEQUENCE: 106

Ser Tyr Ala Met Ser
1               5

<210> SEQ ID NO 107
<211> LENGTH: 17
<212> TYPE: PRT
<213> ORGANISM: Artificial Sequence
<220> FEATURE:
<223> OTHER INFORMATION: chemically synthesized

<400> SEQUENCE: 107

Ala Ile Ser Gly Ser Gly Gly Ser Thr Tyr Tyr Ala Asp Ser Val Lys
1               5                   10                  15
Gly

<210> SEQ ID NO 108
<211> LENGTH: 15
<212> TYPE: PRT
<213> ORGANISM: Artificial Sequence
<220> FEATURE:
<223> OTHER INFORMATION: chemically synthesized

<400> SEQUENCE: 108

Asp Leu Gly Tyr Cys Thr Asn Gly Val Cys Trp Gly Ile Asp Tyr
1               5                   10                  15

<210> SEQ ID NO 109
<211> LENGTH: 39
<212> TYPE: DNA
<213> ORGANISM: Artificial Sequence
<220> FEATURE:
<223> OTHER INFORMATION: chemically synthesized

<400> SEQUENCE: 109
acccgcagca gtggcagcat tgccgacaac tatgtgcag    39

<210> SEQ ID NO 110
<211> LENGTH: 21
<212> TYPE: DNA
<213> ORGANISM: Artificial Sequence
<220> FEATURE:
<223> OTHER INFORMATION: chemically synthesized

<400> SEQUENCE: 110
gacgatgacc aaagactctc t    21

<210> SEQ ID NO 111
<211> LENGTH: 27
<212> TYPE: DNA
<213> ORGANISM: Artificial Sequence
<220> FEATURE:
<223> OTHER INFORMATION: chemically synthesized

<400> SEQUENCE: 111
cagtcttatg atgactccaa tgatgtg    27

<210> SEQ ID NO 112
<211> LENGTH: 13
<212> TYPE: PRT
<213> ORGANISM: Artificial Sequence
<220> FEATURE:
<223> OTHER INFORMATION: chemically synthesized

<400> SEQUENCE: 112

```
Thr Arg Ser Ser Gly Ser Ile Ala Asp Asn Tyr Val Gln
1               5                   10
```

<210> SEQ ID NO 113
<211> LENGTH: 7
<212> TYPE: PRT
<213> ORGANISM: Artificial Sequence
<220> FEATURE:
<223> OTHER INFORMATION: chemically synthesized

<400> SEQUENCE: 113

```
Asp Asp Asp Gln Arg Leu Ser
1               5
```

<210> SEQ ID NO 114
<211> LENGTH: 9
<212> TYPE: PRT
<213> ORGANISM: Artificial Sequence
<220> FEATURE:
<223> OTHER INFORMATION: chemically synthesized

<400> SEQUENCE: 114

```
Gln Ser Tyr Asp Asp Ser Asn Asp Val
1               5
```

<210> SEQ ID NO 115
<211> LENGTH: 369
<212> TYPE: DNA
<213> ORGANISM: Artificial Sequence
<220> FEATURE:
<223> OTHER INFORMATION: chemically synthesized

<400> SEQUENCE: 115

```
caggtgcagc tggtgcagtc tggggctgag gtggagaagc ctggggcctc agtgaaggtc      60
tcctgcaggg tttcgggata ccccctcact gaaatagcca tacactgggt gcgacaggct     120
cctggaaaag ggcttgagtg gatgggaagt tttgagcctg aagatgctga agcaatctac     180
gcacagaggt tccagggcag agtcacaatg accgaggaaa catctgcaaa cactgcctac     240
atggagctga gcagcctgag atctgaggac acggccgtgt atttctgtgc aacagatccc     300
tactatgcta gcagtggttc taactacatg gaggtctggg gccgaggaac cctggtcacc     360
gtctcgagt                                                            369
```

<210> SEQ ID NO 116
<211> LENGTH: 123
<212> TYPE: PRT
<213> ORGANISM: Artificial Sequence
<220> FEATURE:
<223> OTHER INFORMATION: chemically synthesized

<400> SEQUENCE: 116

```
Gln Val Gln Leu Val Gln Ser Gly Ala Glu Val Glu Lys Pro Gly Ala
1               5                   10                  15

Ser Val Lys Val Ser Cys Arg Val Ser Gly Tyr Pro Leu Thr Glu Ile
            20                  25                  30

Ala Ile His Trp Val Arg Gln Ala Pro Gly Lys Gly Leu Glu Trp Met
        35                  40                  45
```

```
Gly Ser Phe Glu Pro Glu Asp Ala Glu Ala Ile Tyr Ala Gln Arg Phe
    50                  55                  60

Gln Gly Arg Val Thr Met Thr Glu Thr Ser Ala Asn Thr Ala Tyr
65                  70                  75                  80

Met Glu Leu Ser Ser Leu Arg Ser Glu Asp Thr Ala Val Tyr Phe Cys
                85                  90                  95

Ala Thr Asp Pro Tyr Tyr Ala Ser Ser Gly Ser Asn Tyr Met Glu Val
                100                 105                 110

Trp Gly Arg Gly Thr Leu Val Thr Val Ser Ser
            115                 120
```

<210> SEQ ID NO 117
<211> LENGTH: 333
<212> TYPE: DNA
<213> ORGANISM: Artificial Sequence
<220> FEATURE:
<223> OTHER INFORMATION: chemically synthesized

<400> SEQUENCE: 117

```
aattttatgc tgactcagcc ccactctgtg tcggagtctc cggggaagac ggtaaccatt     60
tcctgcaccg gcagcggcgg cagcatttcc agcaactatg tccagtggta ccgacagcgc    120
ccgggcagcg cccccagcac tgtgatctat gaggatgacc aaagaccctc tggggtccct    180
gatcggatct ctggctccat cgacagttcc tccaactctg cctccctcac catctctgga    240
ctgacaactg aggacgaggc tgactactat tgtcactctt atgatggcaa caatcggtgg    300
gtcttcggcg agggaccaa gctgaccgtc cta                                  333
```

<210> SEQ ID NO 118
<211> LENGTH: 111
<212> TYPE: PRT
<213> ORGANISM: Artificial Sequence
<220> FEATURE:
<223> OTHER INFORMATION: chemically synthesized

<400> SEQUENCE: 118

```
Asn Phe Met Leu Thr Gln Pro His Ser Val Ser Glu Ser Pro Gly Lys
1               5                   10                  15

Thr Val Thr Ile Ser Cys Thr Gly Ser Gly Gly Ser Ile Ser Ser Asn
                20                  25                  30

Tyr Val Gln Trp Tyr Arg Gln Arg Pro Gly Ser Ala Pro Ser Thr Val
            35                  40                  45

Ile Tyr Glu Asp Asp Gln Arg Pro Ser Gly Val Pro Asp Arg Ile Ser
    50                  55                  60

Gly Ser Ile Asp Ser Ser Ser Asn Ser Ala Ser Leu Thr Ile Ser Gly
65                  70                  75                  80

Leu Thr Thr Glu Asp Glu Ala Asp Tyr Tyr Cys His Ser Tyr Asp Gly
                85                  90                  95

Asn Asn Arg Trp Val Phe Gly Gly Gly Thr Lys Leu Thr Val Leu
                100                 105                 110
```

<210> SEQ ID NO 119
<211> LENGTH: 15
<212> TYPE: DNA
<213> ORGANISM: Artificial Sequence
<220> FEATURE:
<223> OTHER INFORMATION: chemically synthesized

<400> SEQUENCE: 119

```
gaaatagcca tacac                                                      15
```

<210> SEQ ID NO 120
<211> LENGTH: 51
<212> TYPE: DNA
<213> ORGANISM: Artificial Sequence
<220> FEATURE:
<223> OTHER INFORMATION: chemically synthesized

<400> SEQUENCE: 120
agttttgagc ctgaagatgc tgaagcaatc tacgcacaga ggttccaggg c          51

<210> SEQ ID NO 121
<211> LENGTH: 42
<212> TYPE: DNA
<213> ORGANISM: Artificial Sequence
<220> FEATURE:
<223> OTHER INFORMATION: chemically synthesized

<400> SEQUENCE: 121
gatccctact atgctagcag tggttctaac tacatggagg tc                    42

<210> SEQ ID NO 122
<211> LENGTH: 5
<212> TYPE: PRT
<213> ORGANISM: Artificial Sequence
<220> FEATURE:
<223> OTHER INFORMATION: chemically synthesized

<400> SEQUENCE: 122

Glu Ile Ala Ile His
1               5

<210> SEQ ID NO 123
<211> LENGTH: 17
<212> TYPE: PRT
<213> ORGANISM: Artificial Sequence
<220> FEATURE:
<223> OTHER INFORMATION: chemically synthesized

<400> SEQUENCE: 123

Ser Phe Glu Pro Glu Asp Ala Glu Ala Ile Tyr Ala Gln Arg Phe Gln
1               5                   10                  15

Gly

<210> SEQ ID NO 124
<211> LENGTH: 14
<212> TYPE: PRT
<213> ORGANISM: Artificial Sequence
<220> FEATURE:
<223> OTHER INFORMATION: chemically synthesized

<400> SEQUENCE: 124

Asp Pro Tyr Tyr Ala Ser Ser Gly Ser Asn Tyr Met Glu Val
1               5                   10

<210> SEQ ID NO 125
<211> LENGTH: 39
<212> TYPE: DNA
<213> ORGANISM: Artificial Sequence
<220> FEATURE:
<223> OTHER INFORMATION: chemically synthesized

<400> SEQUENCE: 125
accggcagcg gcggcagcat ttccagcaac tatgtccag                        39

<210> SEQ ID NO 126

```
<211> LENGTH: 21
<212> TYPE: DNA
<213> ORGANISM: Artificial Sequence
<220> FEATURE:
<223> OTHER INFORMATION: chemically synthesized

<400> SEQUENCE: 126
gaggatgacc aaagaccctc t                                              21

<210> SEQ ID NO 127
<211> LENGTH: 30
<212> TYPE: DNA
<213> ORGANISM: Artificial Sequence
<220> FEATURE:
<223> OTHER INFORMATION: chemically synthesized

<400> SEQUENCE: 127
cactcttatg atggcaacaa tcggtgggtc                                     30

<210> SEQ ID NO 128
<211> LENGTH: 13
<212> TYPE: PRT
<213> ORGANISM: Artificial Sequence
<220> FEATURE:
<223> OTHER INFORMATION: chemically synthesized

<400> SEQUENCE: 128

Thr Gly Ser Gly Gly Ser Ile Ser Ser Asn Tyr Val Gln
1               5                   10

<210> SEQ ID NO 129
<211> LENGTH: 7
<212> TYPE: PRT
<213> ORGANISM: Artificial Sequence
<220> FEATURE:
<223> OTHER INFORMATION: chemically synthesized

<400> SEQUENCE: 129

Glu Asp Asp Gln Arg Pro Ser
1               5

<210> SEQ ID NO 130
<211> LENGTH: 10
<212> TYPE: PRT
<213> ORGANISM: Artificial Sequence
<220> FEATURE:
<223> OTHER INFORMATION: chemically synthesized

<400> SEQUENCE: 130

His Ser Tyr Asp Gly Asn Asn Arg Trp Val
1               5                   10

<210> SEQ ID NO 131
<211> LENGTH: 366
<212> TYPE: DNA
<213> ORGANISM: Artificial Sequence
<220> FEATURE:
<223> OTHER INFORMATION: chemically synthesized

<400> SEQUENCE: 131
caggtgcagc tggtgcagtc tggggctgag gtgaagaggc ctggggcctc agtgaaggtc    60
tcctgcaaag tttccggaaa caccctcagt aaacaatcca tgcactgggt gcgacaggct   120
cctggaaaag ggtttgagtg gatgggaagt tctaatcctg aagatgatga aacactctac   180
gcaaagaagt tccagggcag agtcaccatg accgaggaca catccacaga cacagcctat   240
ttggagttga gcagtctgag gtctgaggac acggccgtgt attattgtgc aacagactcc   300
```

```
cagggttttt actattacta cggtatggac gtctggggcc agggcaccct ggtcaccgtc     360
tcgagt                                                                366

<210> SEQ ID NO 132
<211> LENGTH: 122
<212> TYPE: PRT
<213> ORGANISM: Artificial Sequence
<220> FEATURE:
<223> OTHER INFORMATION: chemically synthesized

<400> SEQUENCE: 132

Gln Val Gln Leu Val Gln Ser Gly Ala Glu Val Lys Arg Pro Gly Ala
1               5                   10                  15

Ser Val Lys Val Ser Cys Lys Val Ser Gly Asn Thr Leu Ser Lys Gln
            20                  25                  30

Ser Met His Trp Val Arg Gln Ala Pro Gly Lys Gly Phe Glu Trp Met
        35                  40                  45

Gly Ser Ser Asn Pro Glu Asp Asp Glu Thr Leu Tyr Ala Lys Lys Phe
    50                  55                  60

Gln Gly Arg Val Thr Met Thr Glu Asp Thr Ser Thr Asp Thr Ala Tyr
65                  70                  75                  80

Leu Glu Leu Ser Ser Leu Arg Ser Glu Asp Thr Ala Val Tyr Tyr Cys
                85                  90                  95

Ala Thr Asp Ser Gln Gly Phe Tyr Tyr Tyr Gly Met Asp Val Trp
            100                 105                 110

Gly Gln Gly Thr Leu Val Thr Val Ser Ser
        115                 120

<210> SEQ ID NO 133
<211> LENGTH: 333
<212> TYPE: DNA
<213> ORGANISM: Artificial Sequence
<220> FEATURE:
<223> OTHER INFORMATION: chemically synthesized

<400> SEQUENCE: 133
cagtctgtgc tgactcagcc gccctcagtg tctggggccc cagggcagag ggtcaccatc      60
tcctgcactg ggagcagctc caacatcggg gcagattatg atgtacactg gtaccagcaa     120
cttccaggaa cagtccccaa actcctcatc tatgataaca tcaatcggcc ctcaggggtc     180
cctgaccgat tctctggctc caagtctggc acctcagcct ccctggccat cactgggctc     240
caggctgagg atgaggctga ttattactgc cagtcctatg acagcagcct gagtggtgtg     300
ctattcggcg agggaccaa ggtcaccgtc cta                                    333

<210> SEQ ID NO 134
<211> LENGTH: 111
<212> TYPE: PRT
<213> ORGANISM: Artificial Sequence
<220> FEATURE:
<223> OTHER INFORMATION: chemically synthesized

<400> SEQUENCE: 134

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Asp
            20                  25                  30

Tyr Asp Val His Trp Tyr Gln Gln Leu Pro Gly Thr Val Pro Lys Leu
        35                  40                  45
```

```
Leu Ile Tyr Asp Asn Ile Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Leu Phe Gly Gly Gly Thr Lys Val Thr Val Leu
            100                 105                 110
```

<210> SEQ ID NO 135
<211> LENGTH: 15
<212> TYPE: DNA
<213> ORGANISM: Artificial Sequence
<220> FEATURE:
<223> OTHER INFORMATION: chemically synthesized

<400> SEQUENCE: 135
aaacaatcca tgcac                                                        15

<210> SEQ ID NO 136
<211> LENGTH: 51
<212> TYPE: DNA
<213> ORGANISM: Artificial Sequence
<220> FEATURE:
<223> OTHER INFORMATION: chemically synthesized

<400> SEQUENCE: 136
agttctaatc ctgaagatga tgaaacactc tacgcaaaga agttccaggg c                51

<210> SEQ ID NO 137
<211> LENGTH: 39
<212> TYPE: DNA
<213> ORGANISM: Artificial Sequence
<220> FEATURE:
<223> OTHER INFORMATION: chemically synthesized

<400> SEQUENCE: 137
gactcccagg gttttactat tactacggt atggacgtc                               39

<210> SEQ ID NO 138
<211> LENGTH: 5
<212> TYPE: PRT
<213> ORGANISM: Artificial Sequence
<220> FEATURE:
<223> OTHER INFORMATION: chemically synthesized

<400> SEQUENCE: 138

Lys Gln Ser Met His
1               5

<210> SEQ ID NO 139
<211> LENGTH: 17
<212> TYPE: PRT
<213> ORGANISM: Artificial Sequence
<220> FEATURE:
<223> OTHER INFORMATION: chemically synthesized

<400> SEQUENCE: 139

Ser Ser Asn Pro Glu Asp Asp Glu Thr Leu Tyr Ala Lys Lys Phe Gln
1               5                   10                  15

Gly

<210> SEQ ID NO 140
<211> LENGTH: 13
<212> TYPE: PRT

<213> ORGANISM: Artificial Sequence
<220> FEATURE:
<223> OTHER INFORMATION: chemically synthesized

<400> SEQUENCE: 140

Asp Ser Gln Gly Phe Tyr Tyr Tyr Tyr Gly Met Asp Val
1               5                   10

<210> SEQ ID NO 141
<211> LENGTH: 42
<212> TYPE: DNA
<213> ORGANISM: Artificial Sequence
<220> FEATURE:
<223> OTHER INFORMATION: chemically synthesized

<400> SEQUENCE: 141
actgggagca gctccaacat cggggcagat tatgatgtac ac        42

<210> SEQ ID NO 142
<211> LENGTH: 21
<212> TYPE: DNA
<213> ORGANISM: Artificial Sequence
<220> FEATURE:
<223> OTHER INFORMATION: chemically synthesized

<400> SEQUENCE: 142
gataacatca atcggccctc a        21

<210> SEQ ID NO 143
<211> LENGTH: 33
<212> TYPE: DNA
<213> ORGANISM: Artificial Sequence
<220> FEATURE:
<223> OTHER INFORMATION: chemically synthesized

<400> SEQUENCE: 143
cagtcctatg acagcagcct gagtggtgtg cta        33

<210> SEQ ID NO 144
<211> LENGTH: 14
<212> TYPE: PRT
<213> ORGANISM: Artificial Sequence
<220> FEATURE:
<223> OTHER INFORMATION: chemically synthesized

<400> SEQUENCE: 144

Thr Gly Ser Ser Ser Asn Ile Gly Ala Asp Tyr Asp Val His
1               5                   10

<210> SEQ ID NO 145
<211> LENGTH: 7
<212> TYPE: PRT
<213> ORGANISM: Artificial Sequence
<220> FEATURE:
<223> OTHER INFORMATION: chemically synthesized

<400> SEQUENCE: 145

Asp Asn Ile Asn Arg Pro Ser
1               5

<210> SEQ ID NO 146
<211> LENGTH: 11
<212> TYPE: PRT
<213> ORGANISM: Artificial Sequence
<220> FEATURE:
<223> OTHER INFORMATION: chemically synthesized

<400> SEQUENCE: 146

Gln Ser Tyr Asp Ser Ser Leu Ser Gly Val Leu
1               5                   10

<210> SEQ ID NO 147
<211> LENGTH: 351
<212> TYPE: DNA
<213> ORGANISM: Artificial Sequence
<220> FEATURE:
<223> OTHER INFORMATION: chemically synthesized

<400> SEQUENCE: 147

```
caggtgcagc tggtgcagtc tggggctgag gtgaagaagc ctggggcctc agtgaaggtc    60
tcctgcaggg cttcgggata cgccctcact gaattatcca ttcactgggt gcgacaggct   120
cctggaaaag gcttgagtg gatgggaggt tttgatcctg aagatggtga acaatctac    180
gcacagaatt ccagggcag agtcatcatg accgaggaca catctacaga cacagcctac   240
atggagctga gcagcctgaa atctgaggac acggccgtgt attattgtgc gacagatcta   300
actggaagta gggactcctg gggccaaggc accctggtca ccgtctcgag t            351
```

<210> SEQ ID NO 148
<211> LENGTH: 117
<212> TYPE: PRT
<213> ORGANISM: Artificial Sequence
<220> FEATURE:
<223> OTHER INFORMATION: chemically synthesized

<400> SEQUENCE: 148

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Ala Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Asn Phe
    50                  55                  60

Gln Gly Arg Val Ile Met Thr Glu Asp Thr Ser Thr Asp Thr Ala Tyr
65                  70                  75                  80

Met Glu Leu Ser Ser Leu Lys Ser Glu Asp Thr Ala Val Tyr Tyr Cys
                85                  90                  95

Ala Thr Asp Leu Thr Gly Ser Arg Asp Ser Trp Gly Gln Gly Thr Leu
            100                 105                 110

Val Thr Val Ser Ser
        115

<210> SEQ ID NO 149
<211> LENGTH: 333
<212> TYPE: DNA
<213> ORGANISM: Artificial Sequence
<220> FEATURE:
<223> OTHER INFORMATION: chemically synthesized

<400> SEQUENCE: 149

```
cagtctgtgc tgactcagcc tgcctccgtg tctgggtctc ctggacagtc gatcaccatc    60
tcctgcactg gaagcaggag tgacattggt tactataact atgtctcctg gtaccaacaa   120
cacccaggga agtccccaa actcataatt tatgatgtca ctgagcgacc ctcaggggtt   180
tctgatcgct tctctggctc caagtctgcc aacacggcct ccctgaccat ctctgggctc   240
caggctgagg acgaggctga ttattactgc agctcatttt caagtggcga caccttcgtg   300
```

```
gttttcggcg agggaccaa gctgaccgtc cta                                    333
```

<210> SEQ ID NO 150
<211> LENGTH: 111
<212> TYPE: PRT
<213> ORGANISM: Artificial Sequence
<220> FEATURE:
<223> OTHER INFORMATION: chemically synthesized

<400> SEQUENCE: 150

```
Gln Ser Val Leu Thr Gln Pro Ala Ser Val Ser Gly Ser Pro Gly Gln
1               5                   10                  15

Ser Ile Thr Ile Ser Cys Thr Gly Ser Arg Ser Asp Ile Gly Tyr Tyr
            20                  25                  30

Asn Tyr Val Ser Trp Tyr Gln Gln His Pro Gly Lys Val Pro Lys Leu
        35                  40                  45

Ile Ile Tyr Asp Val Thr Glu Arg Pro Ser Gly Val Ser Asp Arg Phe
    50                  55                  60

Ser Gly Ser Lys Ser Ala Asn Thr Ala Ser Leu Thr Ile Ser Gly Leu
65                  70                  75                  80

Gln Ala Glu Asp Glu Ala Asp Tyr Tyr Cys Ser Ser Phe Ser Ser Gly
                85                  90                  95

Asp Thr Phe Val Val Phe Gly Gly Gly Thr Lys Leu Thr Val Leu
            100                 105                 110
```

<210> SEQ ID NO 151
<211> LENGTH: 15
<212> TYPE: DNA
<213> ORGANISM: Artificial Sequence
<220> FEATURE:
<223> OTHER INFORMATION: chemically synthesized

<400> SEQUENCE: 151

```
gaattatcca ttcac                                                        15
```

<210> SEQ ID NO 152
<211> LENGTH: 51
<212> TYPE: DNA
<213> ORGANISM: Artificial Sequence
<220> FEATURE:
<223> OTHER INFORMATION: chemically synthesized

<400> SEQUENCE: 152

```
ggttttgatc ctgaagatgg tgaaacaatc tacgcacaga atttccaggg c                51
```

<210> SEQ ID NO 153
<211> LENGTH: 24
<212> TYPE: DNA
<213> ORGANISM: Artificial Sequence
<220> FEATURE:
<223> OTHER INFORMATION: chemically synthesized

<400> SEQUENCE: 153

```
gatctaactg gaagtaggga ctcc                                              24
```

<210> SEQ ID NO 154
<211> LENGTH: 5
<212> TYPE: PRT
<213> ORGANISM: Artificial Sequence
<220> FEATURE:
<223> OTHER INFORMATION: chemically synthesized

<400> SEQUENCE: 154

Glu Leu Ser Ile His

```
                            1               5

<210> SEQ ID NO 155
<211> LENGTH: 17
<212> TYPE: PRT
<213> ORGANISM: Artificial Sequence
<220> FEATURE:
<223> OTHER INFORMATION: chemically synthesized

<400> SEQUENCE: 155

Gly Phe Asp Pro Glu Asp Gly Glu Thr Ile Tyr Ala Gln Asn Phe Gln
1               5                   10                  15

Gly

<210> SEQ ID NO 156
<211> LENGTH: 8
<212> TYPE: PRT
<213> ORGANISM: Artificial Sequence
<220> FEATURE:
<223> OTHER INFORMATION: chemically synthesized

<400> SEQUENCE: 156

Asp Leu Thr Gly Ser Arg Asp Ser
1               5

<210> SEQ ID NO 157
<211> LENGTH: 42
<212> TYPE: DNA
<213> ORGANISM: Artificial Sequence
<220> FEATURE:
<223> OTHER INFORMATION: chemically synthesized

<400> SEQUENCE: 157
actggaagca ggagtgacat tggttactat aactatgtct cc                          42

<210> SEQ ID NO 158
<211> LENGTH: 21
<212> TYPE: DNA
<213> ORGANISM: Artificial Sequence
<220> FEATURE:
<223> OTHER INFORMATION: chemically synthesized

<400> SEQUENCE: 158
gatgtcactg agcgaccctc a                                                 21

<210> SEQ ID NO 159
<211> LENGTH: 33
<212> TYPE: DNA
<213> ORGANISM: Artificial Sequence
<220> FEATURE:
<223> OTHER INFORMATION: chemically synthesized

<400> SEQUENCE: 159
agctcatttt caagtggcga caccttcgtg gtt                                    33

<210> SEQ ID NO 160
<211> LENGTH: 14
<212> TYPE: PRT
<213> ORGANISM: Artificial Sequence
<220> FEATURE:
<223> OTHER INFORMATION: chemically synthesized

<400> SEQUENCE: 160

Thr Gly Ser Arg Ser Asp Ile Gly Tyr Tyr Asn Tyr Val Ser
1               5                   10
```

```
<210> SEQ ID NO 161
<211> LENGTH: 7
<212> TYPE: PRT
<213> ORGANISM: Artificial Sequence
<220> FEATURE:
<223> OTHER INFORMATION: chemically synthesized

<400> SEQUENCE: 161

Asp Val Thr Glu Arg Pro Ser
1               5

<210> SEQ ID NO 162
<211> LENGTH: 11
<212> TYPE: PRT
<213> ORGANISM: Artificial Sequence
<220> FEATURE:
<223> OTHER INFORMATION: chemically synthesized

<400> SEQUENCE: 162

Ser Ser Phe Ser Ser Gly Asp Thr Phe Val Val
1               5                   10

<210> SEQ ID NO 163
<211> LENGTH: 366
<212> TYPE: DNA
<213> ORGANISM: Artificial Sequence
<220> FEATURE:
<223> OTHER INFORMATION: chemically synthesized

<400> SEQUENCE: 163
caggtgcagc tggtggagtc tgggggaggc gtggtccagc ctggggaggtc cctgagactc      60 tcctgtgcag cctctggatt caccttcagt agctatgcta tgcactgggt ccgccaggct     120
ccaggcaagg ggctagagtg ggtggcagtt atatcatatg atggaagtaa taaatactac     180
gcagactccg tgaagggccg attctccatc tccagagaca attccaagaa cacgctgtat     240
ctgcaaatga acagcctgag agctgaggac acggctgtgt attactgtgc gagagaaact     300 ttccccccact actactacta ctacatggac gtctggggca aggggacaat ggtcaccgtc     360
tcgagt                                                                 366

<210> SEQ ID NO 164
<211> LENGTH: 122
<212> TYPE: PRT
<213> ORGANISM: Artificial Sequence
<220> FEATURE:
<223> OTHER INFORMATION: chemically synthesized

<400> SEQUENCE: 164

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Phe Pro His Tyr Tyr Tyr Tyr Met Asp Val Trp
            100                 105                 110
```

```
Gly Lys Gly Thr Met Val Thr Val Ser Ser
        115                 120
```

<210> SEQ ID NO 165
<211> LENGTH: 324
<212> TYPE: DNA
<213> ORGANISM: Artificial Sequence
<220> FEATURE:
<223> OTHER INFORMATION: chemically synthesized

<400> SEQUENCE: 165

```
tcctatgtgc tgactcagcc accctcggtg tccgtggccc cagggcagac ggccagaatt      60
tcctgtgggg gaggcaactt tgacgatgaa ggtgttcact ggtaccagca gaccccaggc     120
caggcccctg tactggtcgt ctatgatgat accggccggc cctcagggat ccctgagcga     180
ttctctggct ccagttctgg gaatacggcc accctgacca tcagccgggt cgaagccggg     240
gatgaggccg actattactg tcaggcgtgg gatagtagta atgatcatcc cgtgttcggc     300
ggagggaccc agctcaccgt ccta                                            324
```

<210> SEQ ID NO 166
<211> LENGTH: 108
<212> TYPE: PRT
<213> ORGANISM: Artificial Sequence
<220> FEATURE:
<223> OTHER INFORMATION: chemically synthesized

<400> SEQUENCE: 166

```
Ser Tyr Val Leu Thr Gln Pro Pro Ser Val Ser Val Ala Pro Gly Gln
 1               5                  10                  15

Thr Ala Arg Ile Ser Cys Gly Gly Gly Asn Phe Asp Asp Glu Gly Val
            20                  25                  30

His Trp Tyr Gln Gln Thr Pro Gly Gln Ala Pro Val Leu Val Val Tyr
        35                  40                  45

Asp Asp Thr Gly Arg Pro Ser Gly Ile Pro Glu Arg Phe Ser Gly Ser
    50                  55                  60

Ser Ser Gly Asn Thr Ala Thr Leu Thr Ile Ser Arg Val Glu Ala Gly
65                  70                  75                  80

Asp Glu Ala Asp Tyr Tyr Cys Gln Ala Trp Asp Ser Ser Asn Asp His
                85                  90                  95

Pro Val Phe Gly Gly Gly Thr Gln Leu Thr Val Leu
            100                 105
```

<210> SEQ ID NO 167
<211> LENGTH: 214
<212> TYPE: PRT
<213> ORGANISM: Artificial Sequence
<220> FEATURE:
<223> OTHER INFORMATION: chemically synthesized

<400> SEQUENCE: 167

```
Ser Tyr Val Leu Thr Gln Pro Pro Ser Val Ser Val Ala Pro Gly Gln
 1               5                  10                  15

Thr Ala Arg Ile Thr Cys Gly Gly Asn Asn Ile Glu Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80
```

```
Asp Glu Ala Asp Tyr Tyr Cys Gln Val Trp Asp Ser Asn Thr Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 168
<211> LENGTH: 449
<212> TYPE: PRT
<213> ORGANISM: Artificial Sequence
<220> FEATURE:
<223> OTHER INFORMATION: chemically synthesized

<400> SEQUENCE: 168

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Phe
            20                  25                  30

Ala Met His Trp Val Arg Gln Ala Pro Gly Lys Gly Leu Glu Trp Met
        35                  40                  45

Gly Gly Phe Val Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Pro Leu Tyr Thr Pro Gly Leu Glu Pro Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 169
<211> LENGTH: 20
<212> TYPE: PRT
<213> ORGANISM: Artificial Sequence
<220> FEATURE:
<223> OTHER INFORMATION: chemically synthesized

<400> SEQUENCE: 169

Glu Gln Val Ala Val Gly Pro Gly Pro Thr Ser Asn Arg Gly Pro Asp
1               5                   10                  15

Gly Leu Asp Val
            20

<210> SEQ ID NO 170
<211> LENGTH: 68
<212> TYPE: PRT
<213> ORGANISM: Artificial Sequence
<220> FEATURE:
<223> OTHER INFORMATION: chemically synthesized

<400> SEQUENCE: 170

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
```

```
                50                  55                  60

Leu Glu Met Ser
65

<210> SEQ ID NO 171
<211> LENGTH: 68
<212> TYPE: PRT
<213> ORGANISM: Artificial Sequence
<220> FEATURE:
<223> OTHER INFORMATION: chemically synthesized

<400> SEQUENCE: 171

Ser Pro His Ala Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
        50                  55                  60

Leu Glu Met Ser
65

<210> SEQ ID NO 172
<211> LENGTH: 68
<212> TYPE: PRT
<213> ORGANISM: Artificial Sequence
<220> FEATURE:
<223> OTHER INFORMATION: chemically synthesized

<400> SEQUENCE: 172

Ser Pro Tyr Gly Ser Asp Thr Thr Pro Cys Cys Phe Ala Tyr Leu Ser
1               5                   10                  15

Leu Ala Leu Pro Arg Ala His Val Lys Glu Tyr Phe Tyr Thr Ser Ser
                20                  25                  30

Lys Cys Ser Asn Leu Ala Val Val Phe Val Thr Arg Arg Asn Arg Gln
            35                  40                  45

Val Cys Ala Asn Pro Glu Lys Lys Trp Val Gln Glu Tyr Ile Asn Tyr
        50                  55                  60

Leu Glu Met Ser
65

<210> SEQ ID NO 173
<211> LENGTH: 33
<212> TYPE: DNA
<213> ORGANISM: Artificial Sequence
<220> FEATURE:
<223> OTHER INFORMATION: chemically synthesized

<400> SEQUENCE: 173
gggggaggca actttgacga tgaaggtgtt cac                              33

<210> SEQ ID NO 174
<211> LENGTH: 21
<212> TYPE: DNA
<213> ORGANISM: Artificial Sequence
<220> FEATURE:
<223> OTHER INFORMATION: chemically synthesized

<400> SEQUENCE: 174
gatgataccg gccggccctc a                                           21
```

```
<210> SEQ ID NO 175
<211> LENGTH: 33
<212> TYPE: DNA
<213> ORGANISM: Artificial Sequence
<220> FEATURE:
<223> OTHER INFORMATION: chemically synthesized

<400> SEQUENCE: 175
caggcgtggg atagtagtaa tgatcatccc gtg                                    33

<210> SEQ ID NO 176
<211> LENGTH: 11
<212> TYPE: PRT
<213> ORGANISM: Artificial Sequence
<220> FEATURE:
<223> OTHER INFORMATION: chemically synthesized

<400> SEQUENCE: 176

Gly Gly Gly Asn Phe Asp Asp Glu Gly Val His
1               5                   10

<210> SEQ ID NO 177
<211> LENGTH: 7
<212> TYPE: PRT
<213> ORGANISM: Artificial Sequence
<220> FEATURE:
<223> OTHER INFORMATION: chemically synthesized

<400> SEQUENCE: 177

Asp Asp Thr Gly Arg Pro Ser
1               5

<210> SEQ ID NO 178
<211> LENGTH: 11
<212> TYPE: PRT
<213> ORGANISM: Artificial Sequence
<220> FEATURE:
<223> OTHER INFORMATION: chemically synthesized

<400> SEQUENCE: 178

Gln Ala Trp Asp Ser Ser Asn Asp His Pro Val
1               5                   10

<210> SEQ ID NO 179
<211> LENGTH: 378
<212> TYPE: DNA
<213> ORGANISM: Artificial Sequence
<220> FEATURE:
<223> OTHER INFORMATION: chemically synthesized

<400> SEQUENCE: 179
gaggtgcagc tgttggagtc tgggggaggc ttggtacagc ctgggggtc cctgagactc        60 tcctgtgcag cctctggatt caccttagc agctatgcca tgagctgggt ccgccaggct       120
ccagggaagg ggctggagtg ggtctcagct attagtggta gtggtggtag cacatactac      180
gcagactccg tgaagggccg gttcaccatc tccagagaca attccaaaaa cacgctgtat      240
ctgcaaatga acagcctgag agccgaggac acggccgtgt attactgtgc aagagtaagg      300
gggagttccc agtacgattt ttggagtggg tccgagtttg actactgggg ccaggggaca      360
atggtcaccg tctcgagt                                                    378

<210> SEQ ID NO 180
<211> LENGTH: 126
<212> TYPE: PRT
<213> ORGANISM: Artificial Sequence
<220> FEATURE:
```

<223> OTHER INFORMATION: chemically synthesized

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Gly Ser Ser Gln Tyr Asp Phe Trp Ser Gly Ser Glu
            100                 105                 110

Phe Asp Tyr Trp Gly Gln Gly Thr Met Val Thr Val Ser Ser
        115                 120                 125

<210> SEQ ID NO 181
<211> LENGTH: 327
<212> TYPE: DNA
<213> ORGANISM: Artificial Sequence
<220> FEATURE:
<223> OTHER INFORMATION: chemically synthesized

<400> SEQUENCE: 181
tcctatgtgc tgactcagcc accctcagtg tcagtggccc caggaaagac ggccagcatt    60
tcctgtgggg gagacaacat tggaggtcaa aatgttcact ggtatcagca gaagccaggc   120
caggcccctg tgctcgtcat ctattatgat accgaccggc cctcagggat ccctgagcga   180
ttctctggct ccaactctgg gaacacggcc accctgtcca tcagcagggt cgaagccgcg   240
gatgaggccg actattactg tcaggtgtgg gatgttgata gtgatcatcc ttgggtgttc   300
ggcggaggga ccaagctgac cgtccta                                       327

<210> SEQ ID NO 182
<211> LENGTH: 109
<212> TYPE: PRT
<213> ORGANISM: Artificial Sequence
<220> FEATURE:
<223> OTHER INFORMATION: chemically synthesized

<400> SEQUENCE: 182

Ser Tyr Val Leu Thr Gln Pro Pro Ser Val Ser Val Ala Pro Gly Lys
1               5                   10                  15

Thr Ala Ser Ile Ser Cys Gly Gly Asp Asn Ile Gly Gly Gln Asn Val
            20                  25                  30

His Trp Tyr Gln Gln Lys Pro Gly Gln Ala Pro Val Leu Val Ile Tyr
        35                  40                  45

Tyr Asp Thr Asp Arg Pro Ser Gly Ile Pro Glu Arg Phe Ser Gly Ser
    50                  55                  60

Asn Ser Gly Asn Thr Ala Thr Leu Ser Ile Ser Arg Val Glu Ala Ala
65                  70                  75                  80

Asp Glu Ala Asp Tyr Tyr Cys Gln Val Trp Asp Val Asp Ser Asp His
                85                  90                  95

Pro Trp Val Phe Gly Gly Gly Thr Lys Leu Thr Val Leu
            100                 105

<210> SEQ ID NO 183
<211> LENGTH: 42
<212> TYPE: DNA
<213> ORGANISM: Artificial Sequence
<220> FEATURE:
<223> OTHER INFORMATION: chemically synthesized

<400> SEQUENCE: 183
actgggagca gctccaacat cggggacggt tatgatgtac ac                42

<210> SEQ ID NO 184
<211> LENGTH: 21
<212> TYPE: DNA
<213> ORGANISM: Artificial Sequence
<220> FEATURE:
<223> OTHER INFORMATION: chemically synthesized

<400> SEQUENCE: 184
ggtaacagta atcggccctc a                                      21

<210> SEQ ID NO 185
<211> LENGTH: 51
<212> TYPE: DNA
<213> ORGANISM: Artificial Sequence
<220> FEATURE:
<223> OTHER INFORMATION: chemically synthesized

<400> SEQUENCE: 185 gtaagggga gttcccagta cgattttggg agtgggtccg agtttgacta c       51

<210> SEQ ID NO 186
<211> LENGTH: 452
<212> TYPE: PRT
<213> ORGANISM: Artificial Sequence
<220> FEATURE:
<223> OTHER INFORMATION: chemically synthesized

<400> SEQUENCE: 186

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Phe Pro His Tyr Tyr Tyr Tyr Met Asp Val Trp
            100                 105                 110

Gly Arg Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 187
<211> LENGTH: 214
<212> TYPE: PRT
<213> ORGANISM: Artificial Sequence
<220> FEATURE:
<223> OTHER INFORMATION: chemically synthesized

<400> SEQUENCE: 187

Ser Tyr Val Leu Thr Gln Pro Pro Ser Val Ser Val Ala Pro Gly Gln
1               5                   10                  15

Thr Ala Arg Ile Thr Cys Glu Gly Asp Asp Thr Asp Ile Gly Thr Val
            20                  25                  30

Asn Trp Tyr Gln Gln Lys Pro Gly Gln Ala Pro Val Leu Val Ile Ser
        35                  40                  45

Glu Asp Gly Tyr Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Phe Trp Asp Val Asp Ser Asp His 85                  90                  95

Pro Val Phe Gly Gly Gly Thr Gln Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                        165                 170                 175

Ser Ser Tyr Leu Ser Leu Thr Pro Glu Gln Trp Lys Ser His Arg Ser
                        180                 185                 190

Tyr Ser Cys Gln Val Thr His Glu Gly Ser Thr Val Glu Lys Thr Val
                        195                 200                 205

Ala Pro Thr Glu Cys Ser
        210

<210> SEQ ID NO 188
<211> LENGTH: 17
<212> TYPE: PRT
<213> ORGANISM: Artificial Sequence
<220> FEATURE:
<223> OTHER INFORMATION: chemically synthesized

<400> SEQUENCE: 188

Val Arg Gly Ser Ser Gln Tyr Asp Phe Trp Ser Gly Ser Glu Phe Asp
1               5                   10                  15

Tyr

<210> SEQ ID NO 189
<211> LENGTH: 33
<212> TYPE: DNA
<213> ORGANISM: Artificial Sequence
<220> FEATURE:
<223> OTHER INFORMATION: chemically synthesized

<400> SEQUENCE: 189
ggaacatggg atgacatcct gaatggttgg gtg                                33

<210> SEQ ID NO 190
<211> LENGTH: 14
<212> TYPE: PRT
<213> ORGANISM: Artificial Sequence
<220> FEATURE:
<223> OTHER INFORMATION: chemically synthesized

<400> SEQUENCE: 190

Thr Gly Ser Ser Asn Ile Gly Asp Gly Tyr Asp Val His
1               5                   10

<210> SEQ ID NO 191
<211> LENGTH: 7
<212> TYPE: PRT
<213> ORGANISM: Artificial Sequence
<220> FEATURE:
<223> OTHER INFORMATION: chemically synthesized

<400> SEQUENCE: 191

Gly Asn Ser Asn Arg Pro Ser
1               5

```
<210> SEQ ID NO 192
<211> LENGTH: 11
<212> TYPE: PRT
<213> ORGANISM: Artificial Sequence
<220> FEATURE:
<223> OTHER INFORMATION: chemically synthesized

<400> SEQUENCE: 192

Gly Gly Asp Asn Ile Gly Gly Gln Asn Val His
1               5                   10

<210> SEQ ID NO 193
<211> LENGTH: 7
<212> TYPE: PRT
<213> ORGANISM: Artificial Sequence
<220> FEATURE:
<223> OTHER INFORMATION: chemically synthesized

<400> SEQUENCE: 193

Tyr Asp Thr Asp Arg Pro Ser
1               5

<210> SEQ ID NO 194
<211> LENGTH: 12
<212> TYPE: PRT
<213> ORGANISM: Artificial Sequence
<220> FEATURE:
<223> OTHER INFORMATION: chemically synthesized

<400> SEQUENCE: 194

Gln Val Trp Asp Val Asp Ser Asp His Pro Trp Val
1               5                   10

<210> SEQ ID NO 195
<211> LENGTH: 324
<212> TYPE: DNA
<213> ORGANISM: Artificial Sequence
<220> FEATURE:
<223> OTHER INFORMATION: chemically synthesized

<400> SEQUENCE: 195
tcctatgtgc tgactcagcc accctcggtg tcagtggccc caggacagac ggccaggatt    60
acctgtgggg gaaacaacat tgaaagtaaa agtgtgcact ggtaccagca gaagccaggc   120
caggcccctg tgctggtggt ctatgatgat agcgaccggc cctcaggat ccctgagcga    180 ttctctggct ccaactctgg gaacacggcc accctgacca tcagcagggt cgaagccggg   240
gatgaggccg actattactg tcaggtgtgg gatagtaata ctgatcattg ggtgttcggc   300
ggagggacca aggtcaccgt ccta                                           324

<210> SEQ ID NO 196
<211> LENGTH: 108
<212> TYPE: PRT
<213> ORGANISM: Artificial Sequence
<220> FEATURE:
<223> OTHER INFORMATION: chemically synthesized

<400> SEQUENCE: 196

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Glu Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
```

```
                      50                  55                  60
Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Asn Thr Asp His
                 85                  90                  95

Trp Val Phe Gly Gly Gly Thr Lys Val Thr Val Leu
            100                 105

<210> SEQ ID NO 197
<211> LENGTH: 21
<212> TYPE: DNA
<213> ORGANISM: Artificial Sequence
<220> FEATURE:
<223> OTHER INFORMATION: chemically synthesized

<400> SEQUENCE: 197
ctcttctgag atgagttttt g                                           21

<210> SEQ ID NO 198
<211> LENGTH: 30
<212> TYPE: DNA
<213> ORGANISM: Artificial Sequence
<220> FEATURE:
<223> OTHER INFORMATION: chemically synthesized

<400> SEQUENCE: 198
ttattattcg caattccttt agttgttcct                                  30

<210> SEQ ID NO 199
<211> LENGTH: 360
<212> TYPE: DNA
<213> ORGANISM: Artificial Sequence
<220> FEATURE:
<223> OTHER INFORMATION: chemically synthesized

<400> SEQUENCE: 199
caggtgcagc tggtgcagtc tggggctgag gtgaagaagc ctggggcctc agtgaaggtc    60
tcctgcaagg tttccggata cgccctcagt gaattatcca tacactgggt gcgacaggct   120
cctggcaaag gccttgagtg gatgtcgtat attgatcctg aagatggtga accaatttac   180
gcacagaagt tccagggcag agccaccatg accgaggact catctacaga cacagcctac   240
atggagatgg gcagcctgac atctgacgac acggccgttt attactgtgc aggtgtcact   300
ggaagtactt cggatgcctt tgatctctgg ggccggggaa ccctggtcac cgtctcgagt   360

<210> SEQ ID NO 200
<211> LENGTH: 120
<212> TYPE: PRT
<213> ORGANISM: Artificial Sequence
<220> FEATURE:
<223> OTHER INFORMATION: chemically synthesized

<400> SEQUENCE: 200

Gln Val Gln Leu Val Gln Ser Gly Ala Glu Val Lys Lys Pro Gly Ala
  1               5                  10                  15

Ser Val Lys Val Ser Cys Lys Val Ser Gly Tyr Ala Leu Ser Glu Leu
                 20                  25                  30

Ser Ile His Trp Val Arg Gln Ala Pro Gly Lys Gly Leu Glu Trp Met
             35                  40                  45

Ser Tyr Ile Asp Pro Glu Asp Gly Glu Pro Ile Tyr Ala Gln Lys Phe
         50                  55                  60

Gln Gly Arg Ala Thr Met Thr Glu Asp Ser Ser Thr Asp Thr Ala Tyr
```

```
                    65                  70                  75                  80
Met Glu Met Gly Ser Leu Thr Ser Asp Asp Thr Ala Val Tyr Tyr Cys
                        85                  90                  95

Ala Gly Val Thr Gly Ser Thr Ser Asp Ala Phe Asp Leu Trp Gly Arg
                100                 105                 110

Gly Thr Leu Val Thr Val Ser Ser
        115                 120

<210> SEQ ID NO 201
<211> LENGTH: 324
<212> TYPE: DNA
<213> ORGANISM: Artificial Sequence
<220> FEATURE:
<223> OTHER INFORMATION: chemically synthesized

<400> SEQUENCE: 201
tcctatgtgc tgactcagga ccccctcggtg tcagtggccc caggacagac ggccaggatc      60
acctgtgggg gagccaatct ttggggtcta ggtgtccatt ggtatcaaca aaagtcaggc     120
caggcccctg tgttggtcgt ctctgataat agcgaccggg cctcagggat ccctgagcga     180
ttctctggct ccaattctgg gaccacggcc accctgaccc tcagcagggt cgaagtcggc     240
gatgaggccg actattactg tcaggtgtgg gatagtagta gtgatcactg ggtgttcggc     300
ggcaggacca agctgaccgt ccta                                            324

<210> SEQ ID NO 202
<211> LENGTH: 108
<212> TYPE: PRT
<213> ORGANISM: Artificial Sequence
<220> FEATURE:
<223> OTHER INFORMATION: chemically synthesized

<400> SEQUENCE: 202

Ser Tyr Val Leu Thr Gln Asp Pro Ser Val Ser Val Ala Pro Gly Gln
1               5                   10                  15

Thr Ala Arg Ile Thr Cys Gly Gly Ala Asn Leu Trp Gly Leu Gly Val
            20                  25                  30

His Trp Tyr Gln Gln Lys Ser Gly Gln Ala Pro Val Leu Val Val Ser
        35                  40                  45

Asp Asn Ser Asp Arg Ala Ser Gly Ile Pro Glu Arg Phe Ser Gly Ser
    50                  55                  60

Asn Ser Gly Thr Thr Ala Thr Leu Thr Leu Ser Arg Val Glu Val Gly
65                  70                  75                  80

Asp Glu Ala Asp Tyr Tyr Cys Gln Val Trp Asp Ser Ser Ser Asp His
                85                  90                  95

Trp Val Phe Gly Gly Arg Thr Lys Leu Thr Val Leu
            100                 105

<210> SEQ ID NO 203
<211> LENGTH: 15
<212> TYPE: DNA
<213> ORGANISM: Artificial Sequence
<220> FEATURE:
<223> OTHER INFORMATION: chemically synthesized

<400> SEQUENCE: 203
gaattatcca tacac                                                       15

<210> SEQ ID NO 204
<211> LENGTH: 51
<212> TYPE: DNA
```

<213> ORGANISM: Artificial Sequence
<220> FEATURE:
<223> OTHER INFORMATION: chemically synthesized

<400> SEQUENCE: 204
tatattgatc ctgaagatgg tgaaccaatt tacgcacaga agttccaggg c    51

<210> SEQ ID NO 205
<211> LENGTH: 33
<212> TYPE: DNA
<213> ORGANISM: Artificial Sequence
<220> FEATURE:
<223> OTHER INFORMATION: chemically synthesized

<400> SEQUENCE: 205
gtcactggaa gtacttcgga tgcctttgat ctc    33

<210> SEQ ID NO 206
<211> LENGTH: 68
<212> TYPE: PRT
<213> ORGANISM: Artificial Sequence
<220> FEATURE:
<223> OTHER INFORMATION: chemically synthesized

<400> SEQUENCE: 206

Ser Pro Tyr Gly Ser Asp Thr Thr Pro Cys Cys Phe Ala Tyr Leu Ser
1               5                   10                  15

Leu Ala Leu Pro Arg Ala His Val Lys Glu Tyr Phe Tyr Thr Ser Ser
            20                  25                  30

Lys Cys Ser Asn Leu Ala Val Val Phe Val Thr Arg Arg Asn Arg Gln
        35                  40                  45

Val Cys Ala Asn Pro Glu Lys Lys Trp Val Gln Glu Tyr Ile Asn Tyr
    50                  55                  60

Leu Glu Met Ser
65

<210> SEQ ID NO 207
<211> LENGTH: 17
<212> TYPE: PRT
<213> ORGANISM: Artificial Sequence
<220> FEATURE:
<223> OTHER INFORMATION: chemically synthesized

<400> SEQUENCE: 207

Tyr Ile Asp Pro Glu Asp Gly Glu Pro Ile Tyr Ala Gln Lys Phe Gln
1               5                   10                  15

Gly

<210> SEQ ID NO 208
<211> LENGTH: 11
<212> TYPE: PRT
<213> ORGANISM: Artificial Sequence
<220> FEATURE:
<223> OTHER INFORMATION: chemically synthesized

<400> SEQUENCE: 208

Val Thr Gly Ser Thr Ser Asp Ala Phe Asp Leu
1               5                   10

<210> SEQ ID NO 209
<211> LENGTH: 33
<212> TYPE: DNA
<213> ORGANISM: Artificial Sequence
<220> FEATURE:
<223> OTHER INFORMATION: chemically synthesized

```
<400> SEQUENCE: 209
gggggagcca atctttgggg tctaggtgtc cat                                    33

<210> SEQ ID NO 210
<211> LENGTH: 21
<212> TYPE: DNA
<213> ORGANISM: Artificial Sequence
<220> FEATURE:
<223> OTHER INFORMATION: chemically synthesized

<400> SEQUENCE: 210
gataatagcg accgggcctc a                                                 21

<210> SEQ ID NO 211
<211> LENGTH: 33
<212> TYPE: DNA
<213> ORGANISM: Artificial Sequence
<220> FEATURE:
<223> OTHER INFORMATION: chemically synthesized

<400> SEQUENCE: 211
caggtgtggg atagtagtag tgatcactgg gtg                                    33

<210> SEQ ID NO 212
<211> LENGTH: 11
<212> TYPE: PRT
<213> ORGANISM: Artificial Sequence
<220> FEATURE:
<223> OTHER INFORMATION: chemically synthesized

<400> SEQUENCE: 212

Gly Gly Ala Asn Leu Trp Gly Leu Gly Val His
1               5                   10

<210> SEQ ID NO 213
<211> LENGTH: 7
<212> TYPE: PRT
<213> ORGANISM: Artificial Sequence
<220> FEATURE:
<223> OTHER INFORMATION: chemically synthesized

<400> SEQUENCE: 213

Asp Asn Ser Asp Arg Ala Ser
1               5

<210> SEQ ID NO 214
<211> LENGTH: 11
<212> TYPE: PRT
<213> ORGANISM: Artificial Sequence
<220> FEATURE:
<223> OTHER INFORMATION: chemically synthesized

<400> SEQUENCE: 214

Gln Val Trp Asp Ser Ser Ser Asp His Trp Val
1               5                   10

<210> SEQ ID NO 215
<211> LENGTH: 387
<212> TYPE: DNA
<213> ORGANISM: Artificial Sequence
<220> FEATURE:
<223> OTHER INFORMATION: chemically synthesized

<400> SEQUENCE: 215
caggtgcagc tggtgcagtc tggggctgag gtgaagaagc ctgggtcgtc ggtgaaggtc       60
```

```
tcctgcaagg cctctggagg catctccgac aactatgctc tcagctgggt gcgacaggcc    120
cctggccaag gacttgagtg gatgggaggg ttcatccctc tcgtcgatac tacgaactac    180
gcacagaggt ttcagggcag actcacgatt accgcggacg actccatgag tacagtctac    240
atggaactaa gaagcctgcg atctgacgac acggccatgt attattgtgc gagagagcag    300
gtggcggtgg gacctggacc cacctcagac cgggggcccg atggtcttga tgtctggggc    360
caagggacaa tggtcaccgt ctcgagt                                        387
```

<210> SEQ ID NO 216
<211> LENGTH: 129
<212> TYPE: PRT
<213> ORGANISM: Artificial Sequence
<220> FEATURE:
<223> OTHER INFORMATION: chemically synthesized

<400> SEQUENCE: 216

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ile Ser Asp Asn Tyr
            20                  25                  30

Ala Leu Ser Trp Val Arg Gln Ala Pro Gly Gln Gly Leu Glu Trp Met
        35                  40                  45

Gly Gly Phe Ile Pro Leu Val Asp Thr Thr Asn Tyr Ala Gln Arg Phe
    50                  55                  60

Gln Gly Arg Leu Thr Ile Thr Ala Asp Asp Ser Met Ser Thr Val Tyr
65                  70                  75                  80

Met Glu Leu Arg Ser Leu Arg Ser Asp Asp Thr Ala Met Tyr Tyr Cys
                85                  90                  95

Ala Arg Glu Gln Val Ala Val Gly Pro Gly Pro Thr Ser Asp Arg Gly
               100                 105                 110

Pro Asp Gly Leu Asp Val Trp Gly Gln Gly Thr Met Val Thr Val Ser
           115                 120                 125

Ser
```

<210> SEQ ID NO 217
<211> LENGTH: 339
<212> TYPE: DNA
<213> ORGANISM: Artificial Sequence
<220> FEATURE:
<223> OTHER INFORMATION: chemically synthesized

<400> SEQUENCE: 217

```
cagtctgtgc tgactcagcc gtcctcagtg tctggggccc cagggcacag ggtcaccatt    60
tcctgcactg ggagcaactc caacctcggg gcggattatg atgtacactg gtatcagcag    120
cttccaggat cagcccccaa actcctcatc tatgataaca acattcgtcc ctcaggggtc    180
cctgcccgat tctctggctc caagtctggc acctcagcct ccctggccat cactgggctc    240
caggctgaag atgaggctga ttattactgc cagtcgtatg acaccggcct gacttcttcg    300
gatgtgatat cggcggagg gaccaagctg accgtccta                            339
```

<210> SEQ ID NO 218
<211> LENGTH: 113
<212> TYPE: PRT
<213> ORGANISM: Artificial Sequence
<220> FEATURE:
<223> OTHER INFORMATION: chemically synthesized

<400> SEQUENCE: 218

-continued

```
Gln Ser Val Leu Thr Gln Pro Ser Ser Val Ser Gly Ala Pro Gly His
1               5                   10                  15

Arg Val Thr Ile Ser Cys Thr Gly Ser Asn Ser Asn Leu Gly Ala Asp
            20                  25                  30

Tyr Asp Val His Trp Tyr Gln Gln Leu Pro Gly Ser Ala Pro Lys Leu
        35                  40                  45

Leu Ile Tyr Asp Asn Asn Ile Arg Pro Ser Gly Val Pro Ala Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Gly
                85                  90                  95

Leu Thr Ser Ser Asp Val Ile Phe Gly Gly Gly Thr Lys Leu Thr Val
            100                 105                 110

Leu
```

<210> SEQ ID NO 219
<211> LENGTH: 15
<212> TYPE: DNA
<213> ORGANISM: Artificial Sequence
<220> FEATURE:
<223> OTHER INFORMATION: chemically synthesized

<400> SEQUENCE: 219
aactatgctc tcagc     15

<210> SEQ ID NO 220
<211> LENGTH: 51
<212> TYPE: DNA
<213> ORGANISM: Artificial Sequence
<220> FEATURE:
<223> OTHER INFORMATION: chemically synthesized

<400> SEQUENCE: 220
gggttcatcc ctctcgtcga tactacgaac tacgcacaga ggtttcaggg c     51

<210> SEQ ID NO 221
<211> LENGTH: 60
<212> TYPE: DNA
<213> ORGANISM: Artificial Sequence
<220> FEATURE:
<223> OTHER INFORMATION: chemically synthesized

<400> SEQUENCE: 221
gagcaggtgg cggtgggacc tggacccacc tcagaccggg ggcccgatgg tcttgatgtc     60

<210> SEQ ID NO 222
<211> LENGTH: 5
<212> TYPE: PRT
<213> ORGANISM: Artificial Sequence
<220> FEATURE:
<223> OTHER INFORMATION: chemically synthesized

<400> SEQUENCE: 222

Asn Tyr Ala Leu Ser
1               5

<210> SEQ ID NO 223
<211> LENGTH: 17
<212> TYPE: PRT
<213> ORGANISM: Artificial Sequence
<220> FEATURE:
<223> OTHER INFORMATION: chemically synthesized

```
<400> SEQUENCE: 223

Gly Phe Ile Pro Leu Val Asp Thr Thr Asn Tyr Ala Gln Arg Phe Gln
1               5                   10                  15
Gly

<210> SEQ ID NO 224
<211> LENGTH: 20
<212> TYPE: PRT
<213> ORGANISM: Artificial Sequence
<220> FEATURE:
<223> OTHER INFORMATION: chemically synthesized

<400> SEQUENCE: 224

Glu Gln Val Ala Val Gly Pro Gly Pro Thr Ser Asp Arg Gly Pro Asp
1               5                   10                  15
Gly Leu Asp Val
            20

<210> SEQ ID NO 225
<211> LENGTH: 42
<212> TYPE: DNA
<213> ORGANISM: Artificial Sequence
<220> FEATURE:
<223> OTHER INFORMATION: chemically synthesized

<400> SEQUENCE: 225
actgggagca actccaacct cggggcggat tatgatgtac ac                          42

<210> SEQ ID NO 226
<211> LENGTH: 21
<212> TYPE: DNA
<213> ORGANISM: Artificial Sequence
<220> FEATURE:
<223> OTHER INFORMATION: chemically synthesized

<400> SEQUENCE: 226
gataacaaca ttcgtccctc a                                                 21

<210> SEQ ID NO 227
<211> LENGTH: 39
<212> TYPE: DNA
<213> ORGANISM: Artificial Sequence
<220> FEATURE:
<223> OTHER INFORMATION: chemically synthesized

<400> SEQUENCE: 227
cagtcgtatg acaccggcct gacttcttcg gatgtgata                              39

<210> SEQ ID NO 228
<211> LENGTH: 14
<212> TYPE: PRT
<213> ORGANISM: Artificial Sequence
<220> FEATURE:
<223> OTHER INFORMATION: chemically synthesized

<400> SEQUENCE: 228

Thr Gly Ser Asn Ser Asn Leu Gly Ala Asp Tyr Asp Val His
1               5                   10

<210> SEQ ID NO 229
<211> LENGTH: 7
<212> TYPE: PRT
<213> ORGANISM: Artificial Sequence
<220> FEATURE:
<223> OTHER INFORMATION: chemically synthesized
```

<400> SEQUENCE: 229

Asp Asn Asn Ile Arg Pro Ser
1               5

<210> SEQ ID NO 230
<211> LENGTH: 13
<212> TYPE: PRT
<213> ORGANISM: Artificial Sequence
<220> FEATURE:
<223> OTHER INFORMATION: chemically synthesized

<400> SEQUENCE: 230

Gln Ser Tyr Asp Thr Gly Leu Thr Ser Ser Asp Val Ile
1               5                  10

<210> SEQ ID NO 231
<211> LENGTH: 360
<212> TYPE: DNA
<213> ORGANISM: Artificial Sequence
<220> FEATURE:
<223> OTHER INFORMATION: chemically synthesized

<400> SEQUENCE: 231
gaggtgcagc tggtgcagtc tgggcctgag gtgaagaagc ctggggccac agtgaaaatt      60
tcctgcaacg tctctgcaga aaccttcacc gactactaca tacactgggt caaacaggcc    120
cctggaagag ggctggagtg gatggggctt gttgattctg aagaagatgg tgaaacatta    180
ttcgcagaga ctttcagggg cagagtcgcc ctaaccgcgg acaggtccac aaacaccgcc    240
tacatggagt tgcgcagcct gagacatgac gacacggccg tctattattg tgcagcagaa    300
tatggtgaat atgggttctt ccaatcgtgg ggccagggaa ccctggtcac cgtctcgagt    360

<210> SEQ ID NO 232
<211> LENGTH: 120
<212> TYPE: PRT
<213> ORGANISM: Artificial Sequence
<220> FEATURE:
<223> OTHER INFORMATION: chemically synthesized

<400> SEQUENCE: 232

Glu Val Gln Leu Val Gln Ser Gly Pro Glu Val Lys Lys Pro Gly Ala
1               5                  10                  15

Thr Val Lys Ile Ser Cys Asn Val Ser Ala Glu Thr Phe Thr Asp Tyr
            20                  25                  30

Tyr Ile His Trp Val Lys Gln Ala Pro Gly Arg Gly Leu Glu Trp Met
        35                  40                  45

Gly Leu Val Asp Ser Glu Glu Asp Gly Glu Thr Leu Phe Ala Glu Thr
    50                  55                  60

Phe Arg Gly Arg Val Ala Leu Thr Ala Asp Arg Ser Thr Asn Thr Ala
65                  70                  75                  80

Tyr Met Glu Leu Arg Ser Leu Arg His Asp Asp Thr Ala Val Tyr Tyr
                85                  90                  95

Cys Ala Ala Glu Tyr Gly Glu Tyr Gly Phe Phe Gln Ser Trp Gly Gln
            100                 105                 110

Gly Thr Leu Val Thr Val Ser Ser
        115                 120

<210> SEQ ID NO 233
<211> LENGTH: 336
<212> TYPE: DNA
<213> ORGANISM: Artificial Sequence
<220> FEATURE:

<223> OTHER INFORMATION: chemically synthesized

<400> SEQUENCE: 233

```
cagtctgtgc tgactcagcc accctcagtg tctggggccc cagggcagag ggtcaccatc    60
tcctgcactg ggagcagctc aacatcggg gcagattatg atgtaaactg gtaccagcag    120
cttccaggaa cttcccccaa actcctcatc tatggtgaca tcaatcggcc ctcaggggtc    180
cctgaccgat tctctgcctc caagtctggc acctcagcct ccctggccat cactgggctc    240
caggctgagg atgaggctga ttattactgc cagtcgtttg acaacagcct gagtgggtct    300
gtgattttcg gcggagggac caagctgacc gtccta                             336
```

<210> SEQ ID NO 234
<211> LENGTH: 112
<212> TYPE: PRT
<213> ORGANISM: Artificial Sequence
<220> FEATURE:
<223> OTHER INFORMATION: chemically synthesized

<400> SEQUENCE: 234

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Asp
            20                  25                  30
Tyr Asp Val Asn Trp Tyr Gln Gln Leu Pro Gly Thr Ser Pro Lys Leu
        35                  40                  45
Leu Ile Tyr Gly Asp Ile Asn Arg Pro Ser Gly Val Pro Asp Arg Phe
    50                  55                  60
Ser Ala Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Phe Asp Asn Ser
                85                  90                  95
Leu Ser Gly Ser Val Ile Phe Gly Gly Gly Thr Lys Leu Thr Val Leu
            100                 105                 110
```

<210> SEQ ID NO 235
<211> LENGTH: 11
<212> TYPE: PRT
<213> ORGANISM: Artificial Sequence
<220> FEATURE:
<223> OTHER INFORMATION: chemically synthesized

<400> SEQUENCE: 235

```
Gly Thr Trp Asp Asp Ile Leu Asn Gly Trp Val
1               5                   10
```

<210> SEQ ID NO 236
<211> LENGTH: 54
<212> TYPE: DNA
<213> ORGANISM: Artificial Sequence
<220> FEATURE:
<223> OTHER INFORMATION: chemically synthesized

<400> SEQUENCE: 236

```
cttgttgatt ctgaagaaga tggtgaaaca ttattcgcag agactttcag gggc          54
```

<210> SEQ ID NO 237
<211> LENGTH: 30
<212> TYPE: DNA
<213> ORGANISM: Artificial Sequence
<220> FEATURE:
<223> OTHER INFORMATION: chemically synthesized

<400> SEQUENCE: 237
gaatatggtg aatatgggtt cttccaatcg                                              30

<210> SEQ ID NO 238
<211> LENGTH: 449
<212> TYPE: PRT
<213> ORGANISM: Artificial Sequence
<220> FEATURE:
<223> OTHER INFORMATION: chemically synthesized

<400> SEQUENCE: 238

```
Gln Val Gln Leu Val Gln Ser Gly Ala Glu Val Lys Lys Pro Gly Ala
1               5                   10                  15
Ser Val Lys Val Ser Cys Lys Val Ser Gly Tyr Thr Leu Thr Glu Phe
            20                  25                  30
Ala Met His Trp Val Arg Gln Ala Pro Gly Lys Gly Leu Glu Trp Met
        35                  40                  45
Gly Gly Phe Val Pro Glu Asp Gly Glu Thr Ile Tyr Ala Gln Lys Phe
    50                  55                  60
Gln Gly Arg Val Thr Met Thr Glu Asp Thr Ser Thr Asp Thr Ala Tyr
65                  70                  75                  80
Met Glu Leu Ser Ser Leu Arg Ser Asp Thr Ala Val Tyr Tyr Cys
                85                  90                  95
Ala Thr Asp Pro Leu Tyr Glu Ser Phe Ser Val Trp Gly Gln Gly
            100                 105                 110
Thr Thr Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
```

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 239
<211> LENGTH: 18
<212> TYPE: PRT
<213> ORGANISM: Artificial Sequence
<220> FEATURE:
<223> OTHER INFORMATION: chemically synthesized

<400> SEQUENCE: 239

Leu Val Asp Ser Glu Glu Asp Gly Glu Thr Leu Phe Ala Glu Thr Phe
1               5                   10                  15

Arg Gly

<210> SEQ ID NO 240
<211> LENGTH: 10
<212> TYPE: PRT
<213> ORGANISM: Artificial Sequence
<220> FEATURE:
<223> OTHER INFORMATION: chemically synthesized

<400> SEQUENCE: 240

Glu Tyr Gly Glu Tyr Gly Phe Phe Gln Ser
1               5                   10

<210> SEQ ID NO 241
<211> LENGTH: 42
<212> TYPE: DNA
<213> ORGANISM: Artificial Sequence
<220> FEATURE:
<223> OTHER INFORMATION: chemically synthesized

<400> SEQUENCE: 241
actgggagca gctccaacat cggggcagat tatgatgtaa ac                              42

<210> SEQ ID NO 242
<211> LENGTH: 21
<212> TYPE: DNA
<213> ORGANISM: Artificial Sequence
<220> FEATURE:
<223> OTHER INFORMATION: chemically synthesized

<400> SEQUENCE: 242
ggtgacatca atcggccctc a                                                    21

<210> SEQ ID NO 243
<211> LENGTH: 36
<212> TYPE: DNA
<213> ORGANISM: Artificial Sequence
<220> FEATURE:
<223> OTHER INFORMATION: chemically synthesized

```
<400> SEQUENCE: 243
cagtcgtttg acaacagcct gagtgggtct gtgatt                                  36

<210> SEQ ID NO 244
<211> LENGTH: 14
<212> TYPE: PRT
<213> ORGANISM: Artificial Sequence
<220> FEATURE:
<223> OTHER INFORMATION: chemically synthesized

<400> SEQUENCE: 244

Thr Gly Ser Ser Ser Asn Ile Gly Ala Asp Tyr Asp Val Asn
1               5                   10

<210> SEQ ID NO 245
<211> LENGTH: 7
<212> TYPE: PRT
<213> ORGANISM: Artificial Sequence
<220> FEATURE:
<223> OTHER INFORMATION: chemically synthesized

<400> SEQUENCE: 245

Gly Asp Ile Asn Arg Pro Ser
1               5

<210> SEQ ID NO 246
<211> LENGTH: 12
<212> TYPE: PRT
<213> ORGANISM: Artificial Sequence
<220> FEATURE:
<223> OTHER INFORMATION: chemically synthesized

<400> SEQUENCE: 246

Gln Ser Phe Asp Asn Ser Leu Ser Gly Ser Val Ile
1               5                   10

<210> SEQ ID NO 247
<211> LENGTH: 387
<212> TYPE: DNA
<213> ORGANISM: Artificial Sequence
<220> FEATURE:
<223> OTHER INFORMATION: chemically synthesized

<400> SEQUENCE: 247
caggtgcagc tggtgcagtc tggggctgag gtgaagaagc cggggtcgtc ggtgaaggtc      60
tcctgcaaga tttctggagg catctccgac aactacgctc tgagctgggt gcgacaggcc     120
cctgggcaag gacttgagtg gatgggagcg gtcatccctc tcgtcgagac tacgagctac     180
gcacagaggt tccagggcag actcacaatt accgcggacg actccttgaa tacactgtac     240
atggaattgg gaagcctgcg atctgacgac acggccatgt attactgtgc gagagagcag     300
gtggcggtgg gacctggacc cacttcaaat cggggggccg atggcctaga tgtctgggc     360 agagggacaa tggtcaccgt ctcgagt                                          387

<210> SEQ ID NO 248
<211> LENGTH: 129
<212> TYPE: PRT
<213> ORGANISM: Artificial Sequence
<220> FEATURE:
<223> OTHER INFORMATION: chemically synthesized

<400> SEQUENCE: 248

Gln Val Gln Leu Val Gln Ser Gly Ala Glu Val Lys Lys Pro Gly Ser
1               5                   10                  15
```

```
Ser Val Lys Val Ser Cys Lys Ile Ser Gly Gly Ile Ser Asp Asn Tyr
            20                  25                  30

Ala Leu Ser Trp Val Arg Gln Ala Pro Gly Gln Gly Leu Glu Trp Met
        35                  40                  45

Gly Ala Val Ile Pro Leu Val Glu Thr Thr Ser Tyr Ala Gln Arg Phe
50                      55                  60

Gln Gly Arg Leu Thr Ile Thr Ala Asp Asp Ser Leu Asn Thr Leu Tyr
65                  70                  75                  80

Met Glu Leu Gly Ser Leu Arg Ser Asp Asp Thr Ala Met Tyr Tyr Cys
                85                  90                  95

Ala Arg Glu Gln Val Ala Val Gly Pro Gly Thr Ser Asn Arg Gly
                100                 105                 110

Pro Asp Gly Leu Asp Val Trp Gly Arg Gly Thr Met Val Thr Val Ser
            115                 120                 125

Ser
```

<210> SEQ ID NO 249
<211> LENGTH: 333
<212> TYPE: DNA
<213> ORGANISM: Artificial Sequence
<220> FEATURE:
<223> OTHER INFORMATION: chemically synthesized

<400> SEQUENCE: 249

```
cagtctgtgc tgactcagcc accctcagtg tctggggccc cagggcagag ggtcaccatc      60
tcctgcactg ggagcagctc caacatcggg gacggttatg atgtacactg gtatcagcag     120
cttccaggaa cagcccccaa actcctcatc tatggtaaca gtaatcggcc ctcaggggtc     180
cctgaccgat tctctggctc cacctctgcc acctccgcct ccctggccat ccgtgggctc     240
cagtctgagg atgaggctga ttactactgt ggaacatggg atgacatcct gaatggttgg     300
gtgttcggcg gagggaccaa gctgaccgtc cta                                  333
```

<210> SEQ ID NO 250
<211> LENGTH: 111
<212> TYPE: PRT
<213> ORGANISM: Artificial Sequence
<220> FEATURE:
<223> OTHER INFORMATION: chemically synthesized

<400> SEQUENCE: 250

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Asp Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
50                  55                  60

Ser Gly Ser Thr Ser Gly Thr Ser Ala Ser Leu Ala Ile Arg Gly Leu
65                  70                  75                  80

Gln Ser Glu Asp Glu Ala Asp Tyr Tyr Cys Gly Thr Trp Asp Asp Ile
                85                  90                  95

Leu Asn Gly Trp Val Phe Gly Gly Gly Thr Lys Leu Thr Val Leu
            100                 105                 110
```

<210> SEQ ID NO 251
<211> LENGTH: 15
<212> TYPE: DNA

<213> ORGANISM: Artificial Sequence
<220> FEATURE:
<223> OTHER INFORMATION: chemically synthesized

<400> SEQUENCE: 251
aactacgctc tgagc                                                          15

<210> SEQ ID NO 252
<211> LENGTH: 51
<212> TYPE: DNA
<213> ORGANISM: Artificial Sequence
<220> FEATURE:
<223> OTHER INFORMATION: chemically synthesized

<400> SEQUENCE: 252
gcggtcatcc ctctcgtcga gactacgagc tacgcacaga ggttccaggg c                  51

<210> SEQ ID NO 253
<211> LENGTH: 60
<212> TYPE: DNA
<213> ORGANISM: Artificial Sequence
<220> FEATURE:
<223> OTHER INFORMATION: chemically synthesized

<400> SEQUENCE: 253
gagcaggtgg cggtgggacc tggacccact tcaaatcggg ggcccgatgg cctagatgtc         60

<210> SEQ ID NO 254
<211> LENGTH: 214
<212> TYPE: PRT
<213> ORGANISM: Artificial Sequence
<220> FEATURE:
<223> OTHER INFORMATION: chemically synthesized

<400> SEQUENCE: 254

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Glu Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Asn Thr Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

```
Ala Pro Thr Glu Cys Ser
    210

<210> SEQ ID NO 255
<211> LENGTH: 17
<212> TYPE: PRT
<213> ORGANISM: Artificial Sequence
<220> FEATURE:
<223> OTHER INFORMATION: chemically synthesized

<400> SEQUENCE: 255

Ala Val Ile Pro Leu Val Glu Thr Thr Ser Tyr Ala Gln Arg Phe Gln
1               5                   10                  15

Gly
```